United States Patent
Kang et al.

(10) Patent No.: US 11,672,950 B2
(45) Date of Patent: Jun. 13, 2023

(54) FLEXIBLE CATHETERS AND RELATED METHODS

(71) Applicant: FOLDÉ INC., Pleasanton, CA (US)

(72) Inventors: Young M. Kang, Pleasanton, CA (US); John P. Lunsford, San Carlos, CA (US); Robert S. Bley, Menlo Park, CA (US); MingYao Ding, Berkeley, CA (US); Sammy S. Datwani, Pleasanton, CA (US)

(73) Assignee: FOLDÉ INC., Pleasanton, CA (US)

( * ) Notice: Subject to any disclaimer, the term of this patent is extended or adjusted under 35 U.S.C. 154(b) by 0 days.

(21) Appl. No.: 17/843,737

(22) Filed: Jun. 17, 2022

(65) Prior Publication Data
US 2022/0379080 A1    Dec. 1, 2022

Related U.S. Application Data

(63) Continuation of application No. PCT/US2022/030962, filed on May 25, 2022.
(Continued)

(51) Int. Cl.
*A61M 25/00* (2006.01)
*A61M 25/10* (2013.01)

(52) U.S. Cl.
CPC .... *A61M 25/0054* (2013.01); *A61M 25/0009* (2013.01); *A61M 25/0053* (2013.01); *A61M 25/0068* (2013.01); *A61M 25/10* (2013.01)

(58) Field of Classification Search
CPC .......... A61M 25/0054; A61M 25/0009; A61M 25/0053; A61M 25/0068; A61M 25/10
See application file for complete search history.

(56) References Cited

U.S. PATENT DOCUMENTS

| | | |
|---|---|---|
| 4,155,364 A | 5/1979 | Boxer |
| 4,292,270 A | 9/1981 | Hannah et al. |

(Continued)

FOREIGN PATENT DOCUMENTS

| | | |
|---|---|---|
| EP | 0384476 B1 | 8/1990 |
| WO | 2018049828 A1 | 3/2018 |

OTHER PUBLICATIONS

Villanueva et al. article titled "Difficult Catheterization: Tricks of the Trade," © 2011 American Urological Association, Linthicum, MD, AUA Update Series, Lesson 5, vol. 30, 2011 (8 pages).

(Continued)

*Primary Examiner* — Laura A Bouchelle
*Assistant Examiner* — John A Doubrava
(74) *Attorney, Agent, or Firm* — Aurora Consulting LLC; Ashley Sloat

(57) ABSTRACT

Described herein are various embodiments of flexible catheters comprising one or more flexibility regions. In one embodiment, a catheter comprises an elongate body having a proximal segment and a distal segment; a first lumen defined by the elongate body and configured for drainage of a liquid from a bodily region; and a plurality of flexibility regions on or in the distal segment of the elongate body. The plurality of flexibility regions, collectively, is configured to passively bend anteriorly. Further, at least one of the plurality of flexibility regions has a defined percent volume of material removed and a defined cut depth percentage. The features and arrangement of the flexibility regions described herein result in the catheter requiring reduced force during insertion into a bodily lumen.

19 Claims, 57 Drawing Sheets

Related U.S. Application Data

(60) Provisional application No. 63/193,228, filed on May 26, 2021.

(56) References Cited

U.S. PATENT DOCUMENTS

| | | | |
|---|---|---|---|
| 4,367,023 A | 1/1983 | Hannah et al. | |
| 4,368,023 A | 1/1983 | Hannah et al. | |
| 4,575,371 A | 3/1986 | Nordqvist et al. | |
| 4,601,713 A * | 7/1986 | Fuqua | A61M 25/0032 604/528 |
| 4,790,809 A | 12/1988 | Kuntz | |
| 5,222,949 A | 6/1993 | Kaldany | |
| 5,562,622 A | 10/1996 | Tihon | |
| 5,919,170 A | 7/1999 | Woessner | |
| 6,902,555 B2 | 6/2005 | Paskar | |
| 7,022,102 B2 | 4/2006 | Paskar | |
| 7,717,902 B2 | 5/2010 | Sauer | |
| 8,684,953 B2 | 4/2014 | Cabiri | |
| 10,918,366 B2 | 2/2021 | Lorenzo | |
| 2003/0199960 A1* | 10/2003 | Paskar | A61M 25/0041 607/122 |
| 2005/0192560 A1* | 9/2005 | Walls | A61M 25/0017 264/478 |
| 2005/0256452 A1* | 11/2005 | DeMarchi | A61M 25/0147 604/95.04 |
| 2008/0249457 A1 | 10/2008 | Li et al. | |
| 2008/0281291 A1 | 11/2008 | Tihon et al. | |
| 2011/0040290 A1 | 2/2011 | Zadini et al. | |
| 2012/0179144 A1 | 7/2012 | Carleo | |
| 2013/0304034 A1* | 11/2013 | Cabiri | A61M 25/0138 604/528 |
| 2014/0194857 A1 | 7/2014 | Eilat | |
| 2015/0297863 A1* | 10/2015 | Hannon | A61M 25/0054 427/2.3 |
| 2016/0184551 A1* | 6/2016 | Nyman | A61M 25/001 156/60 |
| 2018/0093069 A1 | 4/2018 | Bressler et al. | |
| 2021/0361910 A1 | 11/2021 | Mullins et al. | |
| 2022/0233814 A1 | 7/2022 | Mullins et al. | |

OTHER PUBLICATIONS

Badoudjian et al. article titled "Best nonsurgical managements of acute urinary retention: what's new?" Copyright © 2022 Wolters Kluwer Health, www.co-urology.com, vol. 32 ? No. 2 ? Mar. 2022 (7 pages).

Fitzpatrick et al. article titled "Management of acute urinary retention," ©The Authors Journal Compilation, ©2006 BJU International, 97, Supplement 2, 16-20 (5 pages).

Carey et al. article titled "Buckling Test as a New Approach to Testing Flexural Rigidities of Angiographic Catheters," Received Jan. 21, 2005: received Apr. 11, 2005: accepted Apr. 13, 2005, Published online Aug. 3, 2005 in Wiley InterScience (www.interscience.wiley.com) DOI: 10.1002/jbm.b.30358, https://onlinelibrary-wiley-com.laneproxy.stanford. edu/doi/pdf/10.1002/jbm.b.30358 (8 pages).

Buddha, Sandeep article titled "Complication of urethral catheterisation," www.thelancet.com, vol. 365 Mar. 5, 2005, Lancet 2005; 365: 909 (1 page).

Kim et al. article titled "CT Voiding Cystourethrography Using 16-MDCT for the Evaluation of Female Urethral Diverticula: Initial Experience," AJR:184, May 2005, Received Jun. 8, 2004; accepted after revision Sep. 9, 2004, AJR 2005;184:1594-1596 0361-803X/05/1845-1594 ©American Roentgen Ray Society (4 pages).

Carey et al. article titled "Design of Braided Composite Cardiovascular Catheters Based on Required Axial, Flexural, and Torsional Rigidities," received Jul. 17, 2003; revised Oct. 6, 2003; accepted Oct. 22, 2003, Published online Feb. 20, 2004 in Wiley InlerScience (www.interscience.wiley.com). DOI: 10.1002/jbm.b.30017 (9 pages).

Tapiero et al. article titled "Determining the Safety Threshold for the Passage of a Ureteral Access Sheath in Clinical Practice Using a Purpose-Built Force Sensor," 0022-5347/21/2062-0364/0, The Journal of Urology, https://doi.org/10.1097/JU.0000000000001719, vol. 206, 364-372, Aug. 2021 (9 pages).

Dobrowolski et al. article titled "Treatment of posterior and anterior urethral trauma," 2002 BJU International, Accepted for publication Jan. 10, 2002, BJU International (2002), 89, 752-754 (3 pages).

Marshall, MD et al. article titled "An Evidence-Based Approach To Emergency Department Management Of Acute Urinary Retention," Emergency Medicine Practice, ebmedicine.net, An Evidence-Based Approach to Emergency Medicine, Jan. 2014, vol. 16, No. 1 (24 pages).

Fakih et al. article titled "Beyond Infection: Device Utilization Ratio as a Performance Measure for Urinary Catheter Harm," Infection Control & Hospital Epidemiology Mar. 2016, vol. 37, No. 3, Downloaded from https://www.cambridge.org/core. Mar. 20, 2022 at 16:30:04 (7 pages).

U.S. Department of Health and Human Services, Food and Drug Administration, Center for Devices and Radiological Health article titled "Conventional Foley Catheters—Performance Criteria for Safety and Performance Based Pathway, Guidance for Industry and Food and Drug Administration Staff," document issued on Aug. 14, 2020, the draft of this document was issued on Sep. 19, 2019 (9 pages).

Boissier et al. article titled "Épidémiologie des urgences urologiques en France, Epidemiology of urological emergencies in France," Recu le16 juillet 2021 ; accepté le 21 juillet 2021 Disponible sur Internet le 20 août 2021, https://doi.org/10.1016/j.purol.2021.07.004, 1166-7087/© 2021 Elsevier Masson SAS.Tous droits reserves (11 pages).

Gould et al. article titled "Guideline for Prevention of Catheter-Associated Urinary Tract Infections 2009," Infection Control and Hospital Epidemiol . . . / vol. 31, No. 4, Apr. 2010 / Guideline for Prevention of Catheter-Ass . . . , https://doiorg.laneproxy.stanford.edu/10.1086/651091 (12 pages).

Hollingsworth et al., "Determining the Noninfectious Complications of Indwelling Urethral Catheters," Annals of Internal Medicine, 2013; 159: pp. 401-410; www.annals.org.

Mattelaer et al., "Catheters and Sounds: The History of Bladder Catheterisation," International Medical Society of Paraplegia, Paraplegia (1995) 33, pp. 429-433.

Kashefi et al., "Incidence and Prevention of Iatrogenic Urethral Injuries," The Journal of Urology, vol. 179, pp. 2254-2258, Jun. 2008, Divisions of Urology (Ck, JKP) and Biostatistics (KM) and Department of Nursing (RB, CS), University of California—San Diego School of Medicine, San Diego, California, USA.

Xiaoyin Ling, "Mechanical Characteristics of Male Urethral Catheterization: Simulator and Cadaveric Donor Study" A Thesis Submitted to the Faculty of the Graduate School pf the University of Minnesota; Jan. 2019; USA.

Ling et al., "A Catheter Insertion Force Assessment Tool: Design and Preclinical Results," University of Minnestoa, Department of Mechanical Engineering or Biomedical Engineering; University of Washington, Urology, 33rd EUS Annual Meeting, May 18, 2018, p. 28, San Francisco, CA.

Litwin et al., "Urologic Diseases in America Project: Analytical Methods and Principal Findings," The Journal of Urology, vol. 173, pp. 933-937, Mar. 2005, USA.

Hanna et al., "Role of MR Urethrography in Assessment of Urethral Lesions," The Egyptian Journal of Radiology and Nuclear Medicine, (Mar. 2, 2015), 46, pp. 499-505, http://creativecommons.org/licenses/by-nc-nd/4.0/, Egypt.

Labana et al., "Role of MR urethrography in detection and characterization of various urethral lesions in male patients and its comparison with conventional urethrography and Sonourethrography," MedPulse International Journal of Radiology. Mar. 2, 2020; 13(3): 114-117, http://www.medpulse.in/Radio%20Diagnosis/Department of Radio-Diagnosis, National Institute of Medical Science and Research, Jaipur, Rajasthan, India.

Murugesan et al., "Role of Magnetic Resonance Urethrography in Evaluation of Male Urethral Stricture Against Conventional Retrograde Urethrography," Journal of Clinical and Diagnostic Research, Jun. 1, 2018, vol. 12(6): TC07-TC11, India.

(56) References Cited

OTHER PUBLICATIONS

Fong et al., "Natural History and Clinical Predictors of Clinical Progression in Benign Prostatic Hyperplasia," Curr Opin Urol 15, pp. 35-38, #2005, Lippincott Williams & Wilkins, Department of Urology, University of Vienna, Vienna, Austria.
Jacobsen et al., "Natural History of Prostatism: Risk Factors for Acute Urinary Retention," The Journal of Urology, vol. 158, pp. 481-487, Aug. 1997, American Urological Association, Inc., USA.
Jain et al. "Overuse of the Indwelling Urinary Tract Catheter in Hospitalized Medical Patients," Arch Internal Med, vol. 155, pp. 1425-1429, Jul. 10, 1995, From the Department of Medicine, State University of New York Health Science Center, New York, USA.
Kang et al. "Retrograde CT Urethrography Using a Power Injector Quantitatively Reveals Effects of Bladder Distension on Urethral Size in Healthy Male Beagle Dogs," Vet Radiol Ultrasound, 2020, vol. 61, pp. 302-311, https://doi.org/10.1111/vru.12849.
Saint et al., "Are Physicians Aware of Which of Their Patients Have Indwelling Urinary Catheters," American Journal of Medicine, vol. 109, pp. 476-480, Oct. 15, 2000, USA.
Saint et al., "A Multicenter Study of Patient-Reported Infectious and Noninfectious Complications Associated with Indwelling Urethral Catheters," Jama Internal Medicine, Jul. 2, 2018, 178(8), pp. 1078-1085, jamainternalmedicine.com.
Sellett, "Iatrogenic Urethral Injury Due to Preinflation of a Foley Catheter," Jama Internal Medicine, Sep. 13, 1971, vol. 217, No. 11, p. 1549.
Choudhary et al., "A Comparison of Sonourethrography and Retrograde Urethrography in Evaluation of Anterior Urethral Strictures," Clinical Radiology Jan. 27, 2004, 59, pp. 736-742.
Garcia-Matres et al., "A Foley Type Catheter with a Steerable Tip," Archivos Espanoles de Urologia, vol. 45, No. 4, May 1992, pp. 299-303, Spain.
Bianchi et al., "Difficult Foley Catheterization," Statpearls Publishing LLC, Nov. 7, 2021, Bookshelf ID: NBK564404PMID.
Kohler et al., "The Length of the Male Urethra," Int Braz J Urol, Clinical Urology, vol. 34 (4), pp. 451-456, Jul.-Aug. 2008, Alexandria, Egypt.
Thomas et al., Avoidable Iatrogenic Complications of Urethral Catheterization and Inadequate Intern Training in a Tertiary-Care Teaching Hospital, BJU International, vol. 104, pp. 1109-1112, Department of Urology and Renal Transplantation, Beaumont Hospital, Royal College of Surgeons in Ireland, Dublin, Ireland.
Thomas et al., "Acute Urinary Retention: What Is the Impact in Patients' Quality of Life," Jul. 30, 2004, BJU International, vol. 95, pp. 72-76, Urology Department, St. Geourge's Hospital, London, UK.
Safdari et al., "Practical, Noninvasive Measurement of Urinary Catheter Insertion Forces and Motions," Proceedings of the 2019 Design of Medical Devices Conference, DMD2019-3308, pp. 1-5, Apr. 15-18, 2019, Minneapolis, MN, USA.
Newman et al., "Unseen Perils of Urinary Catheters," Jun. 1, 2015, Agency for Healthcare Research and Quality (AHRQ), U.S. Department of Health and Human Services, USA.
Selius et al., "Urinary Retention in Adults: Diagnosis and Initial Management," American Family Physician, Mar. 1, 2008, vol. 77, No. 5, pp. 644-650, USA, www.aafp.org/afp.
Kaler et al., "Ureteral Access Sheath Deployment: How Much Force is Too Much," Experimental Endourology, Journal of Endourology, vol. 33, No. 9, Sep. 2019, pp. 712-718 USA.
Canales et al., "Urethral Catheter Insertion Forces: A Comparison of Experience and Training," Investigative Urology, International Braz J Urol, vol. 35, No. 1, pp. 84-89, Jan.-Feb. 2009.
Bregman et al., "Urethral Trauma After Foley Catheter Placement," American Medical Association, Jama Internal Medicine, Nov. 2016, vol. 176, No. 11, pp. 1606-1607.
Villanueva et al., "Difficult Male Urethral Catheterization: A Review of Different Approaches," International Braz J Urol vol. 34, No. 4, pp. 401-412, Jul.-Aug. 2008.
Villanueva et al., "The Approach to the Difficult Urethral Catheterization Among Urology Residents in the United States," International Braz J Urol, vol. 36, No. 6, pp. 710-717, Nov.-Dec. 2010.
Wei et al., "Urologic Diseases in America Project: Benign Prostatic Hyperplasia," The Journal of Urology, vol. 173, pp. 1256-1261, Apr. 2005, USA.
Willette et al., "Current Trends in the Management of Difficult Urinary Catheterizations," Western Journal of Emergency Medicine, vol. 13, No. 6, 2012, University of California, USA.
Wu et al., "National Incidence and Outcomes of Postoperative Urinary Retentionin the Surgical Care Improvement Project," The American Journal of Surgery (2012) vol. 204, pp. 167-171.
Clarebrough et al. article titled "CATCH-22: a manual bladder washout protocol to improve care for clot retention," Received: Jan. 31, 2018 / Accepted: May 17, 2018 / Published online: May 28, 2018, World Journal of Urology (2018) 36:2043-2050, https://doi.org/10.1007/s00345-018-2346-z (8 pages).
Leuck et al. article titled "Complications of Foley Catheters—Is Infection the Greatest Risk?", 0022-5347/12/1875-1662/0, The Journal of Urology, © 2012 by American Urological Association Education and Research, Inc., vol. 187, 1662-1666, May 2012, DOI:10.1016/j.juro.2011.12.113 (5 pages).
Aaronson et al. article titled "National Incidence and Impact of Noninfectious Urethral Catheter Related Complications on the Surgical Care Improvement Project," 0022-5347/11/1855-1756/0, The Journal of Urology, © 2011 by American Urological Association Education Ano Research, Inc., vol. 185, 1756-1760, May 2011, D01:10.1016/j.juro.2010.12.04 (5 pages).
Wu et al. article titled "National incidence and outcomes of postoperative urinary retention in the Surgical Care Improvement Project," The American Journal of Surgery, vol. 204, No. 2, Aug. 2012, http://dx.doi.org/10.1016/j.amjsurg.2011.11.012 (5 pages).
Wagner et al. article titled "Urinary Catheterization: a Paradigm Shift in Difficult Urinary Catheterization," Men's Health, DOI 10.1007/s 11934-016-0641-z. Published online: Sep. 24, 2016 (7 pages).
International Search Report re PCT/US22/30962 dated Oct. 4, 2022 (4 pages).
Written Opinion re PCT/US22/30962 dated Oct. 4, 2022 (11 pages).

\* cited by examiner

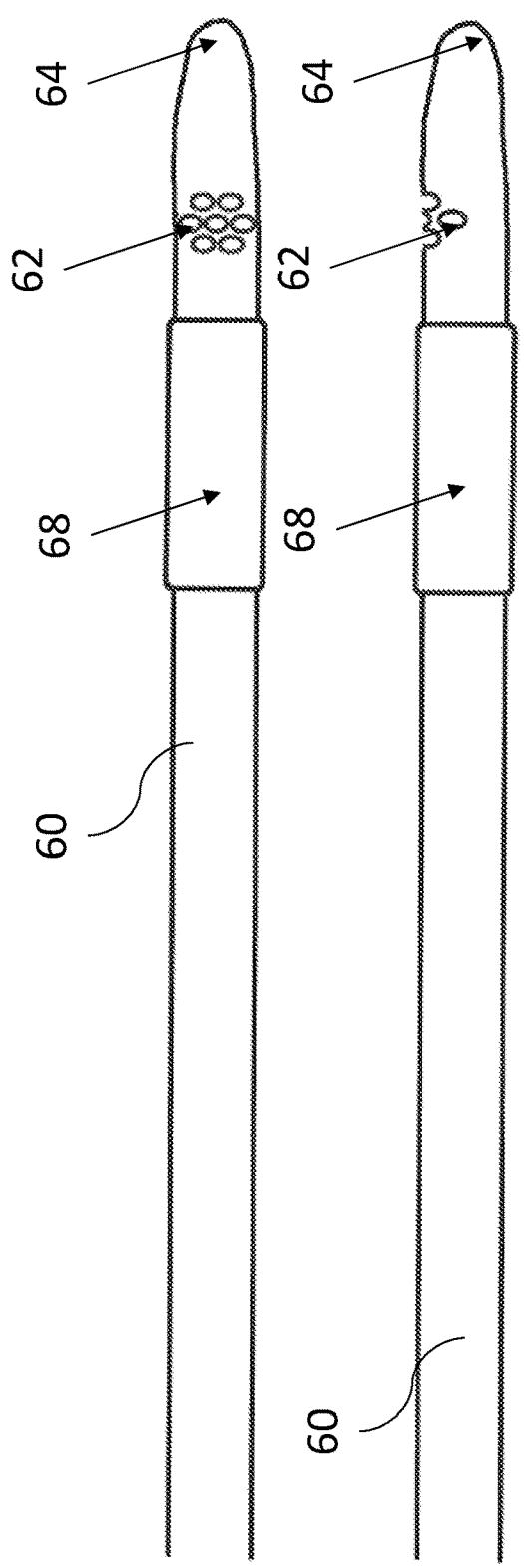
FIG. 6A
FIG. 6B
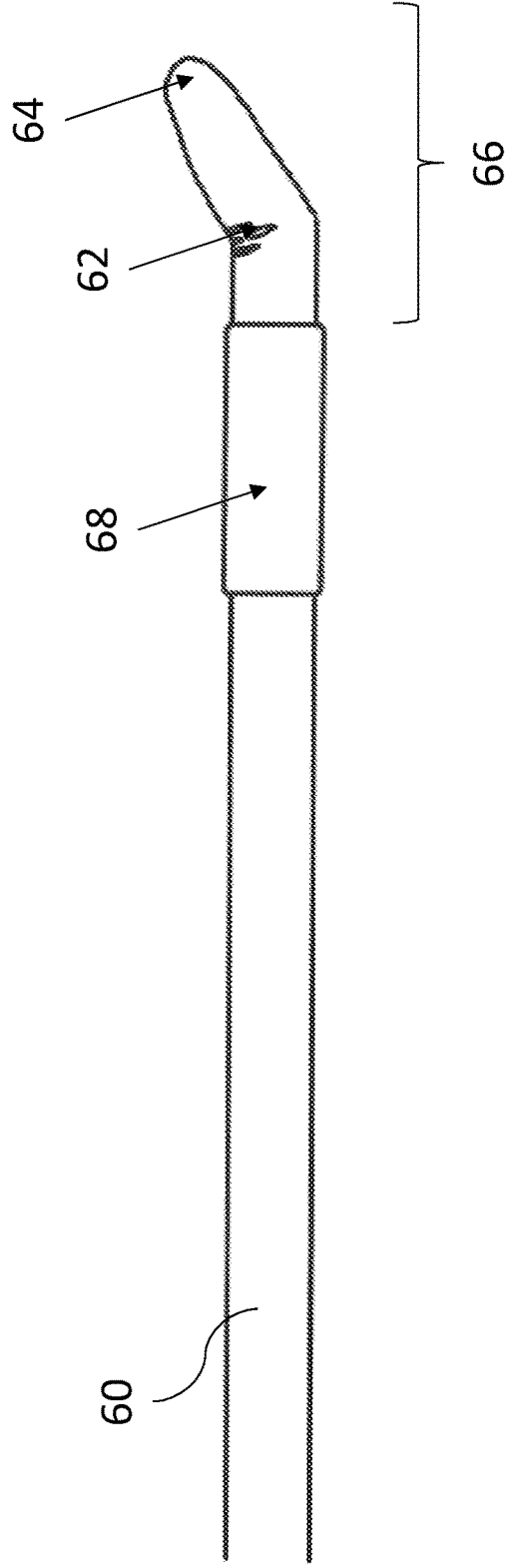
FIG. 6C

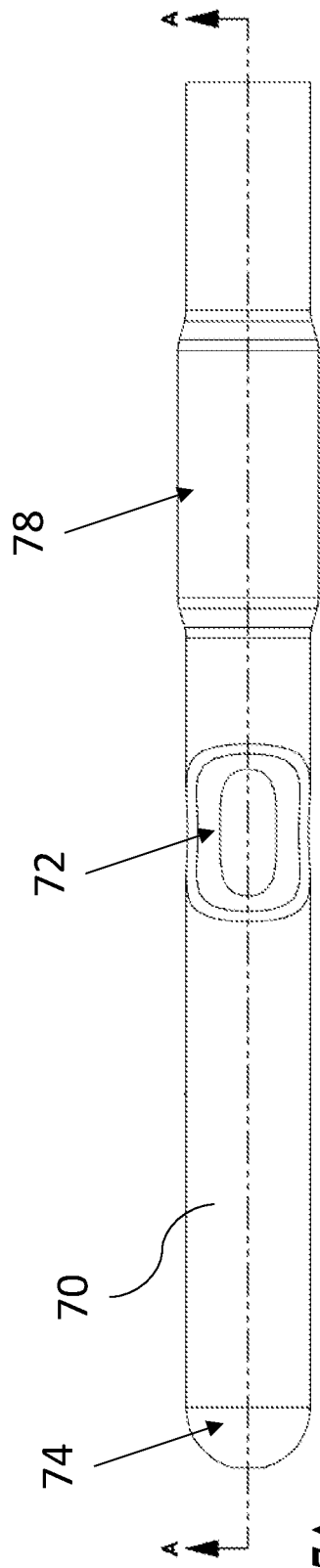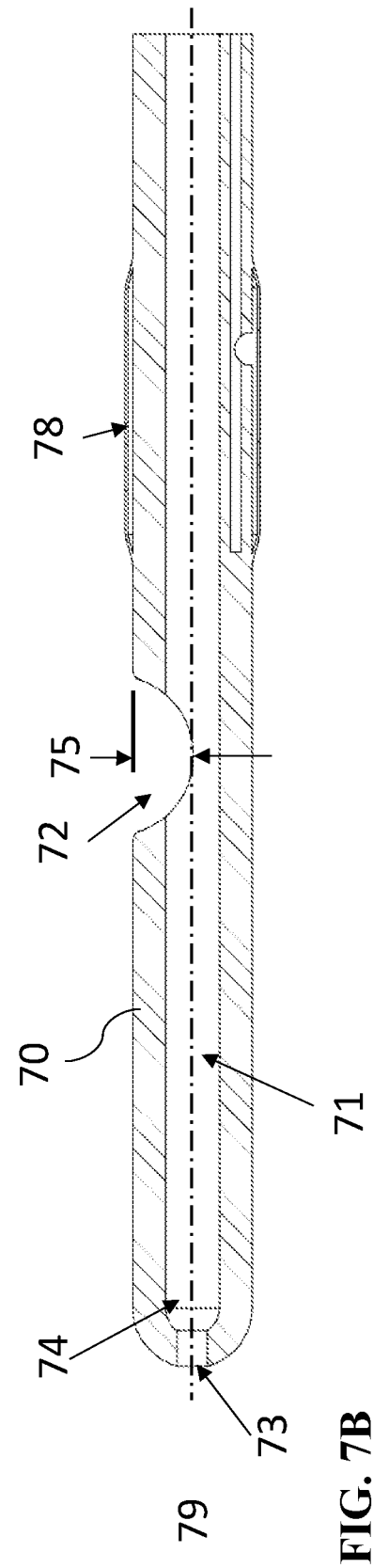
FIG. 7A
FIG. 7B

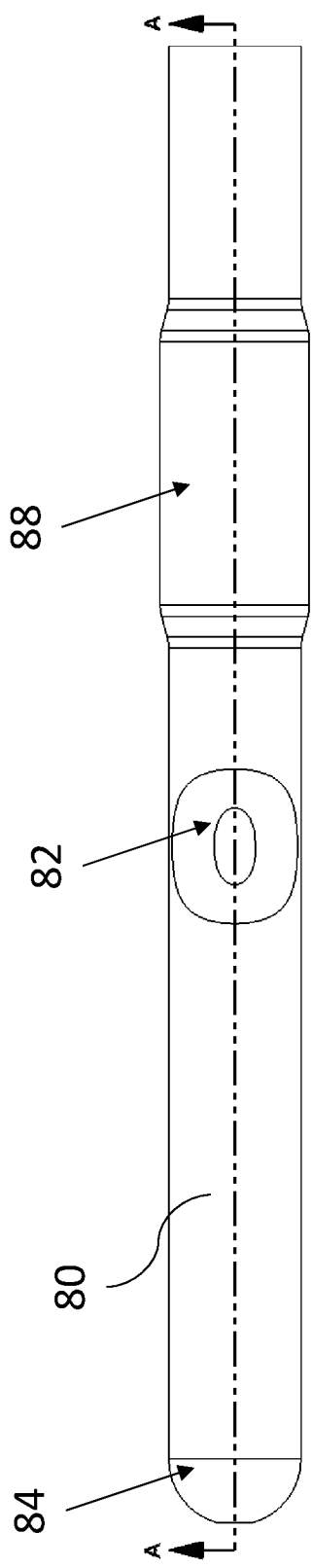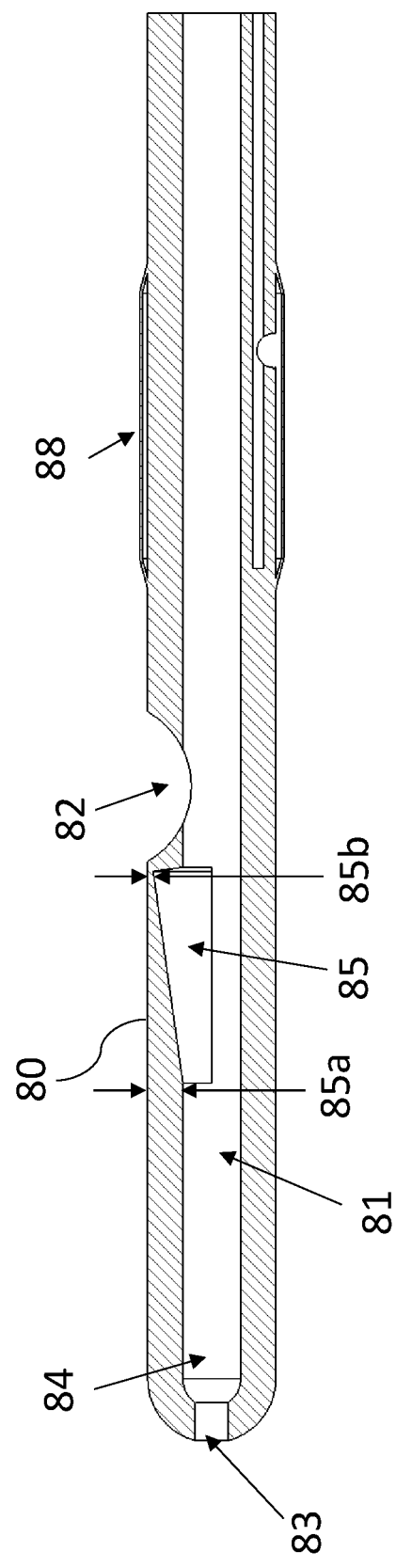
FIG. 8A
FIG. 8B

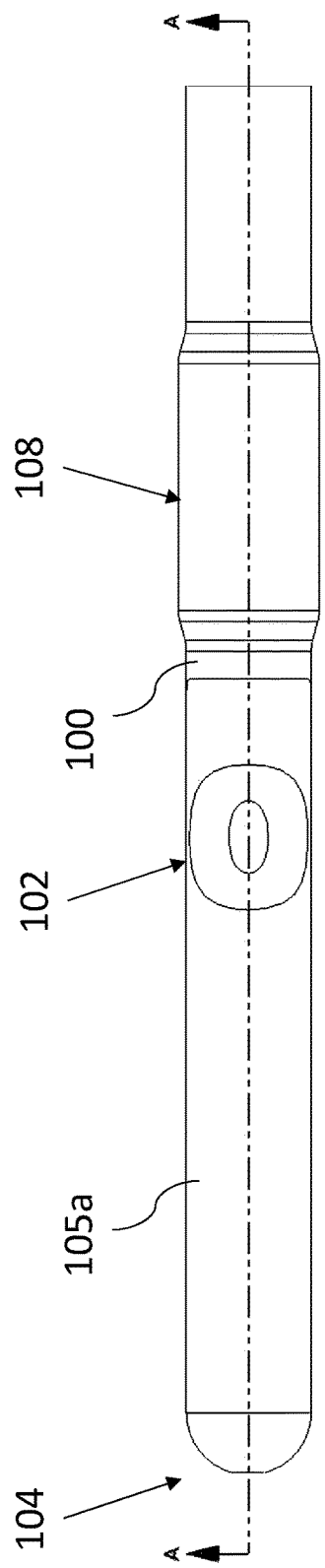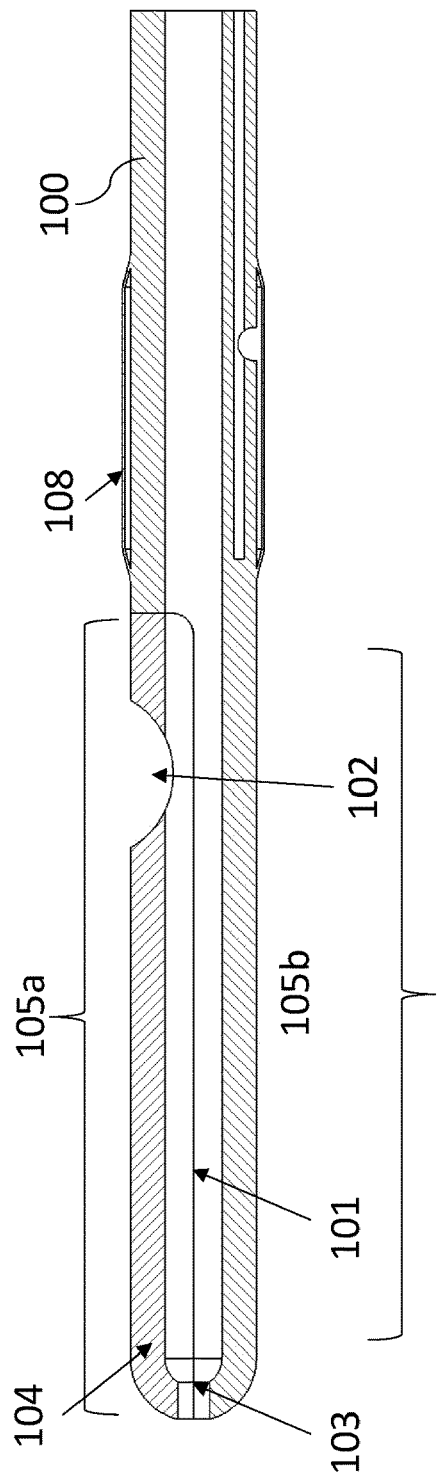
FIG. 10A
FIG. 10B

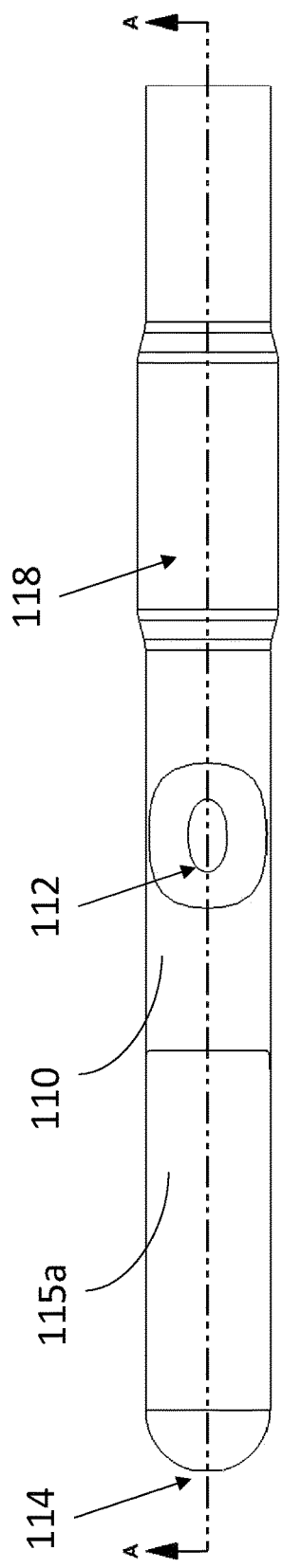
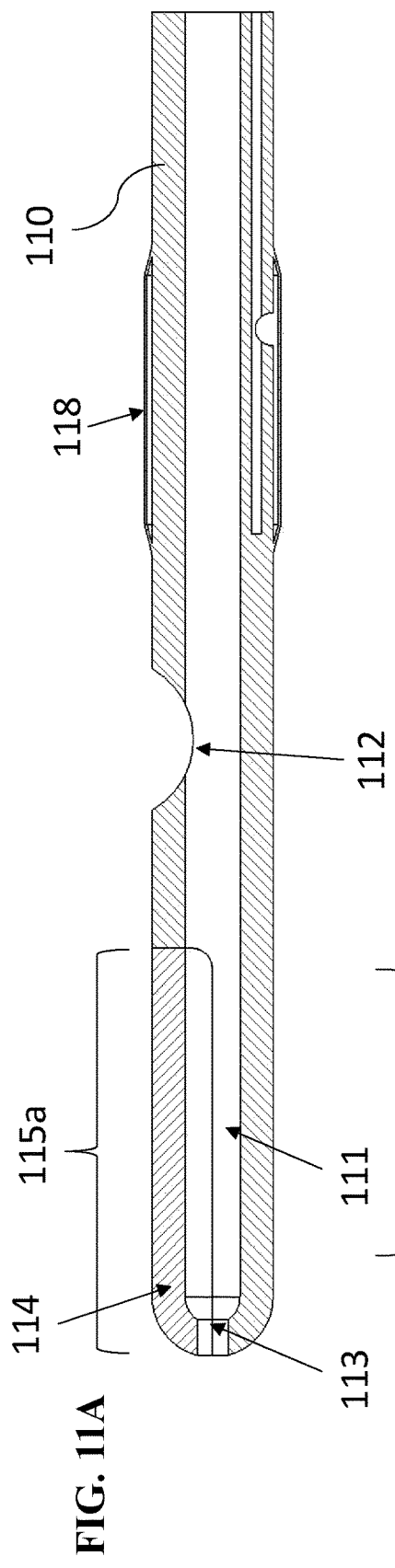
FIG. 11A
FIG. 11B

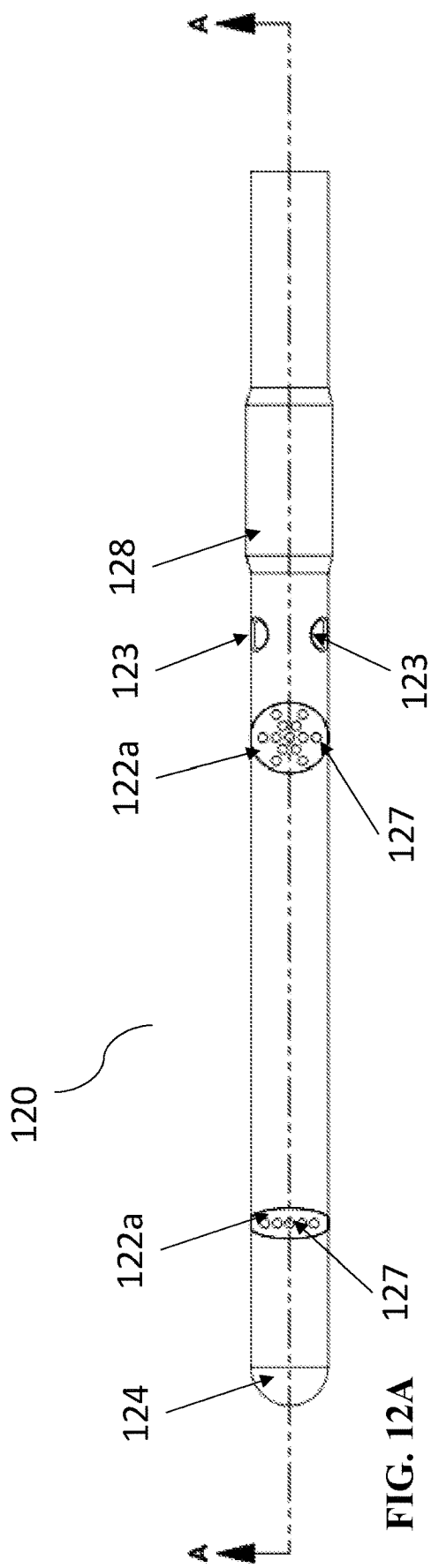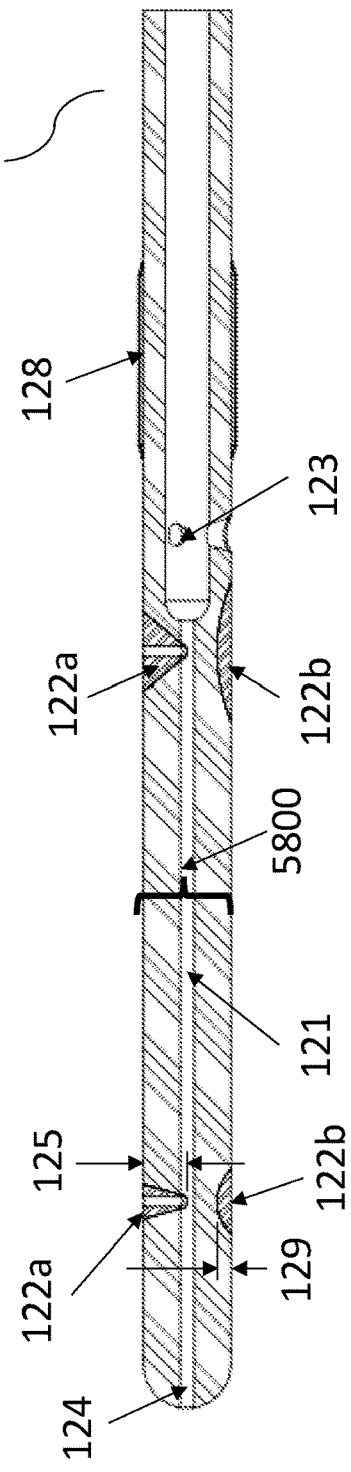
FIG. 12A
FIG. 12B

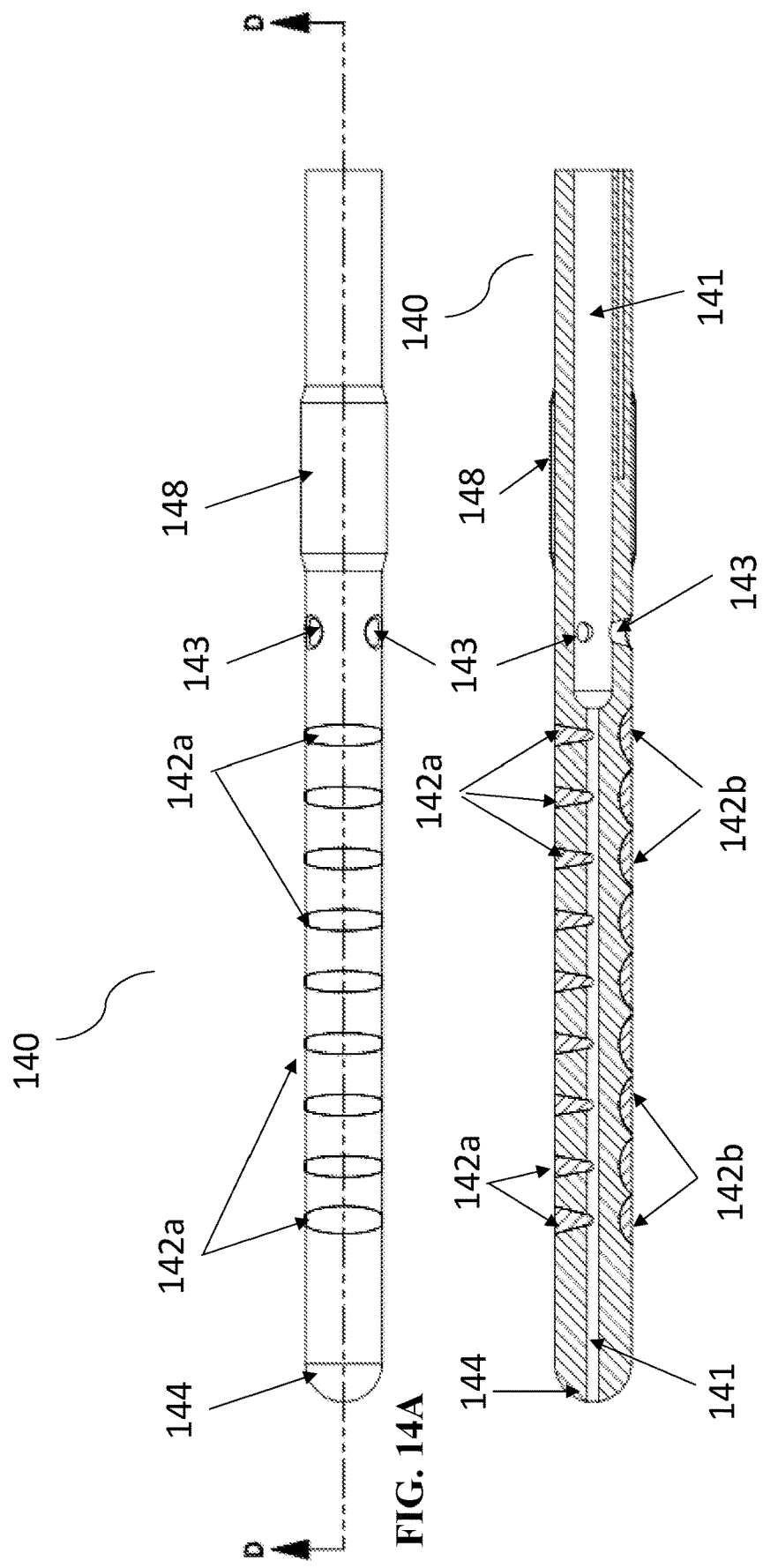

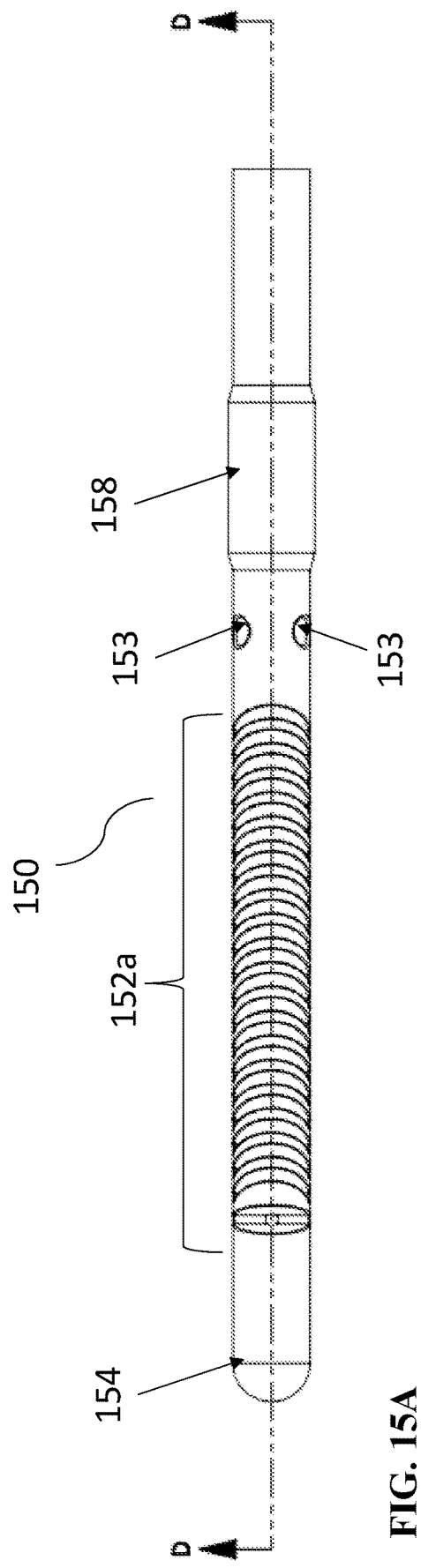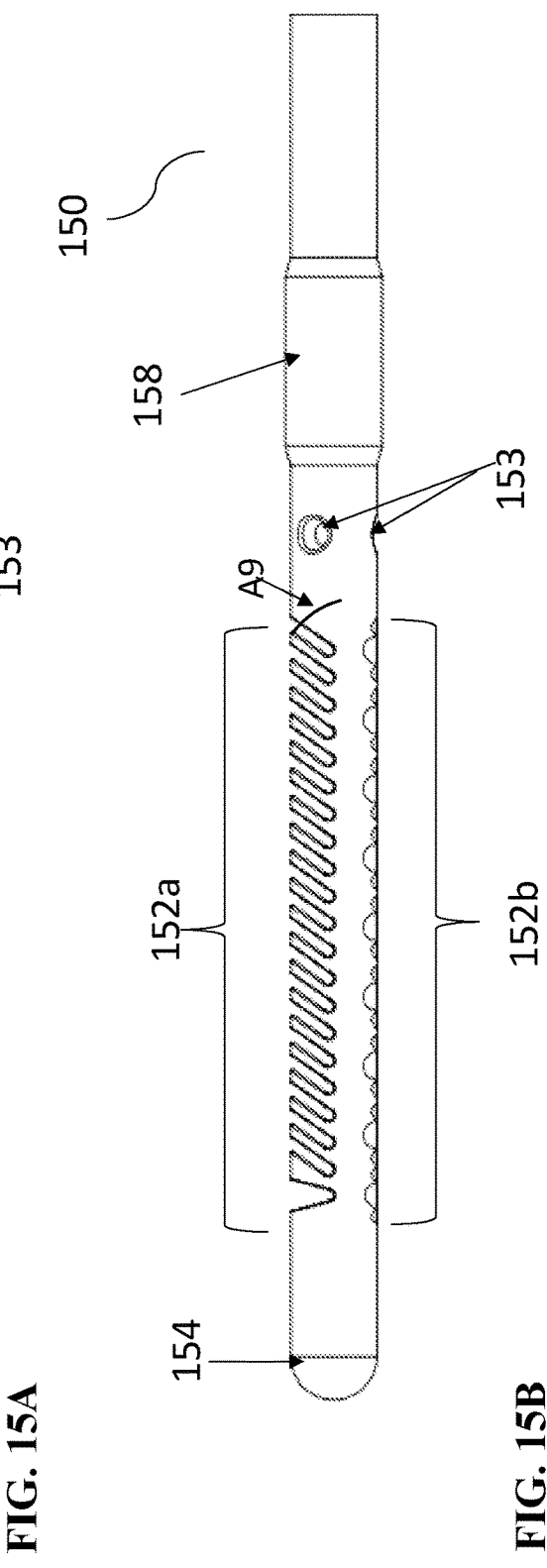
FIG. 15A
FIG. 15B

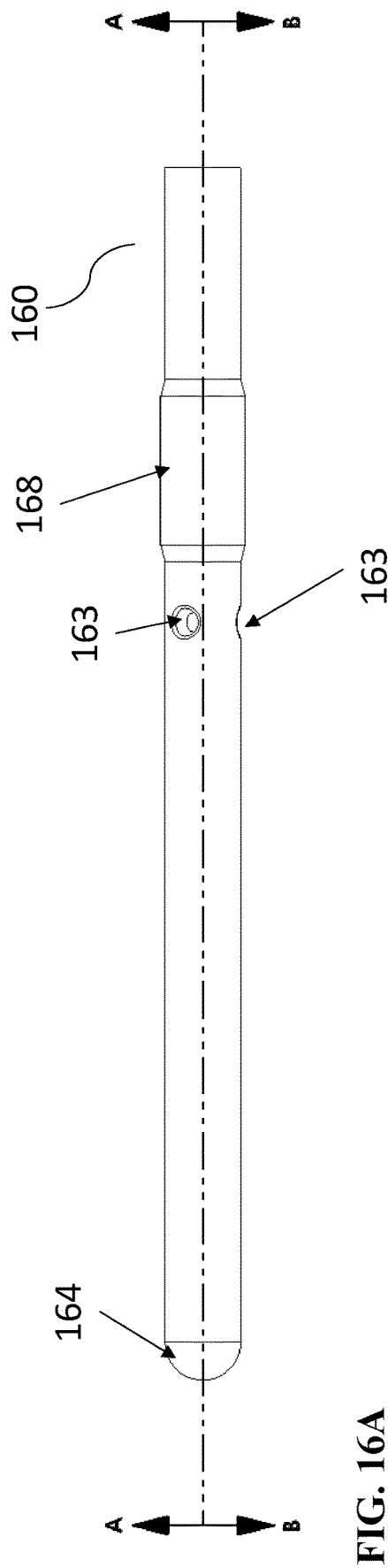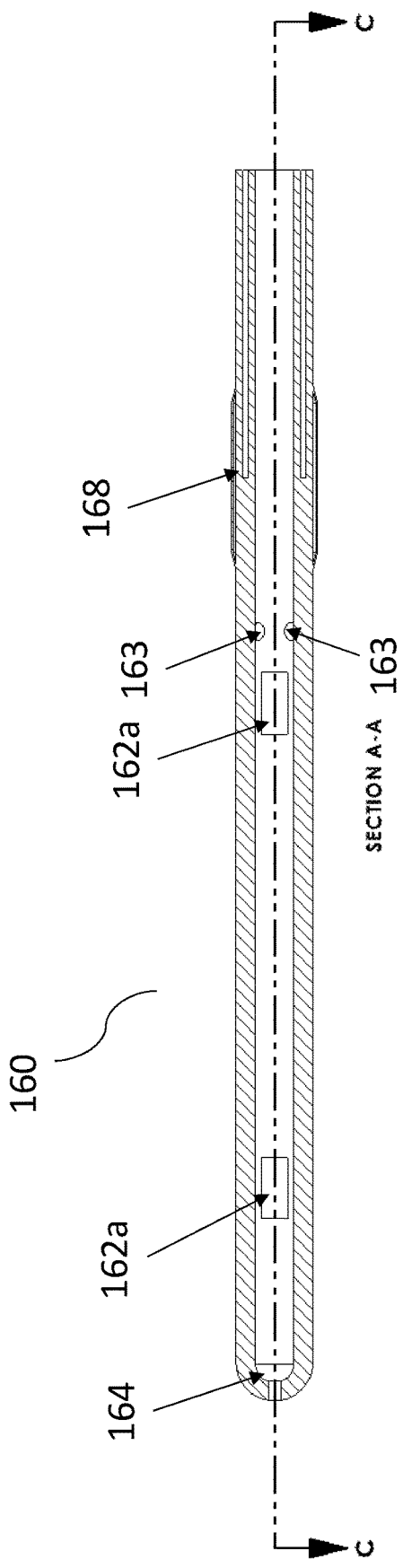
FIG. 16A
FIG. 16B

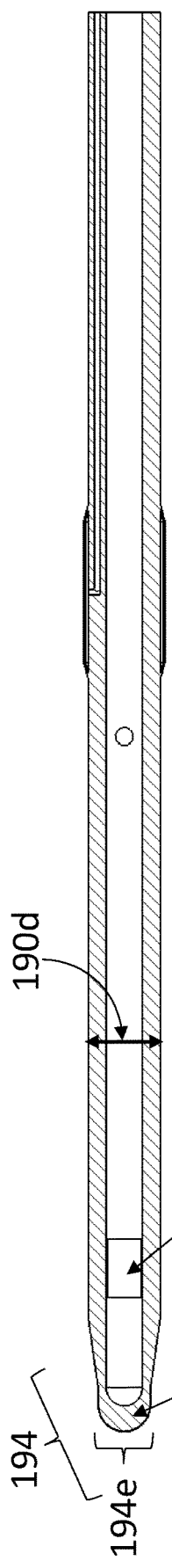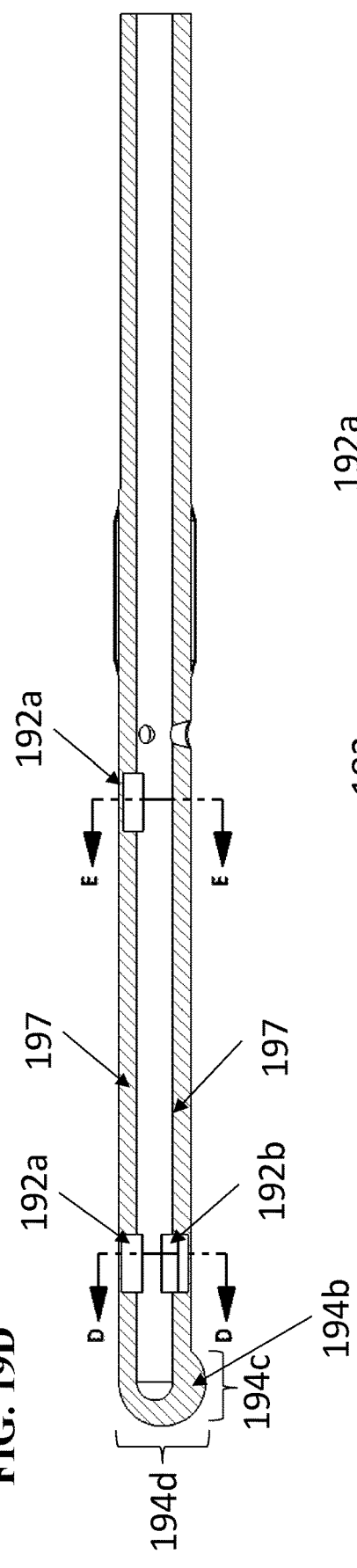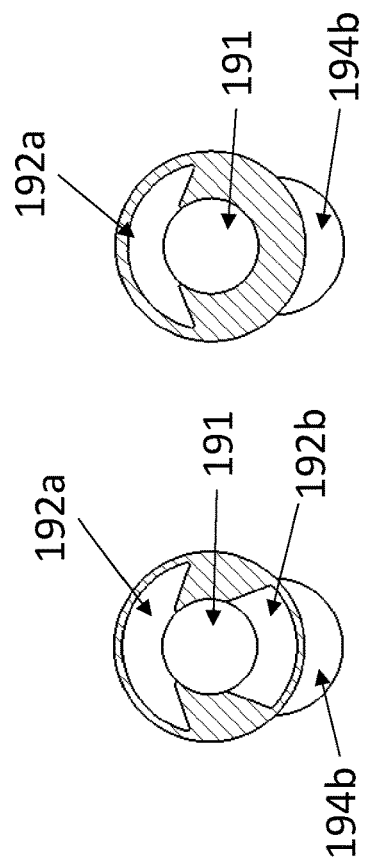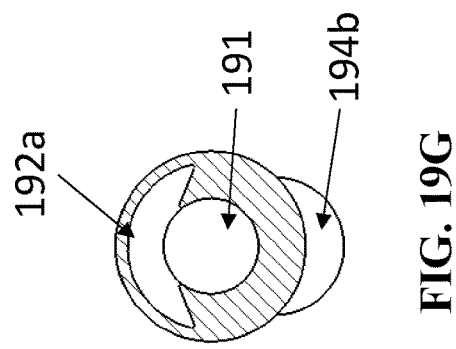

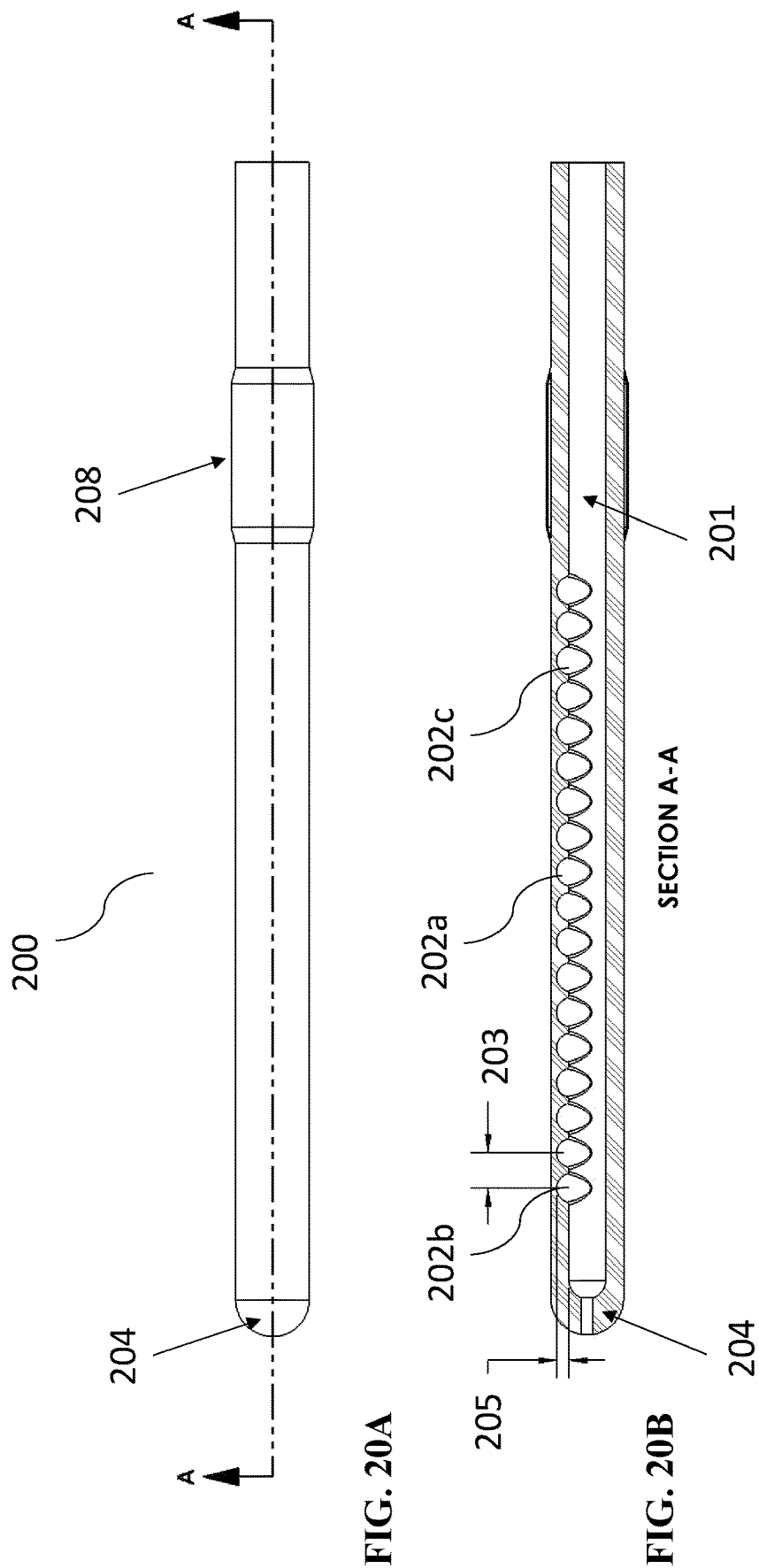

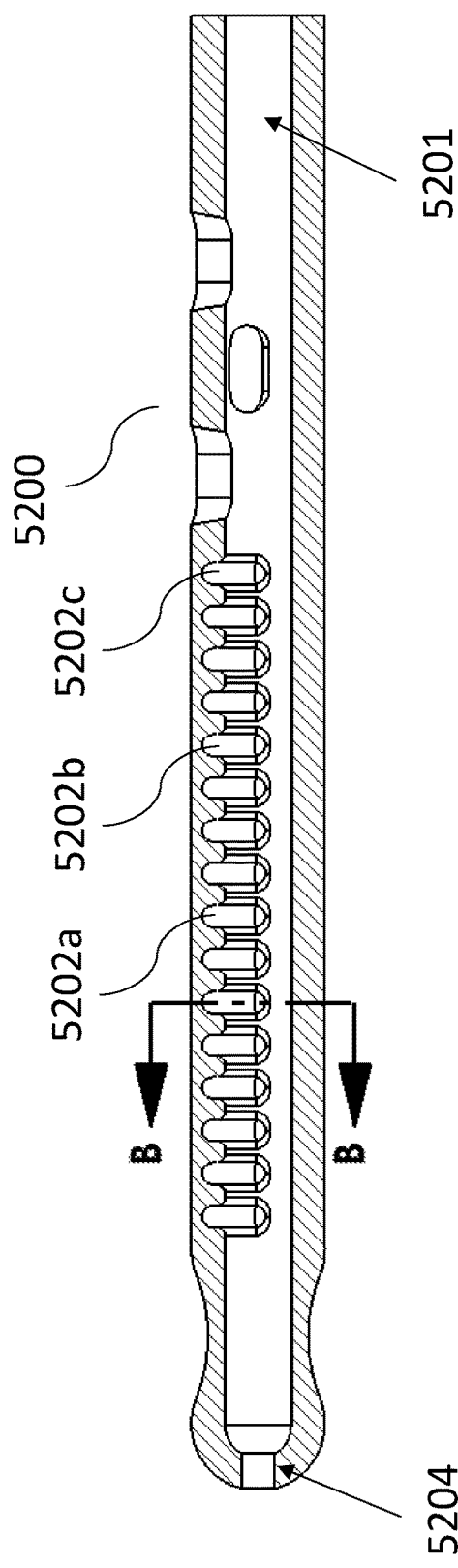
FIG. 20C
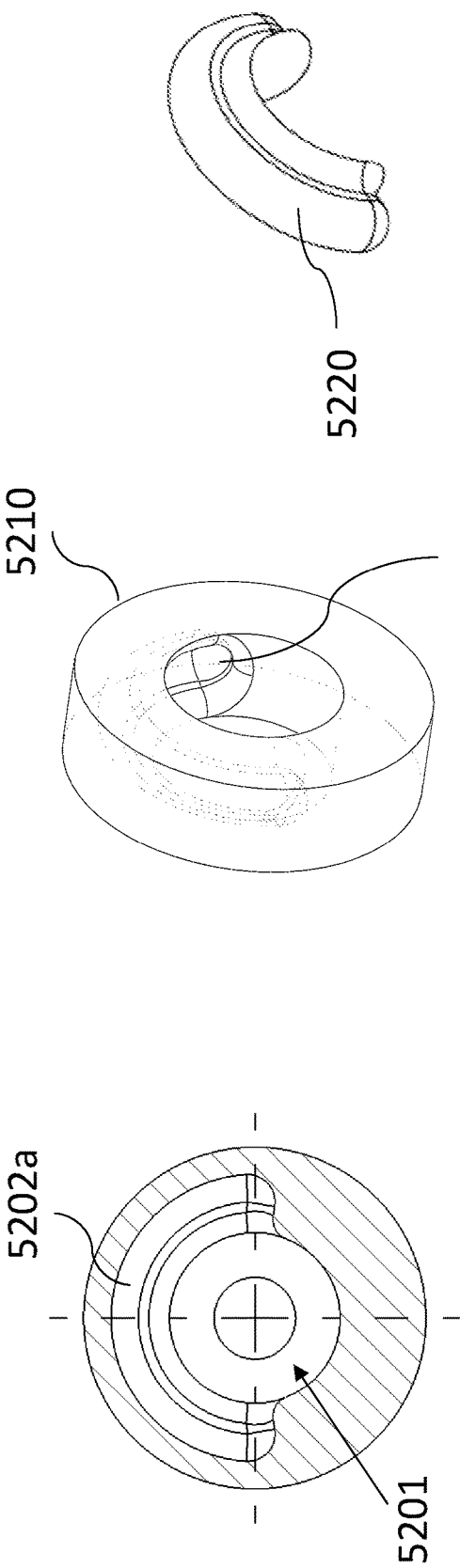
FIG. 20E
FIG. 20F
FIG. 20D

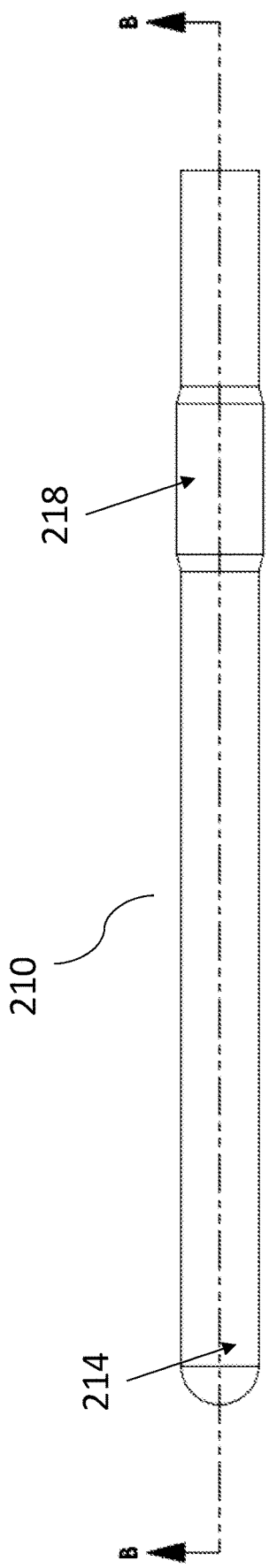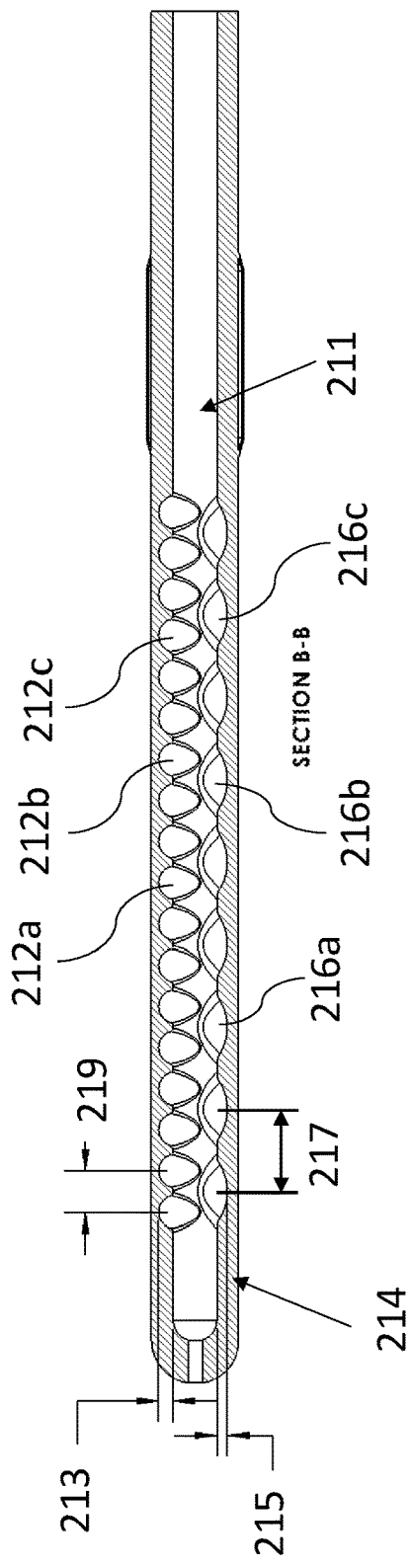
FIG. 21A
FIG. 21B

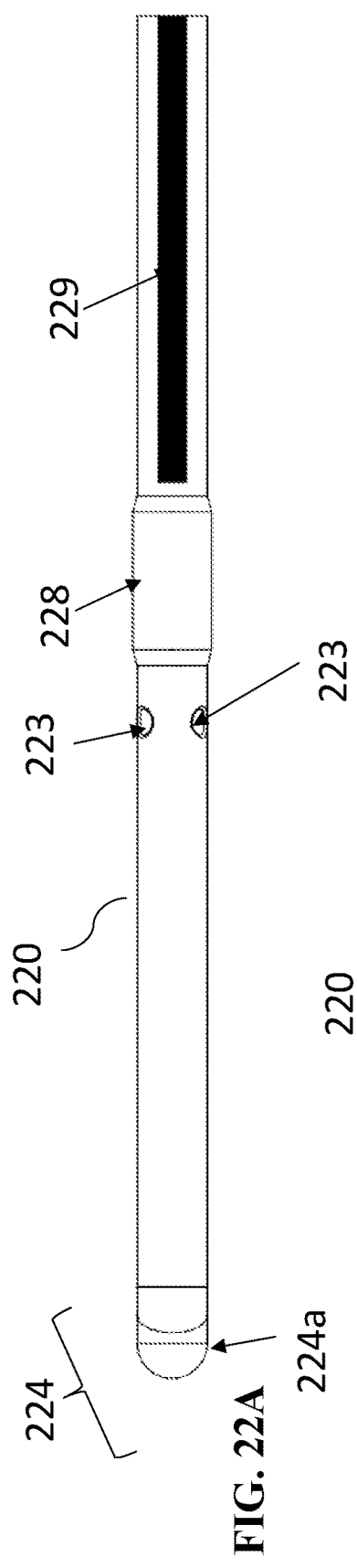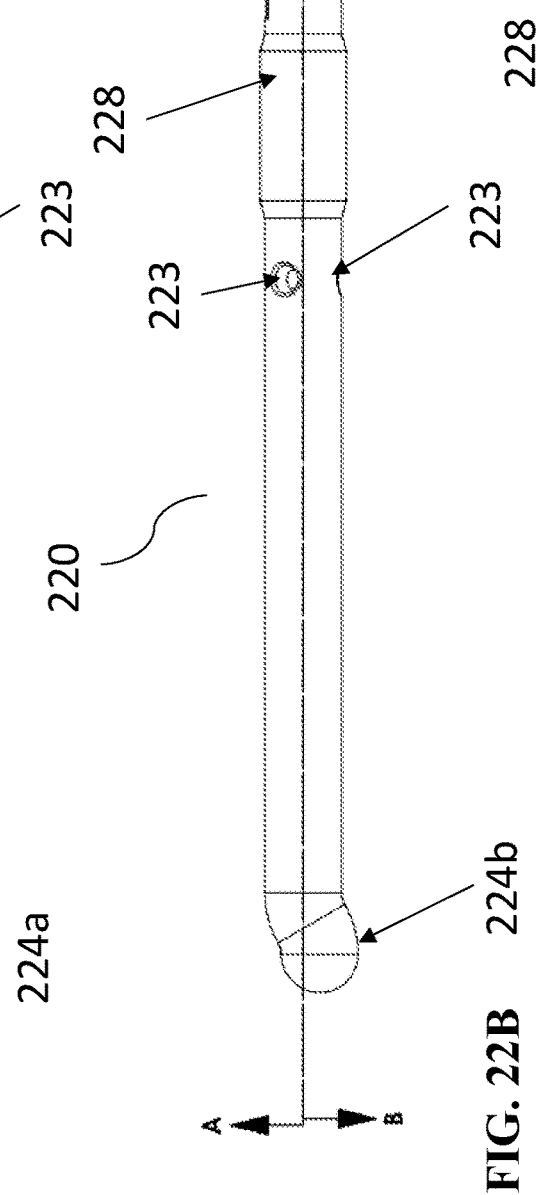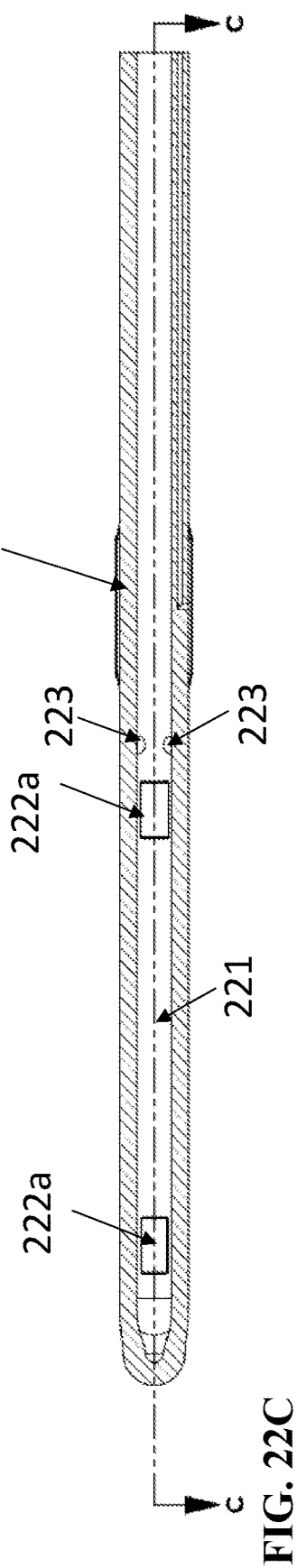
FIG. 22A
FIG. 22B
FIG. 22C

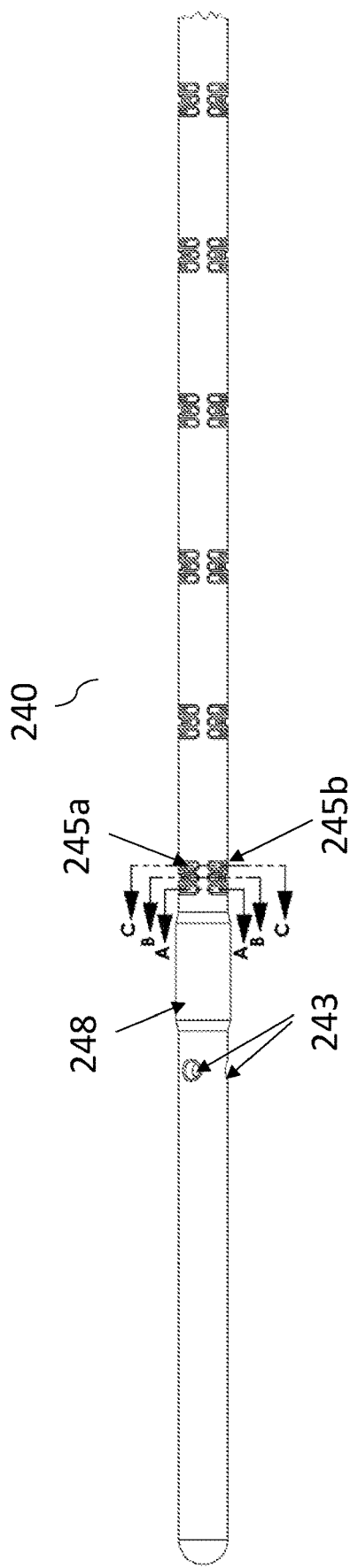
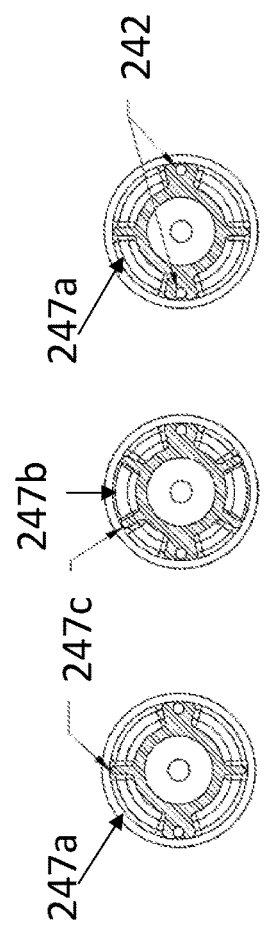
FIG. 24A
FIG. 24B  FIG. 24C  FIG. 24D

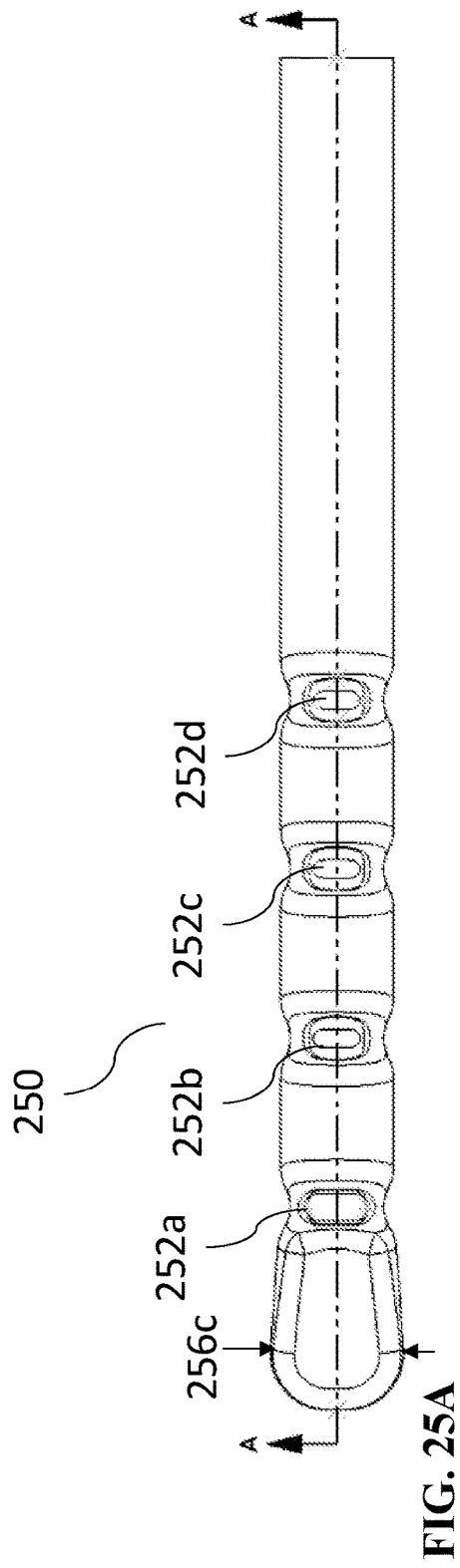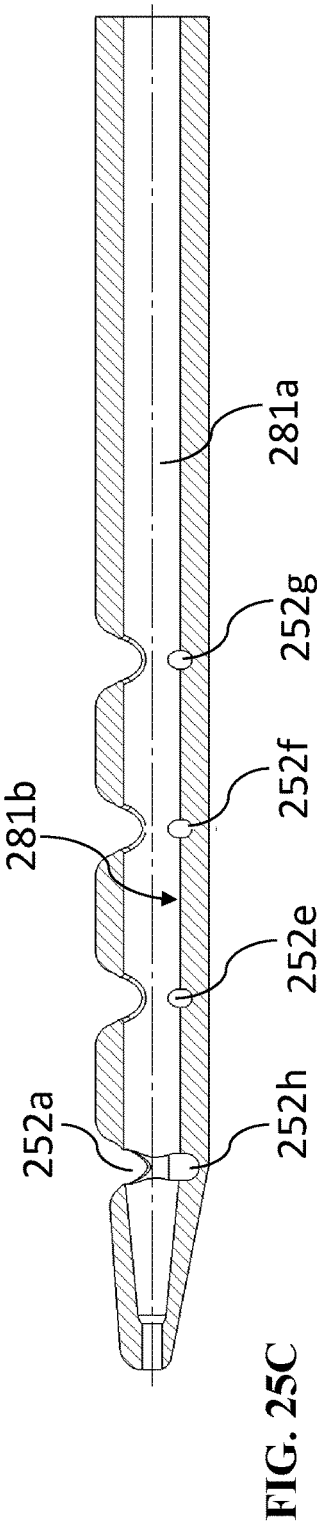
FIG. 25A
FIG. 25B
FIG. 25C

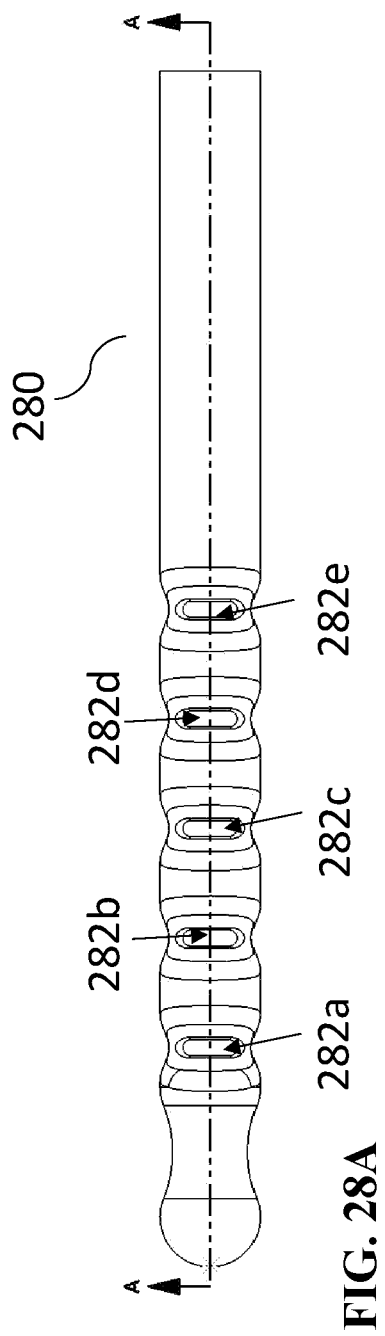
FIG. 28A
FIG. 28B
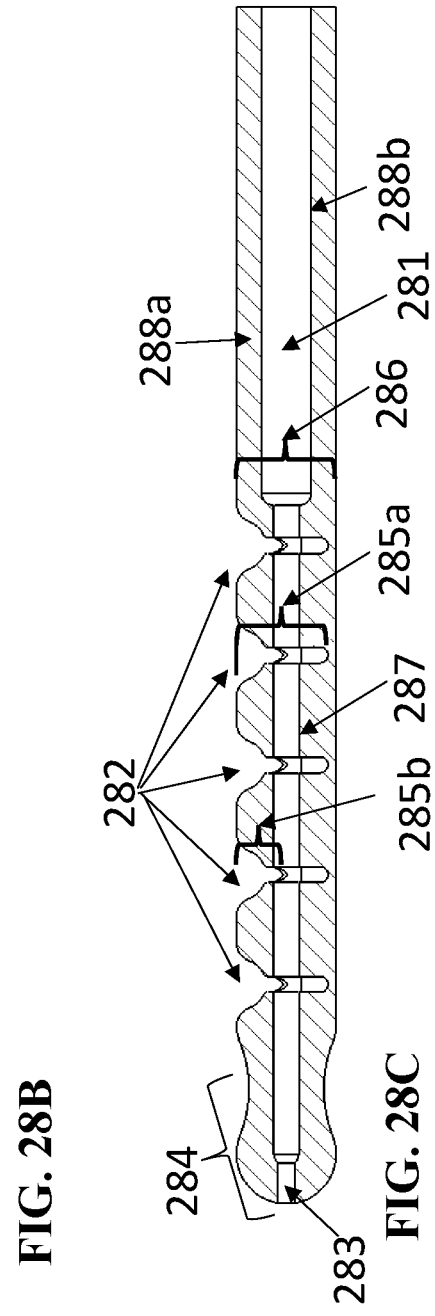
FIG. 28C

FLEXIBLE CATHETERS AND RELATED METHODS

CROSS-REFERENCE TO RELATED APPLICATIONS

This application is a continuation of International Patent Application, under the Patent Cooperation Treaty, Ser. No. PCT/US2022/030962, filed May 25, 2022; which claims the priority benefit of U.S. Provisional Patent Application Ser. No. 63/193,228, filed May 26, 2021, the contents of each of which are herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of catheterization, and more specifically to the field of urology. Described herein are flexible catheters and related methods for improving catheterization in bodily lumen, for example the urinary tract, nasopharynx, gastrointestinal tract, neurological vessels, etc.

BACKGROUND

Practitioners use a number of different catheters to perform different functions in the acute and chronic care setting. Common indications for placing a urinary catheter in a patient include: 1) acute or chronic urinary retention (e.g., benign prostatic hypertrophy, atonic bladder, neurogenic bladder, etc.); 2) urine output measurements; 3) incontinence; and 4) patients status post bladder or prostate surgery. The catheters that may be used include Foley catheters, Robinson catheters, Coudé® catheters, etc.

For example, indwelling catheters (also known as Foley catheters) are configured to be positioned in the urethra for long periods of time. A Foley catheter is provided at its tip with an inflatable balloon, which secures the catheter in position within the bladder, reducing the likelihood of expulsion from the bladder. In other situations, a Robinson catheter or intermittent catheter, may be used for short term drainage of urine from the bladder. Unlike the Foley catheter, it has no balloon on its tip and therefore cannot self-anchor. Further, as another option, a Coudé® catheter may be used, which has a curved tip with or without a balloon (as described above), the purpose of which is to facilitate its insertion through urethral canal strictures or prostatic urethra obstructions, such as in the case of benign prostatic hypertrophy. Additionally, or alternatively, a catheter may comprise a temperature probe thereon or one or more irrigation lumens to carry irrigation fluid (e.g., chemo, saline, rinse, etc.) into the bladder. It is mostly used to irrigate the bladder in case of hematuria with or without presence of clots within the bladder.

Not only do the wide variety of adult catheters create confusion for hospital staff for which one should be used when, but most common adult urinary catheters come in a variety of diameters, for example 12 F (4 mm) to 30 F (10 mm).

If a catheter is not placed properly, there are various complications that can develop. For example the complications from catheter associated trauma include: bleeding (gross hematuria), urethral injury (e.g., urethral stricture, creation of false passage, difficulties with future catheterization, etc.), potentially sexual side effects as erectile bodies (i.e., corpus cavernosa) that run close and lateral to urethra, Peyronie's disease (i.e., abnormal curvature of the penis from scarring on tunica albuginea layer of erectile bodies), urinary tract infections, and urinary retention.

Further, the wide variety of catheters and their associated different sizes often results in confusion and/or placement of multiple catheters for one patient or one indication, resulting in excessive medical waste, redundancy, and workflow disruptions.

Accordingly, there is a need for universal catheters that are safe, effective, and not confusing, while also minimizing medical waste and workflow disruptions.

SUMMARY

One aspect of the present disclosure is directed to a catheter comprising: an elongate body having a proximal segment and a distal segment; a first lumen defined by the elongate body and configured for drainage of a liquid from a bodily region; and a plurality of flexibility regions on or in the distal segment of the elongate body. In any of the preceding embodiments, the plurality of flexibility regions is configured to passively bend anteriorly when advanced through a curved pathway.

In any of the preceding embodiments, a cut depth percentage of at least one of the plurality of flexibility regions is about 50% to about 75% of a wall thickness of the elongate body.

In any of the preceding embodiments, a percent volume removed from at least one of the plurality of flexibility regions is about 15% to about 20%.

In any of the preceding embodiments, a force to bend a flexibility region is less than the force to bend a portion of the elongate body that does not include any of the plurality of flexibility regions. In any of the preceding embodiments, a force to bend the distal segment anteriorly is less than the force to bend the distal segment posteriorly.

In any of the preceding embodiments, a percent of volume removed from at least one of the plurality of flexibility regions is about 15% to about 20%. In any of the preceding embodiments, a percent of volume removed from at least one of the plurality of flexibility regions is about 25% to about 35%.

In any of the preceding embodiments, at least a subset of the plurality of flexible regions has a combined bending angle of about 30 degrees to about 200 degrees.

In any of the preceding embodiments, the catheter is a urinary catheter. In any of the preceding embodiments, the bodily region comprises one of: a tissue, an organ, a vessel, or a cavity.

In any of the preceding embodiments, at least a subset of the plurality of flexibility regions extends into the first lumen and further functions as a drainage port. In any of the preceding embodiments, the catheter further comprises a retention balloon disposed about at least a portion of the distal segment of the elongate body. In any of the preceding embodiments, the catheter further comprises a second lumen configured for inflation of the retention balloon.

In any of the preceding embodiments, a cut depth percentage of one or more of the plurality of flexibility regions is about 40% to about 50% of an outer diameter of the elongate body. In any of the preceding embodiments, a cut depth percentage of one or more of the plurality of flexibility regions is about 51% to about 67% of an outer diameter of the elongate body.

In any of the preceding embodiments, at least a subset of the plurality of flexibility regions has a cut length percentage of about 10% to about 90%. In any of the preceding embodiments, the cut length percentage is about 70% to about 80%.

In any of the preceding embodiments, the plurality of flexibility regions comprises more than two flexibility regions. In any of the preceding embodiments, the plurality of flexibility regions comprises three to five flexibility regions.

In any of the preceding embodiments, a durometer of the elongate body is between about 20 Shore A to about 80 Shore A. In any of the preceding embodiments, the durometer of the elongate body is between about 40 Shore A to about 70 Shore A.

In any of the preceding embodiments, a length of the distal segment is about 1 cm to about 10 cm.

In any of the preceding embodiments, the length of the distal segment is about 3 cm to about 5 cm.

In any of the preceding embodiments, a ratio of outer diameter of the elongate body to an outer projected thickness of a distal tip of the distal segment is about 1.0:0.8 to about 1.0:0.2.

In any of the preceding embodiments, one or more of the plurality of flexibility regions extends through an anterior sidewall of the elongate body through the first lumen and into a luminal surface of a posterior sidewall of the elongate body.

In any of the preceding embodiments, one or more of the plurality of flexibility regions extends through an anterior sidewall of the elongate body, circumferentially about at least a portion of the first lumen and into a luminal surface of a posterior sidewall of the elongate body.

In any of the preceding embodiments, a distal most flexibility region of the plurality of flexibility regions has a cut depth percentage that is greater than the subset of the plurality of flexibility regions.

In any of the preceding embodiments, the cut depth percentage of the distal most flexibility region is about 80% to about 95% of an outer diameter of the elongate body.

In any of the preceding embodiments, at least a portion of the elongate body has a polygonal shape. In any of the preceding embodiments, the polygonal shape is a trapezoidal prism.

In any of the preceding embodiments, the plurality of flexibility regions comprises an anterior plurality of flexibility regions. In any of the preceding embodiments, the catheter further comprises a posterior plurality of flexibility regions.

In any of the preceding embodiments, the posterior plurality of flexibility regions each comprise a groove in an inner sidewall of the first lumen of elongate body. In any of the preceding embodiments, the grooves in the inner sidewall of the first lumen has a cut depth percentage of 5% to about 20% of the wall thickness.

Another aspect of the present disclosure is directed to a catheter comprising: an elongate body having a proximal segment and a distal segment; a first lumen defined by the elongate body and configured for drainage of a liquid from a bodily region; and at least one flexibility region on or in the distal segment of the elongate body.

In any of the preceding embodiments, the at least one flexibility region is configured to bend anteriorly at an absolute bending angle of about 20 degrees to about 200 degrees.

In any of the preceding embodiments, the at least one flexibility region has a cut depth percentage of about 30% to about 70% of an outer diameter of the elongate body.

In any of the preceding embodiments, the catheter is a urinary catheter. In any of the preceding embodiments, the bodily region comprises one of: a tissue, an organ, a vessel, or a cavity.

In any of the preceding embodiments, the at least one flexibility region extends into the first lumen and further functions as a drainage port.

In any of the preceding embodiments, the catheter further comprises a retention balloon disposed about at least a portion of the distal segment of the elongate body. In any of the preceding embodiments, the catheter further comprises a second lumen configured for inflation of the retention balloon.

In any of the preceding embodiments, the cut depth percentage is about 40% to about 50% of the outer diameter of the elongate body. In any of the preceding embodiments, the cut depth percentage is about 58% to about 67% of the outer diameter of the elongate body. In any of the preceding embodiments, the cut depth percentage is about 50% to about 60%. of the outer diameter of the elongate body.

In any of the preceding embodiments, at least a subset of the plurality of flexibility regions has a cut length percentage of about 10% to about 90%. In any of the preceding embodiments, the cut length percentage is about 70% to about 80%.

In any of the preceding embodiments, a durometer of the elongate body is between about 20 Shore A to about 80 Shore A. In any of the preceding embodiments, the durometer of the elongate body is between about 40 Shore A to about 70 Shore A.

In any of the preceding embodiments, a length of the distal segment is about 1 cm to about 10 cm. In any of the preceding embodiments, the length of the distal segment is about 3 cm to about 5 cm.

In any of the preceding embodiments, a ratio of outer diameter of the elongate body to an outer projected thickness of a distal tip of the distal segment is about 1.0:0.8 to about 1.0:0.2.

In any of the preceding embodiments, the at least one flexibility region extends through an anterior sidewall of the elongate body through the first lumen and into a luminal surface of a posterior sidewall of the elongate body.

In any of the preceding embodiments, at least a portion of the elongate has a polygonal shape. In any of the preceding embodiments, the polygonal shape is a trapezoidal prism.

In any of the preceding embodiments, the plurality of flexibility regions comprises an anterior plurality of flexibility regions. In any of the preceding embodiments, the catheter further comprises a posterior plurality of flexibility regions.

In any of the preceding embodiments, the posterior plurality of flexibility regions each comprise a groove in an inner wall of the first lumen of elongate body. In any of the preceding embodiments, the grooves in the inner wall of the first lumen has a cut depth percentage of 5% to about 90%.

Another aspect of the present disclosure is directed to a urinary catheter comprising an elongate body having a proximal segment and a distal segment, such that the distal segment defines at least one port configured to drain a liquid from an organ; a retention balloon disposed about at least a portion of the distal segment of the elongate body; two or more lumens defined by the elongate body; and one or more flexibility regions disposed on or in the distal segment of the elongate body.

In any of the preceding embodiments, a first lumen is configured for drainage of the liquid from the organ and a second lumen is configured for inflation of the retention balloon.

In any of the preceding embodiments, the one or more flexibility regions are configured to promote unidirectional deflection of at least a portion of the distal segment during navigation of the elongate body.

In any of the preceding embodiments, there are two flexibility regions on an anterior distal region and two flexibility regions on a posterior distal region.

In any of the preceding embodiments, the two anterior and two posterior flexibility regions are each substantially transversely aligned.

In any of the preceding embodiments, there are at least two flexibility regions having a combined bending angle of about 20 degrees to about 70 degrees.

In any of the preceding embodiments, there are at least two flexibility regions having a combined bending angle of about 60 degrees to about 200 degrees.

In any of the preceding embodiments, there are at least two flexibility regions, a first more proximal flexibility region having a bending angle of about 50 degrees to about 70 degrees and the second more distal flexibility region having a bending angle of about 40 degrees to about 80 degrees.

In any of the preceding embodiments, the one or more flexibility regions comprise through holes.

In any of the preceding embodiments, the one or more flexibility regions comprise blind holes.

In any of the preceding embodiments, the one or more flexibility regions comprise a material of lesser durometer than the distal segment surrounding the one or more flexibility regions.

In any of the preceding embodiments, the one or more flexibility regions comprise a material of lesser durometer than the material comprising the elongate body.

In any of the preceding embodiments, the one or more flexibility regions extend semi-circumferentially around the elongate body.

In any of the preceding embodiments, the one or more flexibility regions comprise less material than the distal segment surrounding the one or more flexibility regions.

In any of the preceding embodiments, the elongate body further defines a third lumen, and the distal segment further defines an irrigation port, such that the third lumen is configured to transport fluid to the organ through the irrigation port.

In any of the preceding embodiments, the distal segment further defines an aperture configured to pass a guide wire therethrough.

In any of the preceding embodiments, the organ is a bladder.

Another aspect of the present disclosure is directed to a method of navigating or positioning a urinary catheter. In some embodiments, the method includes navigating an elongate body through a urethra of a patient; optionally temporarily and/or optionally unidirectionally passively deflecting at least a portion of a distal segment of the elongate body during navigation, such that the deflecting occurs in proximity to one or more of: bulbar urethra, membranous urethra, or prostatic urethra of the patient, and the temporary and unidirectional deflection occurs at a region comprising one or more flexibility regions; inflating a retention balloon disposed around the distal segment of the elongate body to retain at least a region of the distal segment in a bladder of the patient, such that inflation occurs via an inflation lumen defined by the elongate body and fluidly connected to a volume defined by the retention balloon; and intaking a liquid from the bladder of the patient through at least one port defined by the distal segment and fluidly connected to a lumen defined by the elongate body.

In any of the preceding embodiments, the method further includes deflating the retention balloon.

In any of the preceding embodiments, the method further includes removing the elongate body from the bladder and the urethra of the patient.

In any of the preceding embodiments, navigating further includes inserting the elongate body into the urethra of the patient.

In any of the preceding embodiments, the method further includes irrigating at least a portion of the bladder.

In any of the preceding embodiments, irrigation occurs via at least one irrigation port fluidly connected to an irrigation lumen defined by the elongate body.

In any of the preceding embodiments, the method further includes removing particulate from the bladder of the patient such that a distal end of the elongate body defines an aperture therein.

Another aspect of the present disclosure is directed to a urinary catheter comprising: an elongate body having a proximal segment and a distal segment; a retention balloon disposed about at least a portion of the distal segment of the elongate body; two or more lumens defined by the elongate body; and at least one port defined by the distal segment.

In any of the preceding embodiments, a first lumen is configured for drainage of a liquid from an organ and a second lumen is configured for inflation of the retention balloon In any of the preceding embodiments, the at least one port is configured to drain the liquid from the organ or pass a guidewire therethrough.

In any of the preceding embodiments, the at least one port is further configured to promote temporary, unidirectional deflection of at least a portion of the distal segment during navigation of the elongate body.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIG. 6A shows an anterior view of one embodiment of a flexible catheter.

FIG. 6B shows a side view of the embodiment of FIG. 6A.

FIG. 6C shows a side view of the embodiment of FIG. 6B in a bent configuration.

FIG. 7A shows an anterior view of another embodiment of a flexible catheter.

FIG. 7B shows a cross-sectional view, along section A-A, of the embodiment of FIG. 7A.

FIG. 8A shows an anterior view of another embodiment of a flexible catheter.

FIG. 8B shows a cross-sectional view, along section A-A, of the embodiment of FIG. 8A.

FIG. 10A shows an anterior view of another embodiment of a flexible catheter.

FIG. 10B shows a cross-sectional view, along section A-A, of the embodiment of FIG. 10A.

FIG. 11A shows an anterior view of another embodiment of a flexible catheter.

FIG. 11B shows a cross-sectional view, along section A-A, of the embodiment of FIG. 11A.

FIG. 12A shows an anterior view of another embodiment of a flexible catheter.

FIG. 12B shows a cross-sectional view, along section A-A, of the embodiment of FIG. 12A.

FIG. 14A shows an anterior view of another embodiment of a flexible catheter.

FIG. 14B shows a cross-sectional view, along section D-D, of the embodiment of FIG. 14A.

FIG. 15A shows an anterior view, or anterior view, of another embodiment of a flexible catheter.

FIG. 15B shows a side view of the embodiment of FIG. 15A.

FIG. 16A shows a side view of another embodiment of a flexible catheter.

FIG. 16B shows an anterior cross section view, along section A-A, of the embodiment of FIG. 16A.

FIG. 19D shows a posterior section view, along section B-B, of the embodiment of FIG. 19B.

FIG. 19E shows a lateral cross-sectional view, along section C-C of the embodiment of FIG. 19C.

FIG. 19F shows a cross-sectional view, along section D-D, of the embodiment of FIG. 19E.

FIG. 19G shows a cross-sectional view, along section E-E, of the embodiment of FIG. 19E.

FIG. 20A shows an anterior view of another embodiment of a flexible catheter.

FIG. 20B shows a cross-sectional view, along section A-A, of the embodiment of FIG. 20A.

FIG. 20C shows a cross-sectional view of another embodiment of a flexible catheter.

FIG. 20D shows a cross-sectional view of the embodiment of FIG. 20C along section B-B.

FIG. 20E shows a flexibility region in a tube for volume calculations.

FIG. 20F shows the material that was removed from the flexibility region of FIG. 20E.

FIG. 21A shows an anterior view of another embodiment of a flexible catheter.

FIG. 21B shows a cross-sectional view, along section B-B, of the embodiment of FIG. 21A.

FIG. 22A shows an anterior view of another embodiment of a flexible catheter.

FIG. 22B shows a side view of the embodiment of FIG. 22A.

FIG. 22C shows an anterior cross-sectional view, along section A-A, of the embodiment of FIG. 22B.

FIG. 24A shows a side view of one embodiment of a flexible catheter having one or more proximally positioned flexibility regions.

FIG. 24B shows a cross-sectional view, along section A-A, of the embodiment of FIG. 24A.

FIG. 24C shows a cross-sectional view, along section B-B, of the embodiment of FIG. 24A.

FIG. 24D shows a cross-sectional view, along section C-C, of the embodiment of FIG. 24A.

FIG. 25A shows a top view of another embodiment of a flexible catheter having a tapered distal tip.

FIG. 25B shows a side view of the embodiment of FIG. 25A.

FIG. 25C shows a side-sectional view of the embodiment of FIG. 25A.

FIG. 28A shows a top view of another embodiment of a flexible catheter.

FIG. 28B shows a side view of the embodiment of FIG. 28A.

FIG. 28C shows a cross-sectional view of the embodiment of FIG. 28A.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

As described herein, various flexible catheters are described. It should be appreciated by one of skill in the art that the catheters described herein, although described with reference to the urinary system or urinary tract, can, of course be used in other peripheral, vascular, or organ system. For example, the catheters described herein may be configured for use in the nasopharynx, the larynx/trachea/bronchi, gastrointestinal tract, neuro-vasculature, peripheral vasculature, or any other suitable bodily lumen or organ system.

The various flexible catheters described herein are intended to inflict less trauma to transit tissue (tissue in the vessel) and the target organ. They accomplish this by having increased flexibility, increased bendability, decreased stiffness, and increased trackability (e.g., reduced insertion force), which results in one or more of the following advantages: reduced perforation risk, decreased stricture or scar formation (e.g., urethral stricture, esophageal stricture), decreased spasms (e.g., bladder spasms, laryngospasms, vasospasms, etc.), reducing infection risk as a result of decreased trauma, decreased denudation risk of various tissue layers, and reduced risk of creating false passages (e.g., urethral false passage, pseudoaneurysm).

Figure 2:
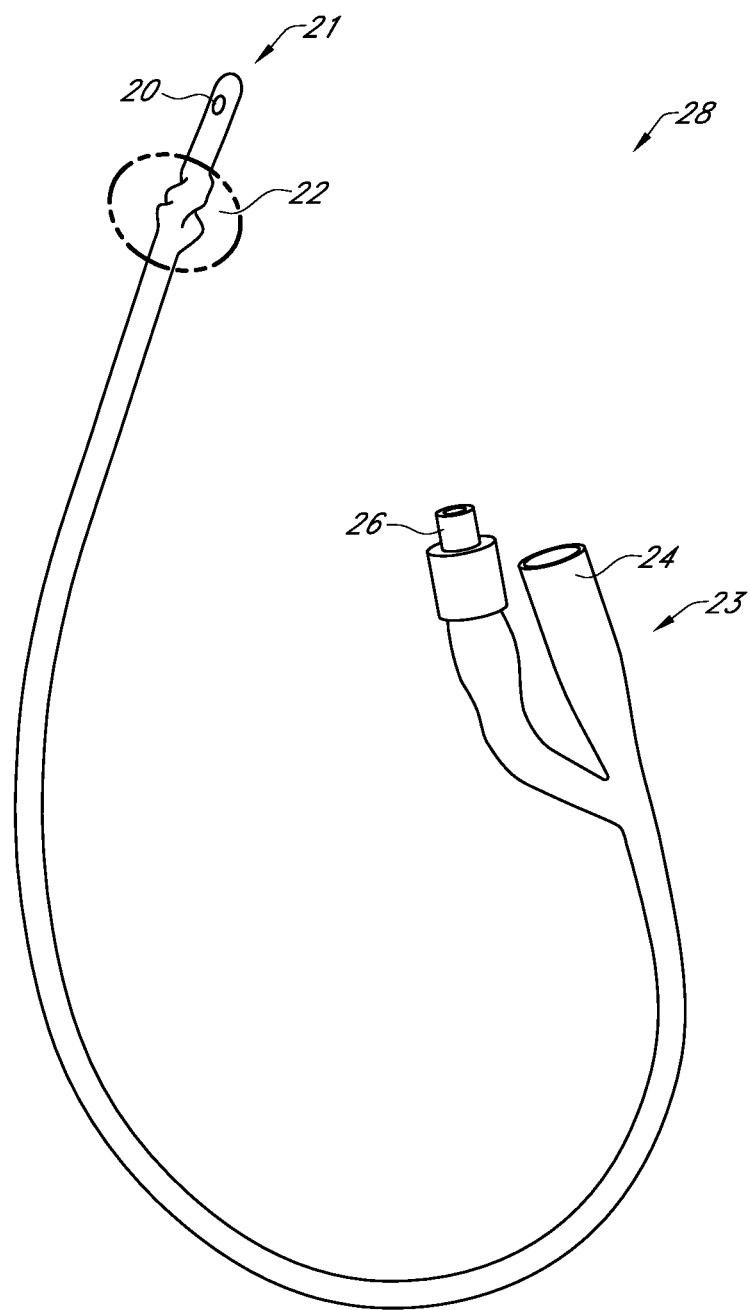
FIG. 2 illustrates a typical two-way catheter.

As used herein, "proximal" means near or toward an operator of the device and "distal" means away from the operator and toward a patient or target tissue or organ in which the catheter is inserted. Distal end 21 and proximal end 23 are further labeled in FIG. 2 for the sake of clarity but are understood to apply to all the embodiments described herein.

Figure 5:
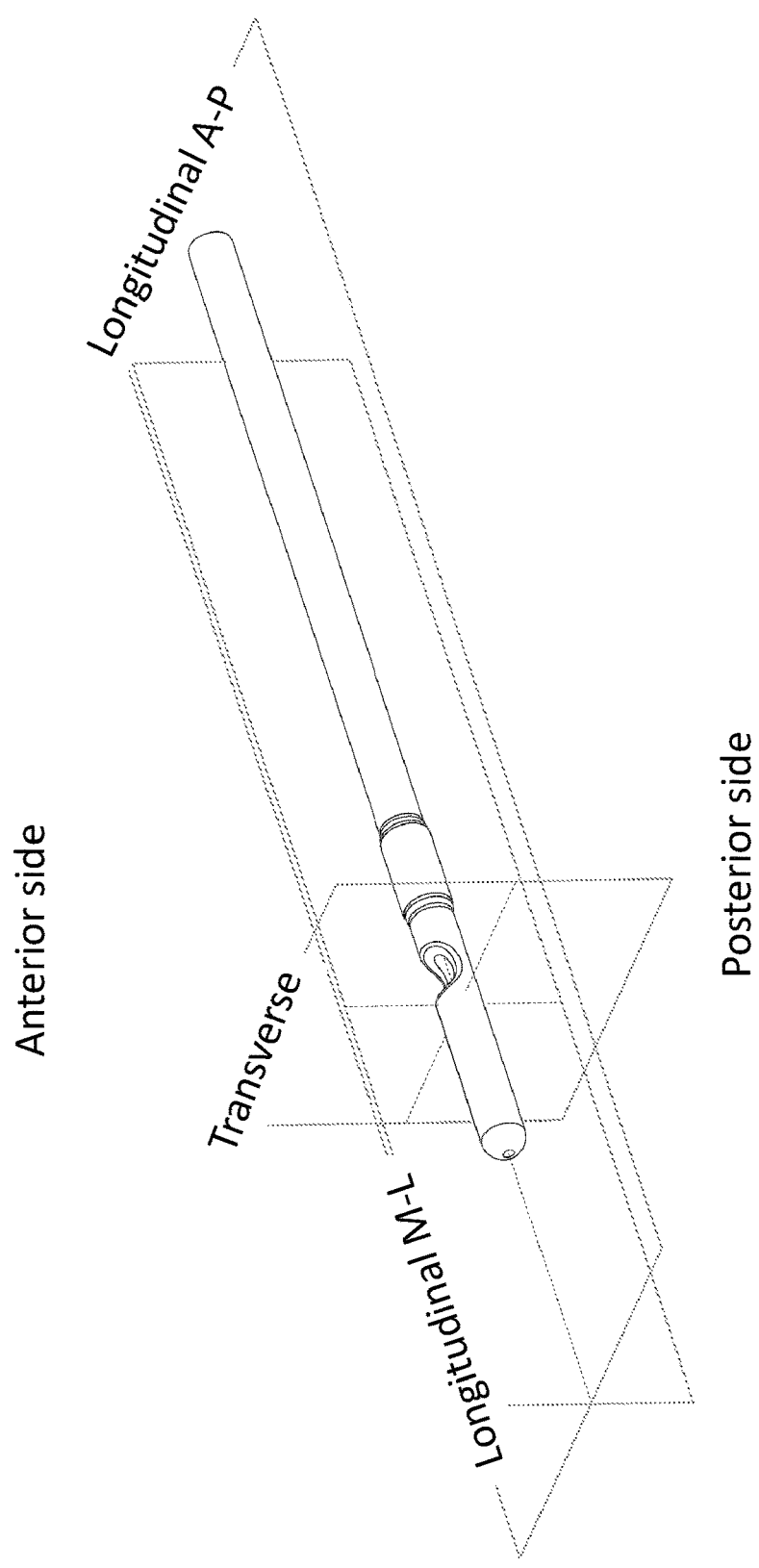
FIG. 5 shows various planes and sides of a catheter.

As used herein and as shown in FIG. 5, "anterior side" is the inside radius of the bent configuration of the catheter on a top or anterior side of a longitudinal A-P (anterior-posterior) plane, and "posterior side" is the outside radius of the bent configuration of the catheter on a bottom or posterior side of a longitudinal A-P plane. Also shown is a medial (M) and lateral (L) longitudinal section of the catheter. Further, in some embodiments described herein, flexibility regions may be transversely aligned or aligned in a transverse plane. For example, a first flexibility region may be positioned on an anterior side and a second flexibility region may be positioned on a posterior side but the first and second flexibility regions may be aligned with each other transversely or in a transverse plane. In some embodiments, flexibility regions may be longitudinally aligned or aligned in a longitudinal plane, as shown in FIG. 5.

As used herein, "passive" deflection comprises deflection as a result of anatomical and physiological curvature that does not necessarily require an active mechanism, such as, for example, pullwires, concentric tubes, and the like. Such "active" deflection mechanisms (pullwires, concentric tubes, etc.) require an additional actuating mechanism to effect the deflection.

Figure 29A:
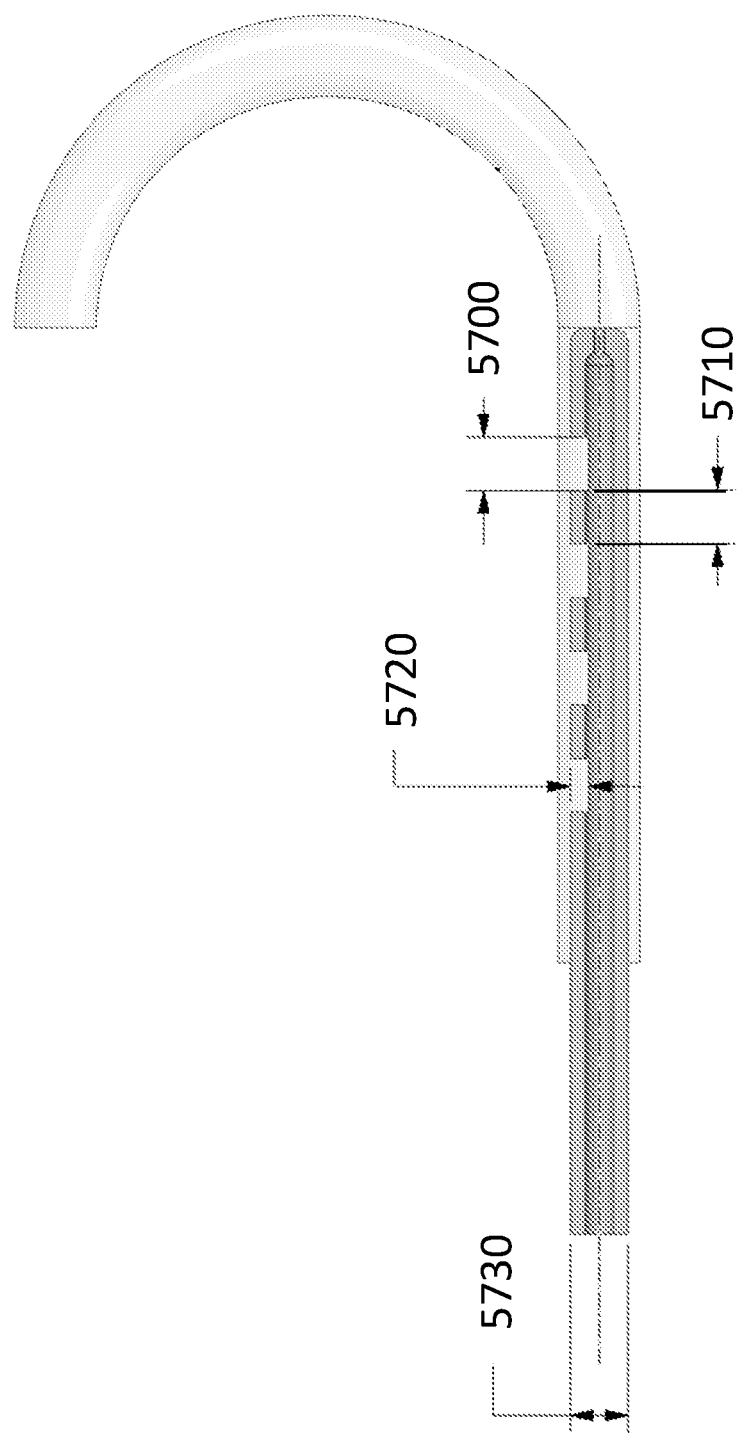
FIG. 29A shows a perspective view of an elongate body with various measurable parameters labeled.

As used herein and shown in FIG. 29A, a "cut length percentage" is defined as a cut length 5700 (i.e., flexibility region length or a length of the region that has been altered to change a flexibility of the region) divided by cut length plus the length between cuts 5710 (i.e., flexibility regions). The cut length percentage may vary depending on the size of the catheter used.

Figure 29C:
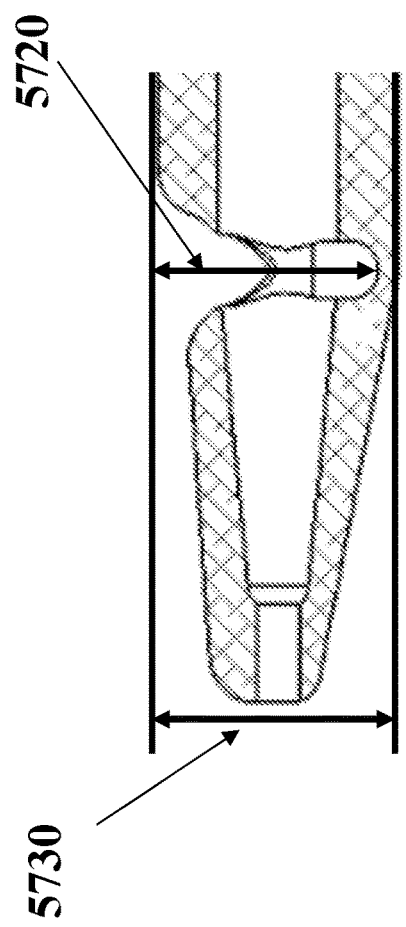
FIG. 29C shows a zoomed-in cross-section view of another embodiment of a cut depth of a flexibility region.
Figure 29B:
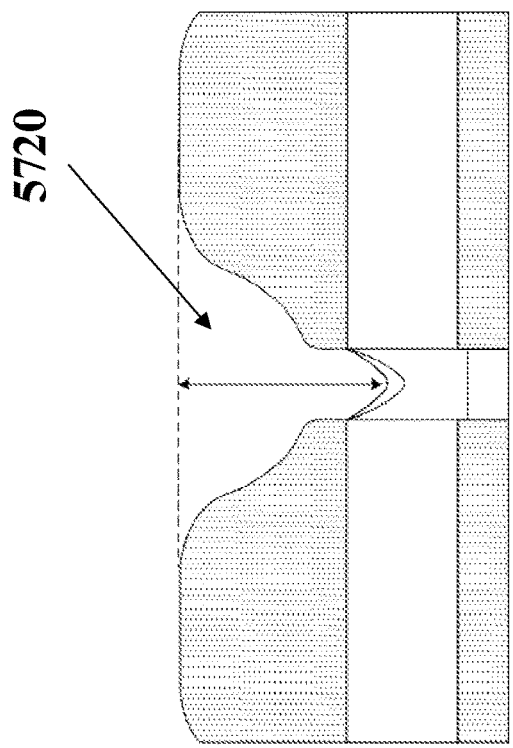
FIG. 29B shows a zoomed-in cross-section view of one embodiment of a cut depth of a flexibility region.
Figure 29D:
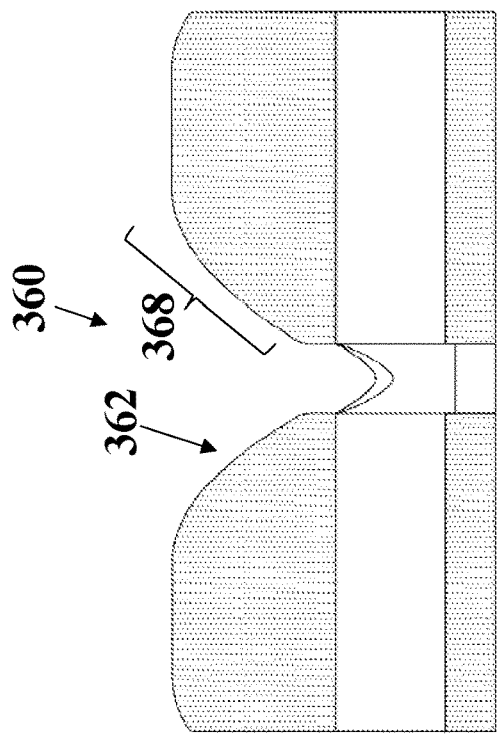
FIG. 29D shows a zoomed-in cross-section view of one embodiment of a shape of a flexibility region.
Figure 29E:
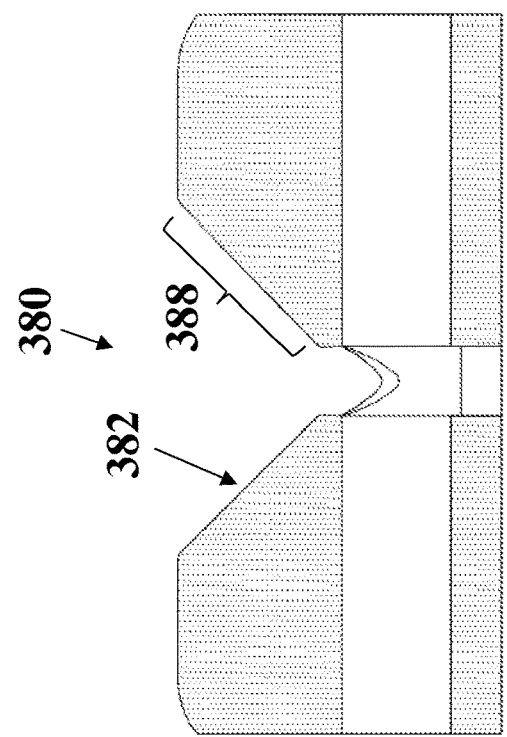
FIG. 29E shows a zoomed-in cross-section view of another embodiment of a shape of a flexibility region.
Figure 29F:
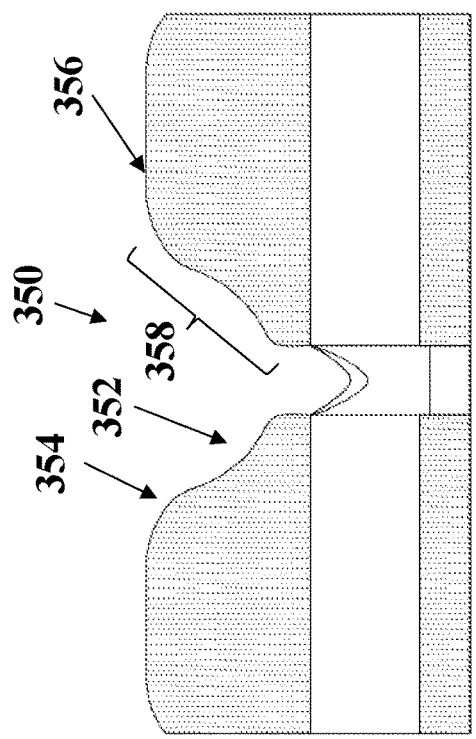
FIG. 29F shows a zoomed-in cross-section view of another embodiment of a shape of a flexibility region.
Figure 29G:
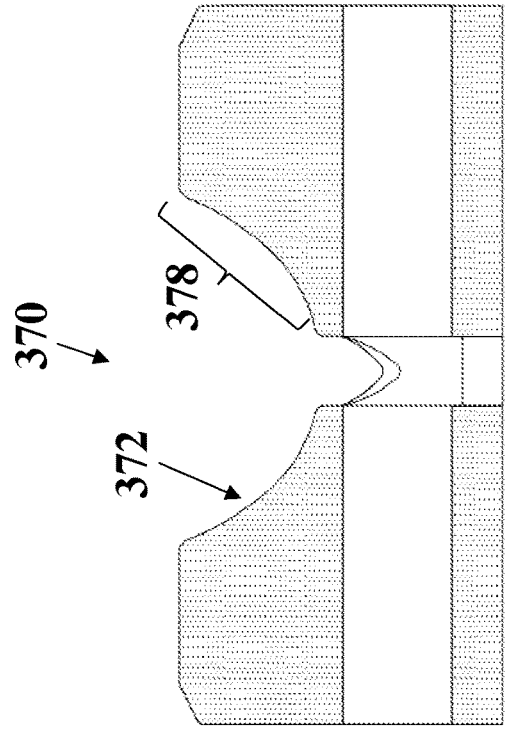
FIG. 29G shows a zoomed-in cross-section view of another embodiment of a shape of a flexibility region.

In some embodiments, as used herein and shown in FIG. 29A, a "cut depth percentage" is defined as a depth 5720 of a transverse cut or flexibility region or region that has been altered to change a flexibility of the region (lower durometer material, material removal, etc.), perpendicular to a longitudinal axis of the elongate body as in FIG. 5, in an elongate body divided by an outer diameter 5730 of the elongate body, multiplied by 100. The cut extends from an exterior surface of the elongate body to a transversely offset interior region of the elongate body. In some embodiments, as shown in FIG. 29B, the flexibility region includes material removal circumferentially from an inner sidewall of the lumen, such that the transversely offset region includes the cut depth corresponding to where material was removed from the inner sidewall. In other embodiments, as shown in FIG. 29C, the transversely offset interior region penetrates the lumen and the opposite inner sidewall of the lumen, such that the cut depth percentage includes an inner diameter of the lumen and the depth of the cut into the opposite inner sidewall (e.g., posterior sidewall when the flexibility region is in an anterior sidewall). Taking a cross-sectional view of various embodiments of flexibility regions, it is appreciated that the material may be removed to form the flexibility region in a number of different ways. A perimeter 358 of a flexibility region 350 may have a convex section 354 near an external surface 356 of the catheter that transitions to a concave section 352, as shown in FIG. 29D. A perimeter 368 of a flexibility region 360 may have a convex shape 362, as shown in FIG. 29E. A perimeter 378 of a flexibility region 370 may have a concave shape 372, as shown in FIG. 29F. A perimeter 388 of a flexibility region 380 may be slanted 382 (e.g., angled relative to a transverse axis) or perpendicular (parallel to a transverse axis), as shown in FIG. 29G. This list is non-exhaustive but meant to illustrate various shapes of material removed to create flexibility regions. The cut depth 5720 may be measured from a posterior side of the elongate body to a transversely offset interior region or from an anterior side of the elongate body to a transversely offset interior region.

In other embodiments, as used herein, the cut depth percentage is defined relative to a wall thickness of the elongate body (instead of the outer diameter). For example, as shown in FIG. 16G, the cut depth percentage relative to a sidewall thickness is about 10% to about 80%, about 20% to about 80%, about 20% to about 30%, about 30% to about 70%, about 70% to about 80%, etc. Embodiments that are relative to a sidewall thickness will be indicated when describing the respective embodiment.

As used herein, a "percent volume removed" or "percent volume" is defined as a volume of material that has either been removed to produce a cut in a sidewall of a catheter (inner or external sidewall) or a volume of material that has been replaced with a higher or lower durometer material in a sidewall of the catheter (inner sidewall or external sidewall). The volume that is removed may not necessarily penetrate a lumen of the catheter but may be superficial. In some embodiments, the percent volume removed from a flexibility region is a good indicator for actual material removed since it takes into account material removed from an anterior region, a posterior region, and/or circumferentially from a sidewall in the lumen.

The bounds of the plane tube for purposes of the percent volume calculation are defined above as the cut length of the flexibility region. As such, the percent volume of a flexibility region is calculated by determining the volume of removed material relative to the volume of the plain tube (i.e., no modification). Note that the volume will take into account material removed from the anterior wall, outer lateral walls, inner lateral walls, and posterior wall, where applicable.

In general, a full length of any of the urinary catheter embodiments described herein may be about 40 cm to about 60, for example about 45 cm to about 50 cm; use-specific catheters for other indications may have different lengths as clinically appropriate. Further, in any of the embodiments described herein, a distal tip of the catheter or elongate body may be modified to have a bulbous-tip (along a transverse plane) by those of skill in the art. In any of the embodiments described herein, a distal tip of the catheter or elongate body may be modified to have a tapered tip, such as that shown in FIGS. 25A-25B and further described elsewhere herein. In any of the embodiments described herein, a distal tip of the catheter or elongate body may be modified to have an offset tip (offset from a longitudinal axis of the elongate body), such as that shown in FIGS. 22A-22G and further described elsewhere herein. In any of the embodiments described herein, a distal tip of the catheter or elongate body may be modified to include a bulge, such as that shown in FIGS. 19A-19G and further described elsewhere herein.

As used herein, a "flexibility region" may comprise any one or more or a plurality of the following characteristics or features: through-holes; blind-holes; apertures; cutouts in an outer diameter of the catheter; cutouts in an inner diameter of the catheter; cutouts that traverse a sidewall of the catheter and permit fluid communication between the lumen and external environment; material of a differing durometer than the rest of the catheter body; concavity; convexity; etc. Further, a flexibility region may be elongate, circular, oval, rectangular, square, punctate, non-cylindrical, bulbous, tapered cylindrical, hollowed conical, polygonal, etc. Still further, one or more flexibility regions may be arranged in a pattern to impart flexibility to a region, for example, the flexibility region includes features or characteristics that are: radially arranged; linearly arranged; positioned on an anterior half of the catheter; positioned on a posterior half of the catheter; positioned distally to an irrigation/drainage port; positioned proximally to an irrigation/drainage port; positioned both distally and proximally around an irrigation/drainage port; etc.

In some embodiments, a flexibility region is created by removing a volume of material to increase flexibility at that region or by replacing a volume of material with a material of a different durometer to increase flexibility at that region. The volume may be removed from or replaced at: an external surface of the catheter, an external surface through to a lumen of the catheter, an at least partially circumferential location of the lumen of the catheter, a posterior inner wall of the lumen, an interior region of a sidewall such that an external surface of the catheter or a luminal surface of the catheter is not breached, or otherwise. The volume removed or replaced may range from about 0.1% to about 95%, for example, about 0.1% to about 2%, about 1% to about 5%, 5% to about 10%, about 10% to about 20%, about 20% to about 30%, about 30% to about 40%, about 40% to about 50%, about 50% to about 60%, about 60% to about 70%, about 70% to about 80%, about 80% to about 90%, or greater than 90%. When material is replaced with a different durometer material, a volume percent of 100% of flexibility region may be comprised of the different durometer material.

In some embodiments, one or more flexibility regions alone or in concert are configured to impart a bend of about 5 degrees to about 180 degrees; about 15 degrees to about 85 degrees, about 20 degrees to about 80 degrees; about 20 degrees to about 60 degrees, about 20 degrees to about 40 degrees, about 15 degrees to about 30 degrees, etc. to a distal segment of the catheter. For example, a first flexibility region may impart a bend of about 15 degrees to about 25 degrees to a proximal portion of a distal segment of the catheter body and a second flexibility region may impart a bend of about 50 degrees to about 80 degrees to a distal portion of a distal segment of the catheter body. The angle of bend measurements (in degrees) described herein are absolute and measured from an initially "flat and horizontal" axis, not relative to a curvature or bend of a more proximal segment of the catheter body. The angle would be relative if it were dependent on a position or orientation of a more proximal portion of the elongate body. Said another way, if the catheter were in a linear unbent configuration, all the degree measurements herein are measured from a longitudinal axis of the catheter in the linear, unbent configuration. To show the degree of bend of various sections of the catheter, as shown in FIGS. 12D and 13C, some relative degrees of bend are shown, but the starting point is from an absolute bend starting point (measured from an initially "flat and horizontal" axis).

As shown and described herein, any of the flexibility regions are structured, shaped, and/or otherwise positioned to promote deflection anteriorly, for example unidirectional deflection in an anterior direction. However, unidirectional deflection posteriorly or in a side plane is also envisioned.

In general, any of the devices herein may be coated. For example, a coating may be hydrophilic, lubricious, have antimicrobial properties, or the like. The coating may comprise: silicone, Polytetrafluoroethylene (PTFE), silver, etc.

In general, any of the devices herein may comprise no balloon, one balloon, or two balloons on the elongate body. For example, a double balloon embodiment may be used for induction of labor in obstetrics or retrograde urethrogram. A two balloon catheter embodiment comprise one or more eyelets between balloons and/or to cushion the tip to reduce suction effects of eyelets.

In general, any of the devices described herein may comprise or be formed of, at least in part, natural latex, silicone, latex, polyisoprene, silastic-latex (e.g., latex with silicone coating), vinyl, urethane, TPE, etc. The material may have a durometer of about 20 Shore A to about 80 Shore A, about 30 A to about 70 A, about 25 A to about 75 A, about 35 A to about 53 A, or about 45 A to about 55 A, preferably about 40 A to about 70 A.

In general, any of the devices herein may come in a variety of sizes: about 12 to about 30 French; about 14 to about 16 French; about 12 French; about 14 French; about 16 French; about 18 French; about 20 French; about 22 French; about 24 French; about 26 French; about 28 French; about 30 French-etc. One unique feature of the present disclosure is providing devices with sizing that is more readily accessible by a user, for example using language such as small, medium, large, and/or extra-large. For example, a small size may comprise a 14 French catheter; a medium size may comprise a 17 French catheter; a large size may comprise a 22 French catheter; and an extra-large size may comprise a 25 French catheter.

In some embodiments, any of the catheters described herein may include one or more indicators or markings to distinguish an anterior side from a posterior side of the catheter, the anterior side being the bending side (side with inner radius when in bent configuration). For example, the indicator or marking may include different shading or coloring, printed orientation line, dashes, dots or stripe, text, symbols, or the like on the anterior versus posterior side.

In some embodiments, as described herein, the bending or deflection of the distal end or distal portion of the catheter may be temporary such that it only deflects upon encountering resistance in the bodily lumen, but is otherwise substantially unbent or substantially not pre-bent. For example, temporary deflection may include only bending during passage by the apex of the prostate gland or after passing or clearing the prostate, such that it assumes a substantially straight profile thereafter.

In general, any of the devices described herein may be packaged, sold, manufactured, or otherwise distributed as a kit. For example, the kit may include a lubricant, for example KY jelly, a jelly comprising an anesthetic (e.g., lidocaine), or the like. The kit, of some embodiments, may include a drainage bag with tubing (e.g., spiral tubing). In some embodiments, the kit may include one or more catheters, for example any combination of small, medium, large, and/or extra-large catheters may be included in the kit. The kit may, optionally, include an anti-septic solution for cleaning the urethral meatus prior to insertion and/or a syringe with sterile water for filling a balloon of the catheter. Further, the kit may optionally include a catheter holding device that secures the catheter to the body (e.g., adhesive with catheter rotating device to secure it to a thigh).

Further, many of the embodiments described herein show a distal aperture to drain liquid from an organ, for example; however, it is similarly conceivable and does not depart from the scope of the present disclosure that the distal end may not include an aperture. Alternatively, the aperture may be present but used to pass a wire therethrough for tracking.

Further, many of the embodiments described herein show a lumen defined by the catheter body to drain liquid from an organ, for example; however, it is similarly conceivable and does not depart from the scope of the present disclosure that at least portions of the catheter body do not define a lumen. For example, a distal end portion of the catheter body may not include a lumen. In such embodiments, the lumen extends up to one or more apertures but terminates at those apertures, such that draining, irrigation, and/or balloon irrigation can still occur, but a stiffness profile of the catheter is maintained beyond termination of the lumen(s). For example, in some embodiments, a distal most about 1.5 cm to about 2.5 cm may not include a lumen or a distal most about 5 cm to about 6 cm may not include a lumen.

In embodiments including two or more apertures, one of skill in the art will appreciate that the apertures may be on opposite sides of the catheter body (transversely offset), may be axially or longitudinally aligned, may be anteriorly positioned, may be posteriorly positioned, etc., without departing from the scope of the present disclosure.

Further, although the accompanying catheter drawings only show a distal end portion or segment of each embodiment, one of skill in the art will appreciate that any proximal end features may be used, or proximal end region control mechanism may be used. For example, anchoring balloon, valves, connectors, rapid exchange segments, drainage bags, syringes for liquid injection, actuating mechanisms, etc. may be included on a proximal end of each catheter described herein without departing from the scope and intent of this disclosure. In some variations, the proximal end portion or segment may optionally be used as a temperature probe as well as an irrigation lumen.

Further, although one or more flexibility regions are shown distally, for example distal to a retention balloon, one of skill in the art will appreciate that one or more flexibility regions may be more proximal or proximal to the retention balloon. For example, there may be one or more flexibility regions about 1 cm to about 12 cm; about 1 cm to about 5 cm; about 5 cm to about 15 cm; about 8 cm to about 12 cm; about 10 cm proximal to the retention balloon. In one embodiment, the one or more flexibility regions may comprise any of the disclosed embodiments described herein and be spaced, for example about 2.5 cm apart proximal to the retention balloon. In some embodiments, proximal flexibility regions may be symmetrical such that bending is not promoted in one direction over another. Such proximal flexibility regions will be described in further detail below in connection with FIGS. 24A-24F.

In any of the embodiments described herein, there are various optional features that may be included, for example: a temporary obturator during insertion or a vacuum source to promote full draining of the catheter (for example in those embodiments that have internal flexibility regions).

In any of the embodiments described here, the various features may also be employed in a urethral dilator. As such, any of the features of the following embodiments may be employed in a urethral dilator without departing from the scope of the invention disclosed herein.

In any of the embodiments described herein, one or more portions of the catheter may be radiopaque. In one embodiment, an entire length of the catheter is radiopaque.

In general, the dimensions shown and described herein pertain to an 18Fr device. As one of skill in the art would appreciate, the dimensions may be linearly scaled up or down based on the size of the device.

Figure 1:
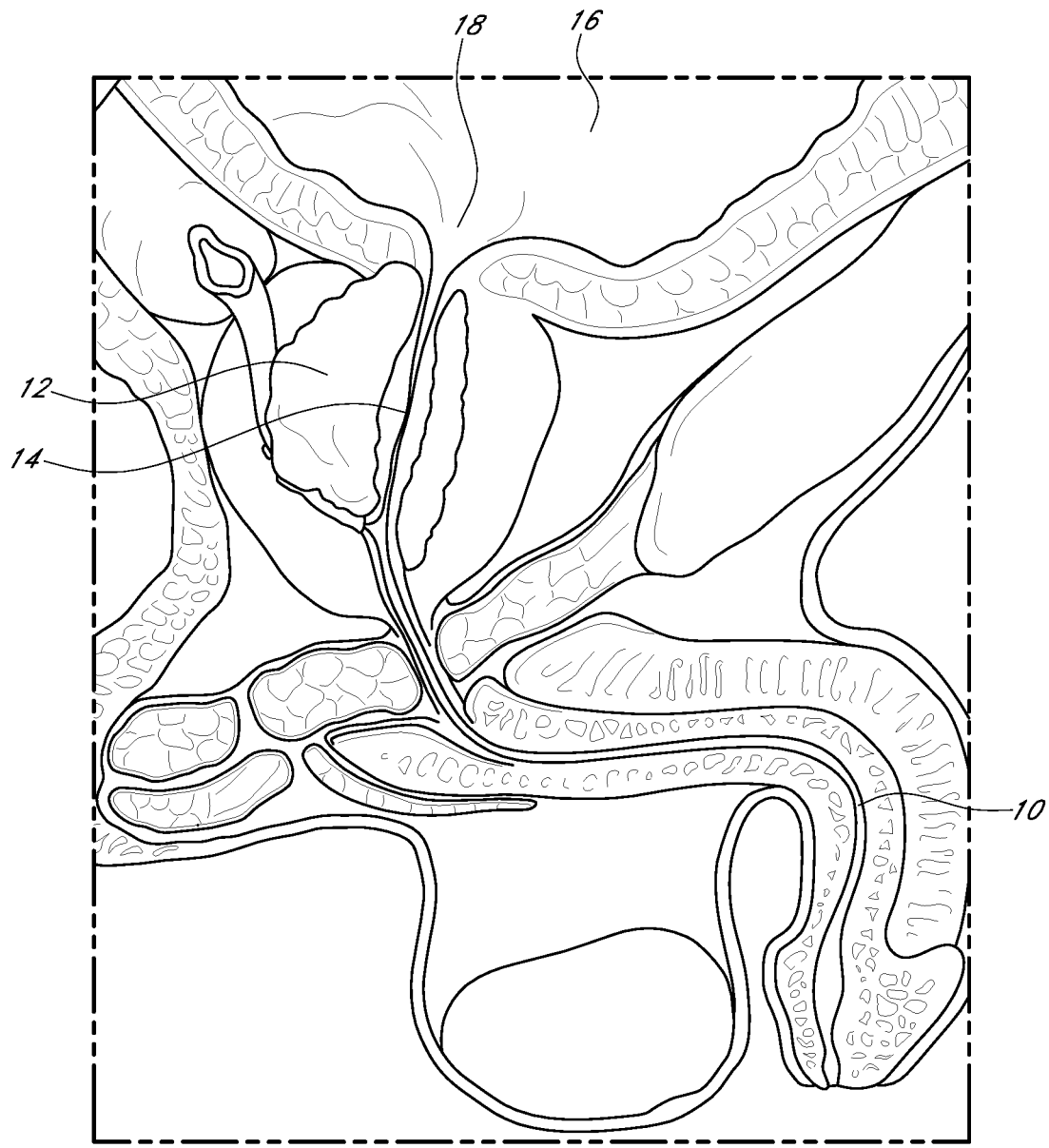
FIG. 1 illustrates a urinary tract of a male.
Figure 3:
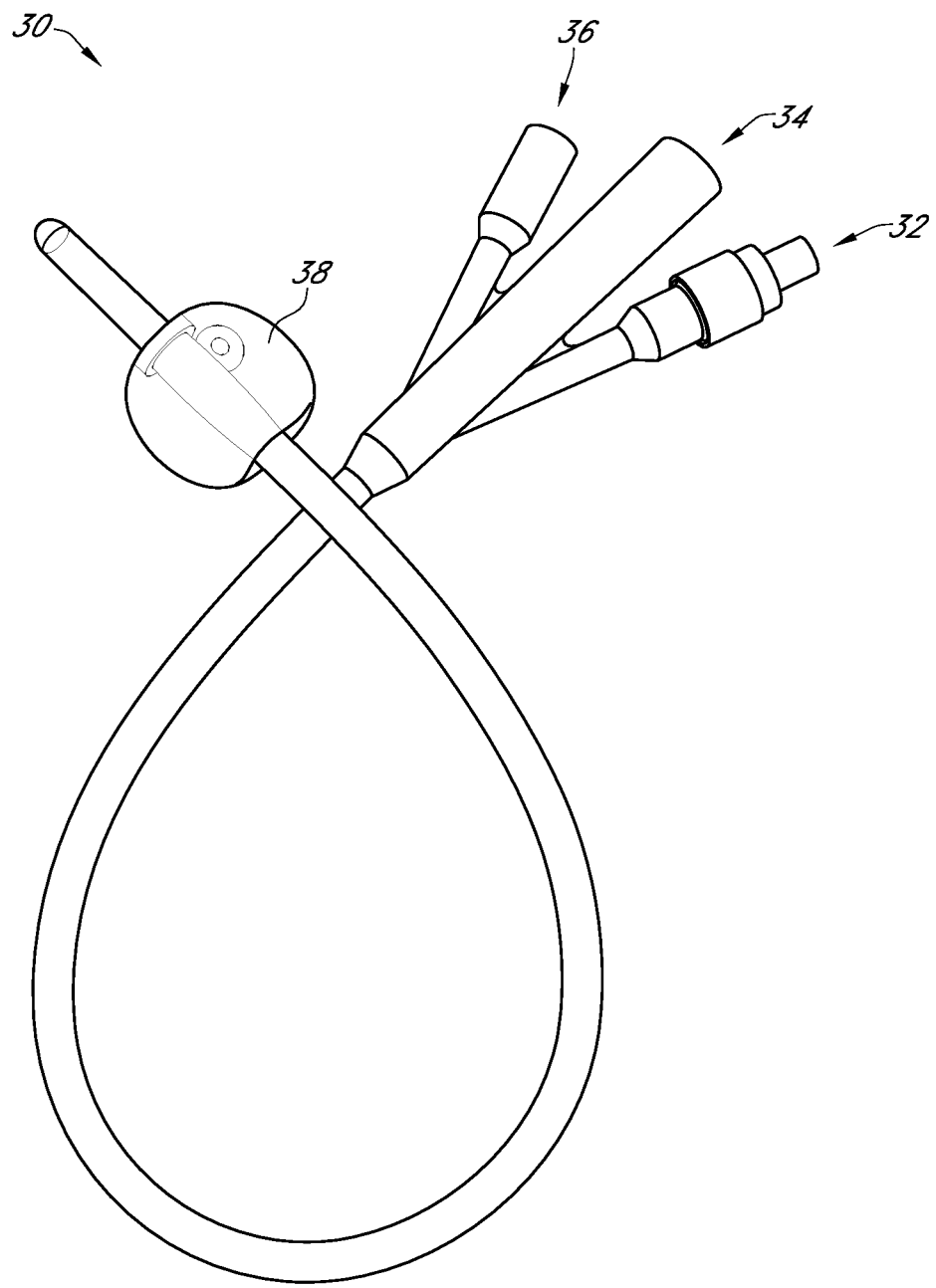
FIG. 3 illustrates a typical three-way catheter.
Figure 4A:
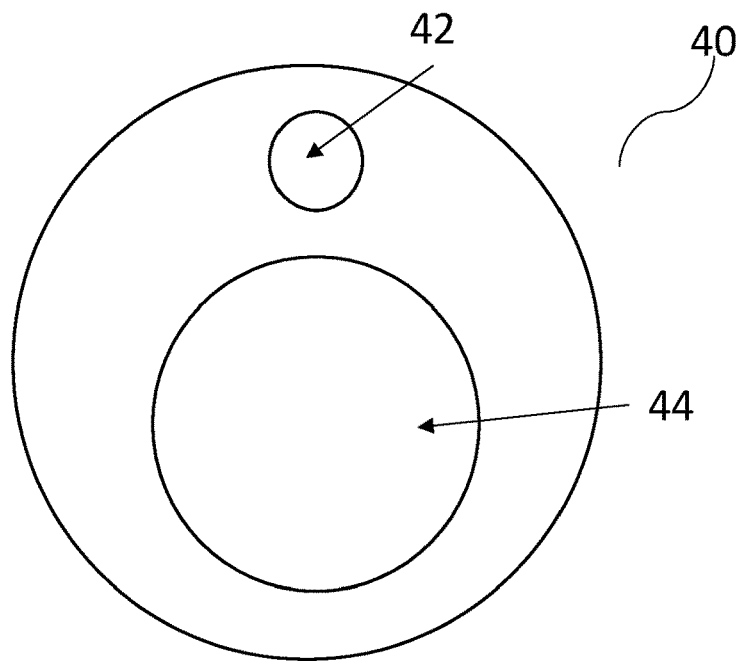
FIG. 4A shows a cross-sectional view of a typical two-way catheter.
Figure 4B:
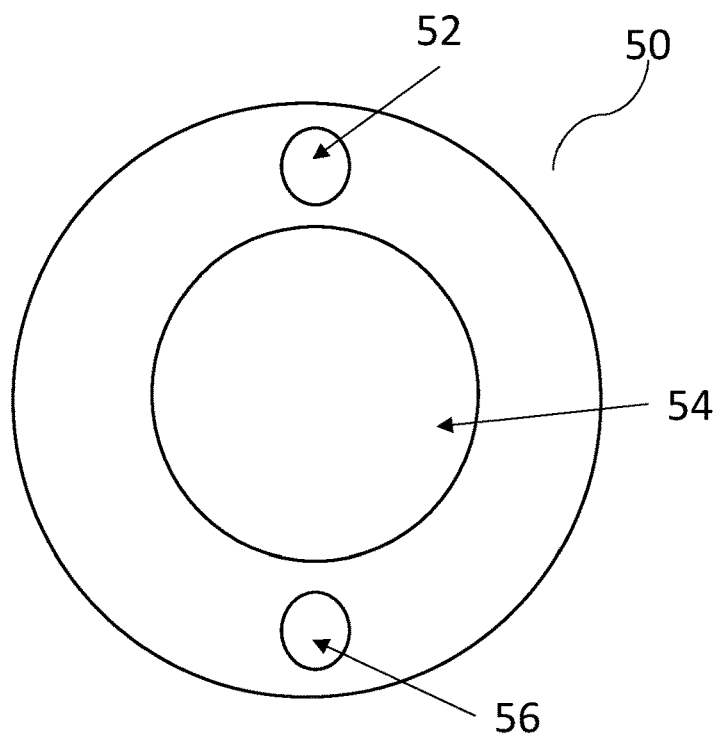
FIG. 4B shows a cross-sectional view of a typical three-way catheter.

FIG. 1 shows a male urinary tract. When a catheter is inserted into the male urinary tract, it is advanced through the penile urethra 10 into the prostatic urethra 14, past the prostate gland 12 and through the bladder neck 18 of the bladder 16. As shown in FIG. 1, the male anatomy poses significant bends through which the catheter must track to reach the bladder. In females, the path to reach the bladder is less tortuous. The catheter is inserted through the external urethral orifice through the urethra through the bladder neck into the bladder. Regardless of the anatomy, catheter insertion into the urinary tract can be difficult; the tissue being sensitive, there being tortuous anatomy, and there being the potential that different organs (e.g., the prostate) impinge on the urinary tract, making passage difficult. Currently available catheters are difficult to use and the selection of which is confusing. For example, there is no pre-catheter insertion imaging routinely performed, and a Foley catheter, Coudé® catheter, or guide wire with Councill tip may not go in. Additionally, it can be more difficult after the first attempt due to tissue trauma or injury from the first failed attempt. There may be significant bleeding, and patient anxiety/discomfort/pain escalates with each failed attempt. In some cases, a practitioner may need to resort to flexible cystoscopy or suprapubic tube insertion. Further, for example, adult catheters range in size from 12 French to 30 French, which is a measure of the external diameter of the catheter. However, deciding which catheter size will be appropriate for a patient, given a large range of sizes, can be difficult. Further, some catheters only have selected features, resulting in the need to switch between different catheters to achieve the intended function. For example, as shown by way of exemplary catheter 28 in FIG. 2, some catheters include a distal aperture 20 for passive particulate or urine removal; a two-way channel 24, 26 for drainage from distal aperture 20 and balloon inflation, respectively; and/or an expandable balloon 22 for retention in the bladder; etc. Further for example, as shown by way of exemplary catheter 30 in FIG. 3, some catheters include a three-way channel (e.g., lumen for filling retention balloon 32, lumen for irrigating 36, lumen for drainage 34); an expandable balloon 38 for retention in the bladder; a plurality of apertures for particulate removal and/or irrigation; etc. In other embodiments, both irrigation and drainage occur through the same lumen. FIG. 4A further shows a cross-sectional view of a catheter body 40 defining two lumens for drainage 44 and filling a retention balloon or irrigation 42. FIG. 4B further shows a cross-sectional view of a catheter body 50 defining three lumens for drainage 54, filling a retention balloon 52, and irrigation 56. Any of the catheters described herein may include any one or more of the features described in connection with FIGS. 2-5, such that the catheter is multifunctional, reducing the need to use multiple catheters to achieve an intended outcome for a patient.

Turning now to FIGS. 6A-6C, which show one embodiment of a flexible catheter. As shown in the unbent configuration of FIGS. 6A-6B, an elongate body 60 of the catheter defines one or more flexibility regions shown as a plurality of blind or through holes 62 proximal to the distal tip 64. As shown in FIG. 6C, the distal end 66 bends at flexible region 62. The embodiment of FIGS. 6A-6C further comprise a retention balloon 68, shown in an uninflated state, positioned proximally relative to the flexibility region 62.

FIGS. 7A-7B show a similar embodiment to that of FIGS. 6A-6C, except in this embodiment, elongate body 70 defines a single aperture 72 as the flexibility region at which the elongate body 70 bends unidirectionally. As shown in FIGS. 7A-7B and to contrast FIGS. 7A-7B to other embodiments herein, the flexibility region 72 includes material removed from an anterior sidewall, the removal of material extending circumferentially around the outer diameter of the catheter, such that the flexibility region has a U-shaped cross-section, as shown in FIG. 7B. The material removal extends to a plane that resides along a longitudinal axis of the catheter. In the embodiment shown in FIG. 7B, the plane resides between about 40% to about 60% of the outer diameter, for example at about 50%. The cut depth percentage 75 for flexibility region 72 is about 40% to about 60%. As above, the catheter body 70 defines a lumen 71 therethrough, includes, but does not require, retention balloon 78 (in an uninflated state), and distal tip 74. Distal tip 74 defines aperture 73 for passing a guide wire therethrough, draining liquid from an organ, or irrigating tissue in an organ. In any of the embodiments described herein, the distal tip aperture 73 may be centered along an axial or longitudinal centerline axis of the catheter body or offset from a centerline axis of the catheter body.

FIGS. 8A-8B (FIG. 8B being a cross-sectional view of FIG. 8A along section A-A) show the embodiment of FIGS. 7A-7B while further including a second flexibility region 85 comprising descending wall thickness (from distal to proximal) at distal end on an anterior aspect. For example, distal to aperture 82, the second flexibility region 85 includes a first inner wall thickness 85a that transitions to a second inner wall thickness 85b, the second thickness 85b being thinner than the first thickness 85a. The transition between the first and second thickness may be graded, stepped, gradual, etc. For example, the transition may be from about 0.25 to about 0.5 mm or from about 1 mm to about 2 mm. The percent volume of material removed to create the second flexibility region 85 may be about 5% to about 30%. As above, the catheter body 80 defines a lumen 81 therethrough, includes, but does not require, retention balloon 88 (in an uninflated state), and distal tip 84. Distal tip 84 defines aperture 83 for passing a guide wire therethrough, draining liquid from an organ, or irrigating tissue in an organ.

Figure 9A:
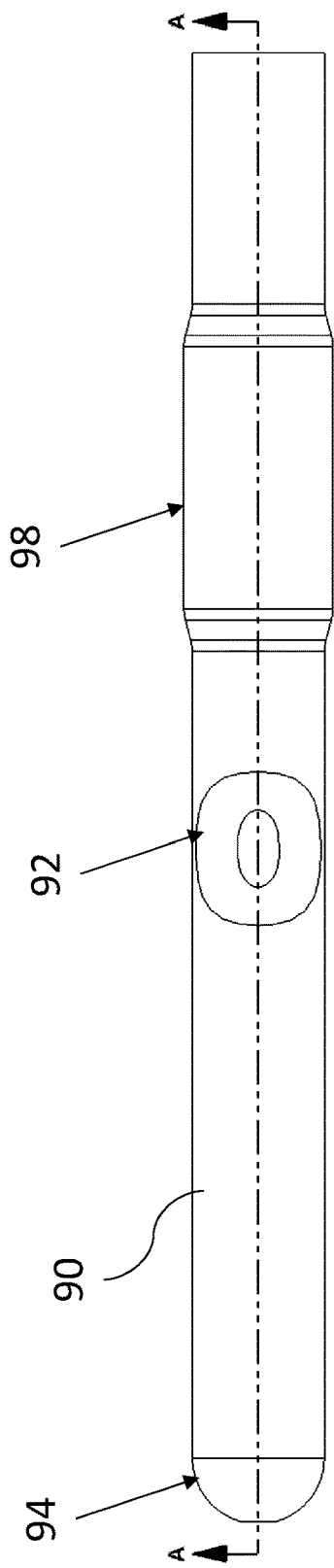
FIG. 9A shows an anterior view of another embodiment of a flexible catheter.
Figure 9B:
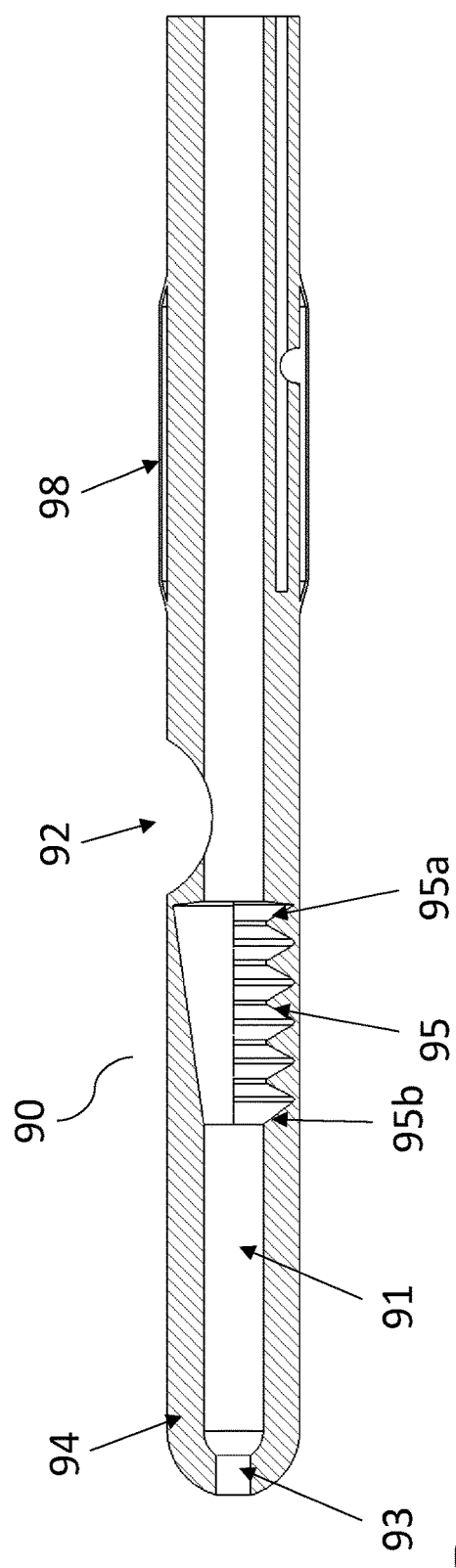
FIG. 9B shows a cross-sectional view, along section A-A, of the embodiment of FIG. 9A.

FIGS. 9A-9B show the embodiment of FIGS. 8A-8B while further including a second flexibility region 95 comprising inner wall cutouts of increasing depth distally to proximally. For example, the inner wall cutouts may be aligned with the descending inner wall thickness shown in FIG. 9B, which is a cross-sectional view of FIG. 9A along section A-A. Further, distal to aperture 92, the second flexibility region 95 includes a series of internal grooves with a sawtooth profile. The distance between the ridges and valleys of the sawtooth 95a, 95b, as well as the internal height of the ridges and valleys may be graded, stepped, gradual, etc. Alternatively, or additionally, the cutouts may gradually increase in depth moving proximally or there may be abrupt changes in depth moving proximally toward the first flexibility region 92. The depth may range from about 0.25-0.5 mm to about 1-2 mm. The percent volume of material removed to create the second flexibility region 85 may be about 10% to about 90%. The cutouts may be substantially triangular (base of triangular cutout being on a posterior side of the catheter body), substantially rectangular, substantially slits, etc. In some embodiments, the cutouts in an inner wall thickness are without the descending wall thickness described in connection with FIGS. 8A-8B. As above, the catheter body 90 defines a lumen 91 therethrough, includes, but does not require, retention balloon 98 (in an uninflated state), and distal tip 94. Distal tip 94 defines aperture 93 for passing a guide wire therethrough, draining liquid from an organ, or irrigating tissue in an organ.

FIGS. 10A-10B show the embodiment of FIGS. 7A-7B while further including a second flexibility region comprising an anterior portion 105a of the catheter body 100 that has a durometer or material that differs from that of: a posterior portion 105b of the catheter body 100 and/or a proximal section of the catheter body 100 (e.g., proximal to the balloon 108 or proximal to aperture 102). The anterior portion 105a may be substantially an anterior half, an anterior surface, an anterior quarter, etc. The durometer of the second flexibility region may be lower than a durometer (softer) of the rest of the catheter body 100. Alternatively, or additionally, the material of the anterior portion 105a may be different than the posterior portion such that the anterior portion 105a is softer in material properties than the posterior portion. As shown in FIG. 10B, which is a cross-sectional view of FIG. 10A along section A-A, the second flexibility region 105a extends from a distal tip 104 proximally beyond or past distal aperture 102. The second flexibility region 105a may increase in flexibility distally to proximally, such that the lowest flexibility is at the distal tip 104 and the highest flexibility is at the proximal end of the second flexibility region. Alternatively, the second flexibility region 105a may include two low flexibility regions flanking a central high flexibility region, the high flexibility region being centered on, surrounding, or at least proximal to distal aperture 102. As above, the catheter body 100 defines a lumen 101 therethrough, includes, but does not require, retention balloon 108 (in an uninflated state), and distal tip 104. Distal tip 104 defines aperture 103 for passing a guide wire therethrough, draining liquid from an organ, or irrigating tissue in an organ.

FIGS. 11A-11B show the embodiment of FIGS. 10A-10B but with the second flexibility region 115a only extending to a distal side or end of distal aperture 112. The second flexibility region comprises an anterior portion 115a of the catheter body 110 that has a durometer or material that differs than a posterior portion 115b of the catheter body 110. The anterior 115a portion may be substantially an anterior half, an anterior surface, an anterior quarter, etc. The durometer of the second flexibility region 115a may be a lower durometer (softer) than the rest of the catheter body 110. Alternatively, or additionally, the material of the anterior portion 115a may be different than the posterior portion 115b such that the anterior portion 115a is softer in material properties than the posterior portion. As shown in FIG. 11B, which is a cross-sectional view of FIG. 11A along section A-A, the second flexibility region 115a extends from a distal tip 114 to a distal end of distal aperture 112. The second flexibility region 115a may abut the distal aperture 112 or may just be proximal to but not abutting the distal aperture 112. The second flexibility region 115a may increase in flexibility distally to proximally, such that lowest flexibility is at the distal tip 114 and the highest flexibility is at the proximal end of the second flexibility region. Alternatively, the second flexibility region 115a may include two low flexibility regions flanking a central high flexibility region. As above, the catheter body 110 defines a lumen 111 therethrough, includes, but does not require, retention balloon 118 (in an uninflated state), and comprises distal tip 114. Distal tip 114 defines aperture 113 for passing a guide wire therethrough, draining liquid from an organ, or irrigating tissue in an organ.

Figure 12C:
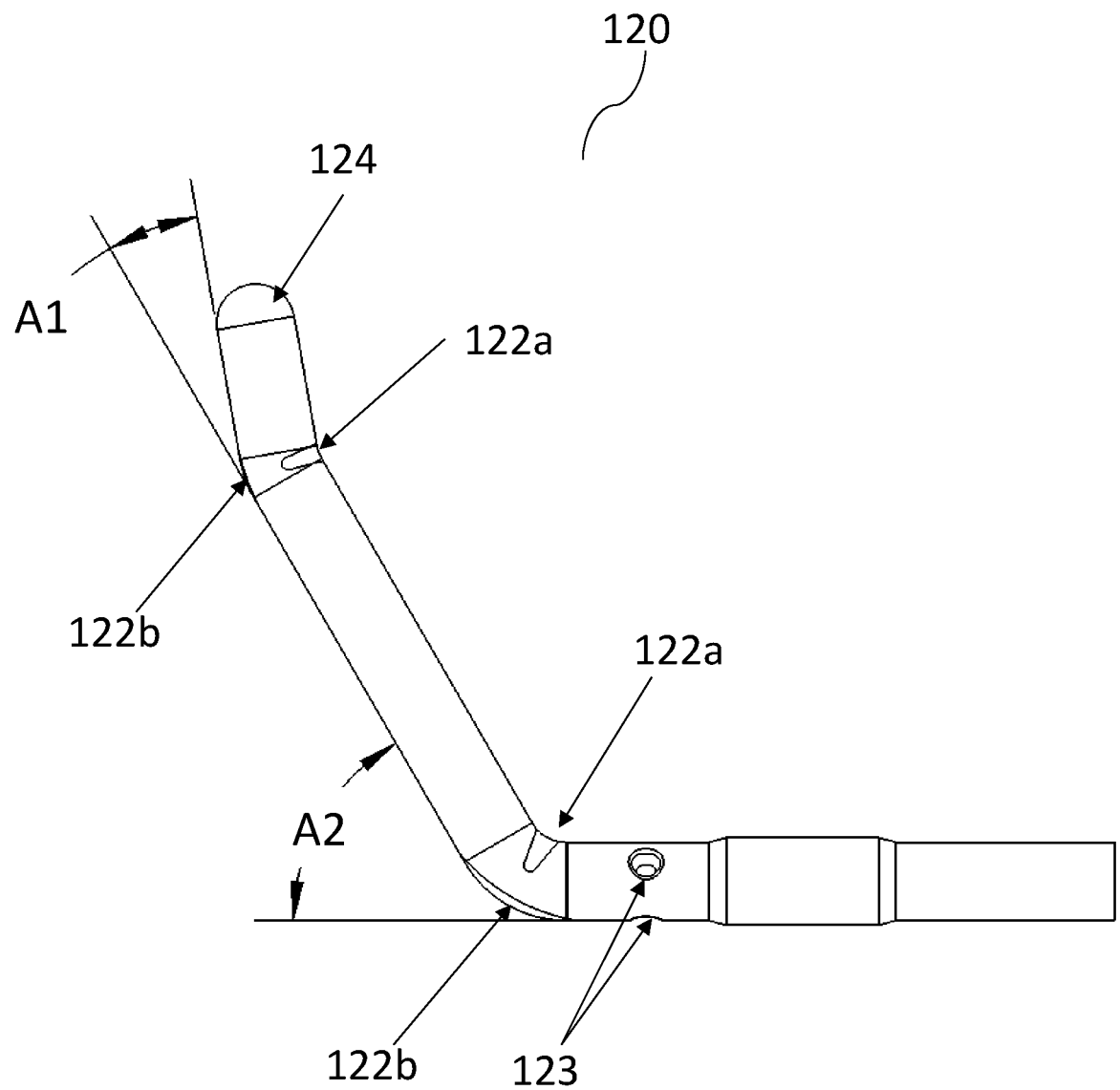
FIG. 12C shows a side view of the embodiment of FIG. 12A in a bent configuration.
Figure 12D:
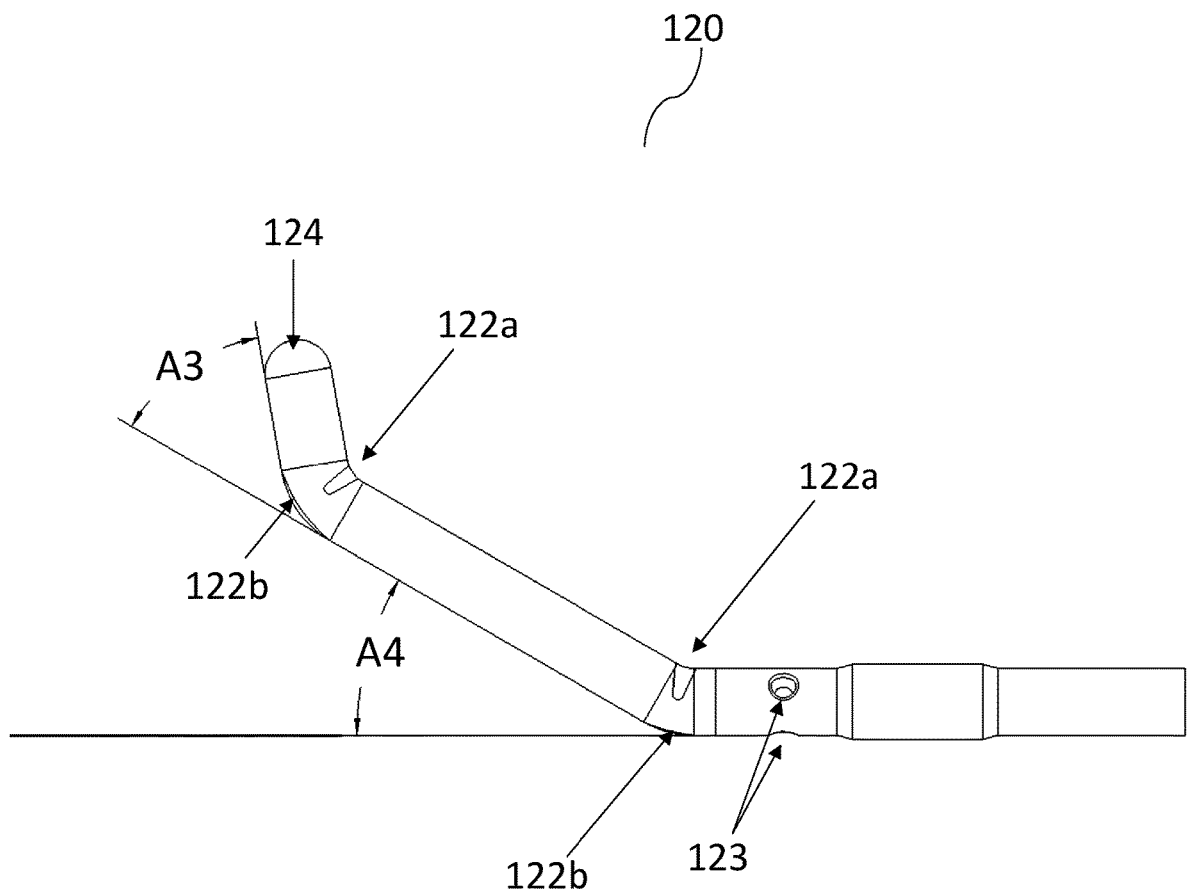
FIG. 12D shows a side view of the embodiment of FIG. 12A in another bent configuration.

FIGS. 12A-12D show another embodiment of a flexible catheter. As shown in FIGS. 12A-12B, elongate body 120 defines a lumen 121 therethrough, defines one or more apertures 123 (e.g., for irrigating tissue, draining liquid, etc.), and includes distal tip or distal end 124. The elongate body 120 further includes one or more flexibility regions 122a on an anterior portion of catheter 120. For example, flexibility region 122a may include a low durometer fill material with one or more relief apertures 127 defined by region 122a. The relief apertures 127 may relieve strain and/or enhance flexibility at region 122a. As shown in FIG. 12B, which is a cross-sectional view of FIG. 12A along section A-A, the relief apertures 127 penetrate the anterior side wall, but one of skill in the art will appreciate that they do not have to penetrate the sidewall to increase flexibility at that region. The cut depth percentage 125 of flexibility regions 122a may be about 30% to about 70% of the outer diameter 5800. The percent volume that the low durometer fill material occupies in flexibility regions 122a may be about 5% to about 50% of the outer diameter 5800. As shown in FIG. 12A and as applied to any flexibility region described elsewhere herein, each flexibility region 122a may include a unique shape, structure, and/or filler material. In this example, one flexibility region has a more circular appearance or shape while the other flexibility region has a more oval appearance or shape.

Further, as best shown in FIG. 12B, the elongate body 120 further includes one or more flexibility regions 122b on a posterior portion of catheter 120. Flexibility regions 122b may comprise a low durometer filler material, one or more relief apertures, convexity, concavity, etc. The cut depth percentage 129 of flexibility regions 122b may be about 5% to about 30%. The percent volume that the low durometer fill material occupies in flexibility regions 122a may be about 5% to about 40%. In some embodiments, the one or more anterior flexibility regions are substantially the same as the posterior flexibility regions; in other embodiments, the one or more anterior flexibility regions are substantially different than the one or more posterior flexibility regions. As above, the catheter body 120 includes, but does not require, retention balloon 128 (shown in an uninflated state).

The flexible characteristics of catheter 120 are shown in FIGS. 12C-12D. The catheter 120 has increased bendability at flexible regions 122a, 122b. For example, at flexible region 122a, the catheter 120 may bend at an angle A1, A2, A3, or A4, each being about 10 degrees to about 90 degrees; about 20 degrees to about 80 degrees; about 20 degrees to about 60 degrees; about 15 degrees to about 50 degrees; about 50 degrees to about 90 degrees; about 10 degrees to about 40 degrees; about 20 degrees to about 40 degrees; about 5 degrees to about 50 degrees; about 5 degrees to about 30 degrees; about 10 degrees to about 30 degrees; about 15 degrees to about 25 degrees; etc. In some embodiments, the cumulative bend of A1 and A2 or A3 and A4 is about 20 degrees to about 200 degrees; about 30 degrees to about 90 degrees; about 75 degrees to about 85 degrees; about 80 degrees to about 180 degrees; substantially 80 degrees; etc. The flexible region of the catheter 120 may comprise the distal most or distal portion that is a length from the distal tip 124, the length being about 15 mm to about 60 mm; about 30 mm to about 55 mm; about 50 mm to about 70 mm; about 40 mm to about 80 mm; about 50 mm to about 60 mm; etc. In some embodiments, angle A2 is greater than angle A1. In other embodiments, A1 is greater than A2. Further, in some embodiments, angle A4 is greater than angle A3. In other embodiments, A3 is greater than A3. In still further embodiments, A2 may substantially equal A1 or A3 may substantially equal A4. As above, the catheter body 120 defines a lumen 121 therethrough and one or more apertures 123 for draining/irrigating, etc. Further, catheter 120 includes, but does not require, retention balloon 128 (in an uninflated state), and distal tip 124.

Figures 13A, 13B:
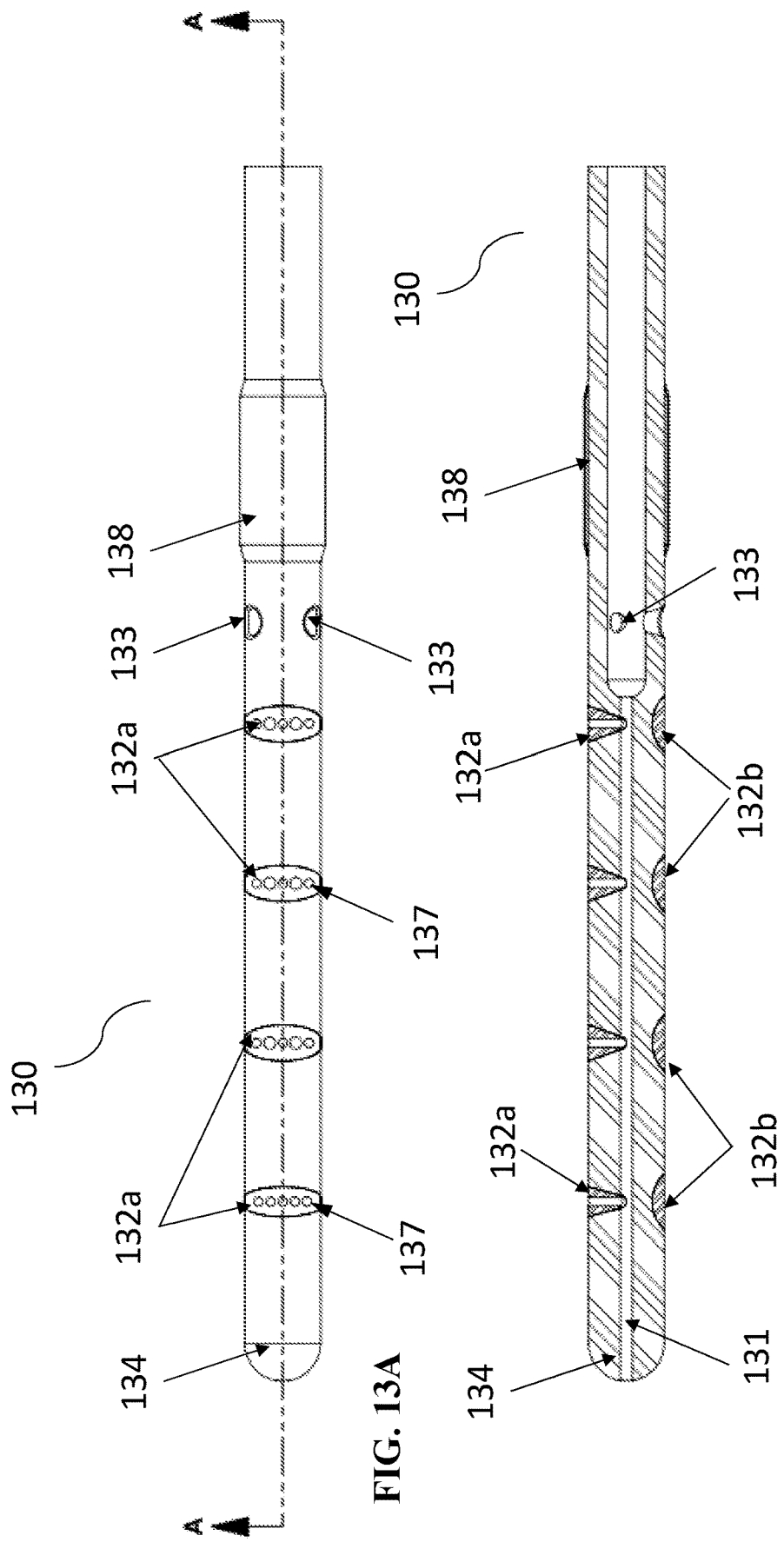
FIG. 13A shows an anterior view of another embodiment of a flexible catheter.
FIG. 13B shows a cross-sectional view, along section A-A, of the embodiment of FIG. 13A.
Figure 13C:
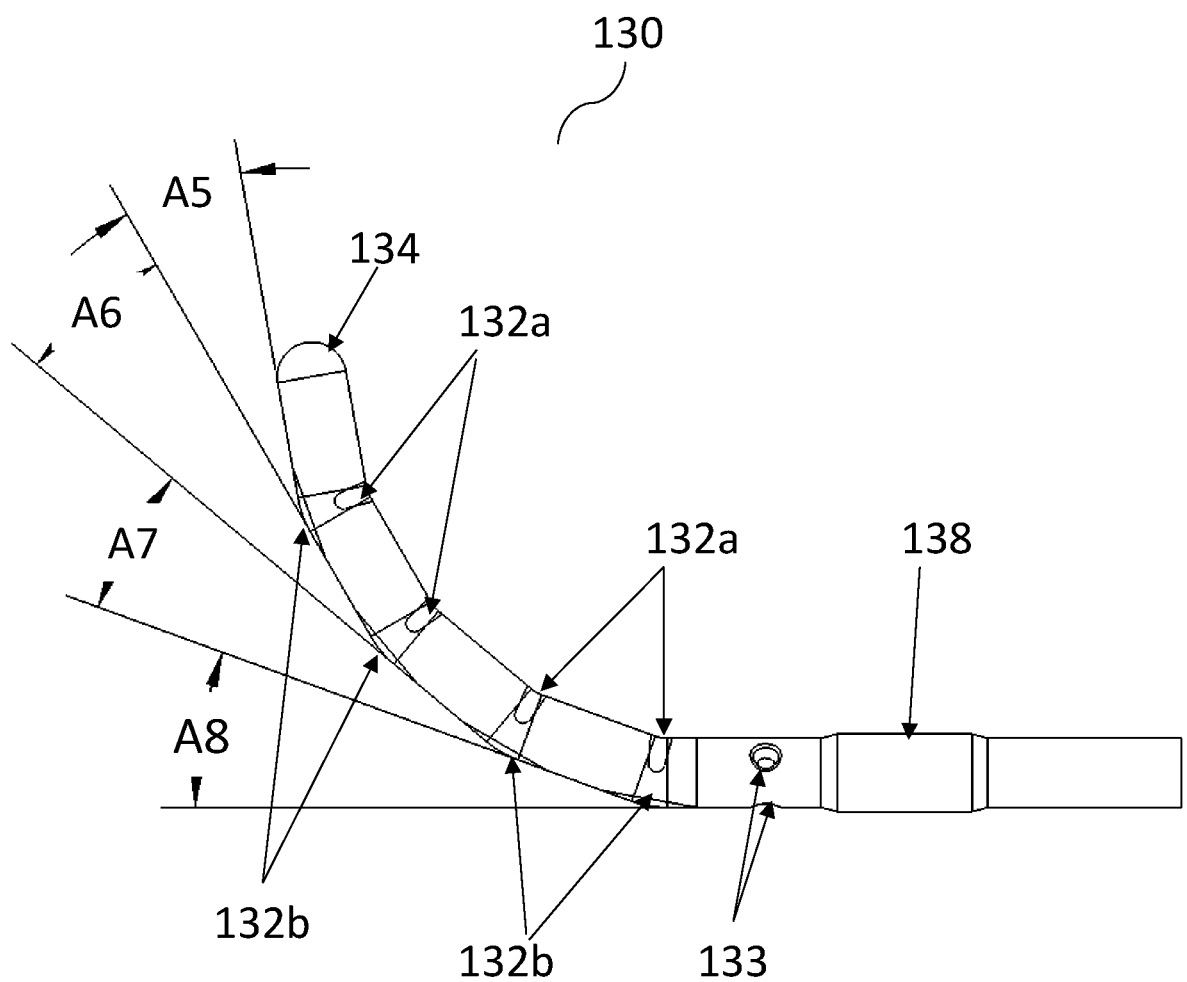
FIG. 13C shows a side view of the embodiment of FIG. 13A in a bent configuration.

FIGS. 13A-13C are similar to the embodiment shown in FIGS. 12A-12D, except in this embodiment, catheter or elongate body 130 comprises a plurality of anterior flexibility regions 132a and a plurality of posterior flexibility regions 132b. In this exemplary, non-limiting embodiment, there are four anterior and four posterior flexibility regions; although one of skill in the art will appreciate that the number, spacing, shape, and/or composition of the flexibility regions may be altered without departing from the original scope of this disclosure. In some embodiments, the posterior and/or anterior flexibility regions 132a, 132b include or comprise therein a low durometer fill material with one or more relief apertures 137 defined by region 132a or 132b. The relief apertures 137 may relieve strain and/or enhance flexibility at region 132a. As shown in FIG. 13A and as applied to any flexibility region described elsewhere herein, each flexibility region 132a may include a unique shape, structure, and/or filler material. In this example, the anterior flexibility regions 132a have a substantially oval appearance or shape while the posterior flexibility region 132b has a more circular appearance or shape. In some embodiments, there may be equal spacing between adjacent flexibility regions 132a; in other embodiments, there may be irregular spacing between adjacent flexibility regions 132a. For example, there may be about 5 mm to about 20 mm; about 10 mm to about 15 mm; about 8 mm to about 18 mm; about 12 mm to about 15 mm; etc. between adjacent flexibility regions 132a. The most distal flexibility region may be spaced apart from the distal tip 134 by about 1 mm to about 10 mm; about 3 mm to about 8 mm; substantially 5 mm; about 5 mm to about 15 mm; etc. Further, in some embodiments, flexibility region 132b is transversely, but not axially, offset from flexibility region 132a; in other embodiments, flexibility region 132b is transversely and axially offset from flexibility region 132a. In still other embodiments, flexibility region 132b is axially, but not transversely, offset from flexibility region 132a, resulting in more anterior flexibility regions.

The flexible characteristics of catheter 130 are shown in FIG. 13C. The catheter 130 bends at flexible regions 132a, 132b. For example, at flexible region 132a, the catheter 130 may bend at an angle A5, A6, A7, or A8 of about 1 degree to about 50 degrees; about 10 degrees to about 40 degrees; about 15 degrees to about 25 degrees; about 10 degrees to about 30 degrees; about 18 degrees to about 23 degrees; etc. In some embodiments, the cumulative bend of A5, A6, A7, and A8 is about 15 degrees to about 200 degrees; about 60 degrees to about 90 degrees; about 75 degrees to about 85 degrees; substantially 80 degrees; etc. In some embodiments, angles A3 (FIG. 12D), A5, etc. may help promote guidance during insertion. The flexible region of the catheter 130 may comprise the distal most or distal portion that is about 15 mm to about 60 mm; about 30 mm to about 55 mm; about 50 mm to about 70 mm; about 40 mm to about 80 mm; about 50 mm to about 60 mm; etc. from the distal tip 134. As above, the catheter body 130 (in FIG. 13B, which is a cross-sectional view of FIG. 13A along section A-A) defines a lumen 131 for passing a guide wire therethrough, draining liquid from an organ, or irrigating tissue in an organ and one or more apertures 133 for draining/irrigating, etc. Further, catheter 130 includes, but does not require, retention balloon 138 (in an uninflated state), and distal tip 134.

FIGS. 14A-14B (FIG. 14B being a cross-sectional view of FIG. 14A along section D-D) are similar to the embodiment of FIGS. 13A-13B, except in the embodiment of FIGS. 14A-14B, there are a plurality of anterior flexibility regions 142a and a plurality of posterior flexibility regions 142b that may be blind holes, concave sections in an outer diameter of the catheter, convex sections in an outer diameter of the catheter, sections of different material than the rest of the catheter body, etc. In this exemplary, non-limiting embodiment, there are nine anterior and nine posterior flexibility regions; although one of skill in the art will appreciate that the number, spacing, shape, and/or composition of the flexibility regions may be altered without departing from the original scope of this disclosure. The catheter 140 may similarly bend to that of FIGS. 12A-13C, for example with a cumulative bend of about 15 degrees to about 200 degrees; about 60 degrees to about 90 degrees; about 75 degrees to about 85 degrees; substantially 80 degrees; etc. As above, the catheter body 140 defines a lumen 141 for passing a guide wire therethrough, draining liquid from an organ, or irrigating tissue in an organ and one or more apertures 143 for draining/irrigating, etc. Further, catheter 140 includes distal tip 144 and optionally, retention balloon 148 (shown in an uninflated state).

Figure 15C:
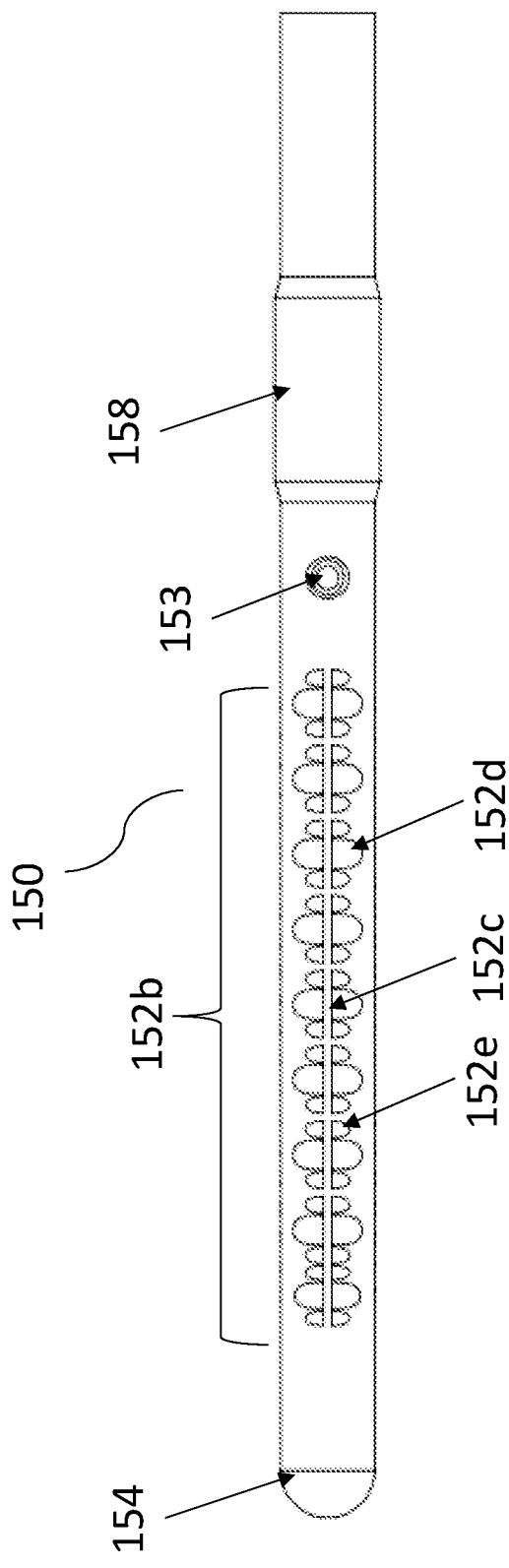
FIG. 15C shows a posterior view of the embodiment of FIG. 15A.
Figure 15D:
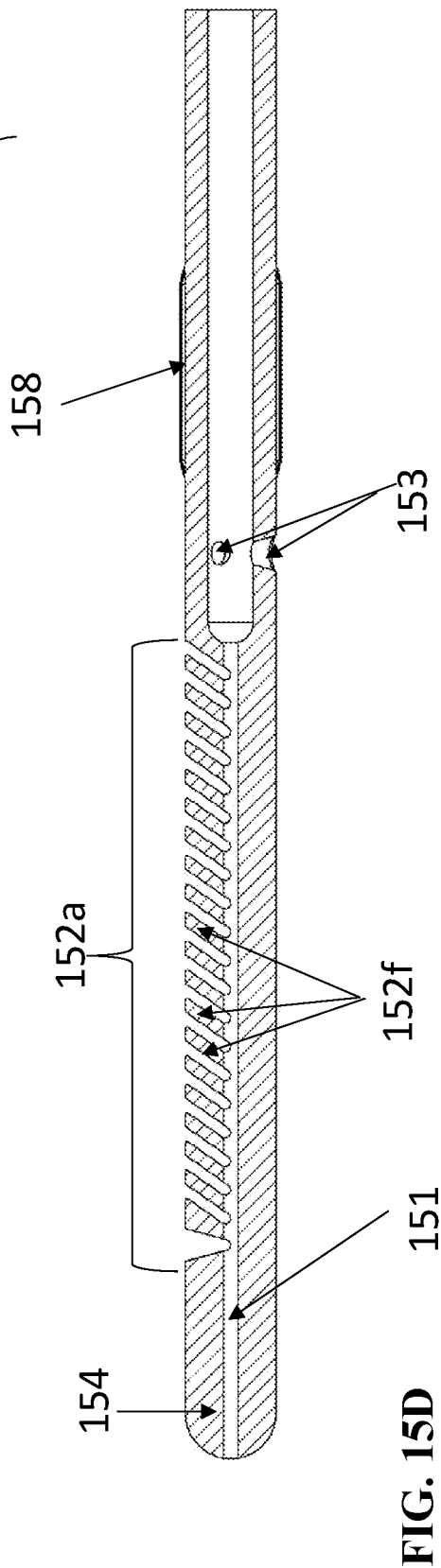
FIG. 15D shows a cross-sectional view, along section D-D, of the embodiment of FIG. 15A.

FIGS. 15A-15D show another embodiment of a flexible catheter 150 comprising one or more anterior flexibility regions 152a and/or one or more posterior flexibility regions 152b. For example, the one or more flexibility regions 152a may comprise a series or a plurality of slits, apertures, or the like separated by one or more flanges 152f, as shown in FIG. 15D. For example, a depth of each slit may be about 25% to about 75% of the catheter's diameter and a width of each slit may be about 0.25 to about 2 mm. The length of the region 152a may be about 10 mm to about 50 mm. Further, as shown in FIG. 15B, one or more of the slits or apertures, and accordingly flanges, may be at an angle A9 of about 0 degrees to about 90 degrees; about 20 degrees to about 70 degrees; about 30 degrees to about 60 degrees; about 40 degrees to about 70 degrees; etc. such that the slits or apertures are angled in the direction of the desired bend and still further, promote bending unidirectionally. Turning now to FIG. 15C, which shows the posterior flexibility region 152b. The posterior flexibility region 152b includes an axially positioned spine 152c, that may be of different material than the catheter body, etc. and one or more transversely extending apertures 152d, 152e. Axially positioned spine 152c is configured to provide a substantially continuous surface between apertures 152d, 152e to avoid deep transitions and edges. For example, axially positioned spine 152c may prevent pinching and/or abrupt transitions to reduce patient discomfort during insertion and/or removal. Flexibility region 152a may similarly (optionally) include an axially positioned spine.

The transversely extending apertures may range in size (e.g., depth, amplitude, circumference, radius, diameter, etc.), for example lengthened 152d or shortened 152e. The diameter of each aperture 152d, 152e in the long dimension may range from about 20% to about 80% of the catheter's diameter. The diameter of each aperture 152d, 152e in the short dimension may range from about 0.25 mm to about 5 mm. Further, the one or more transversely extending (from the spine) apertures may be in a pattern (e.g., every other; all lengthened; all shortened; two shortened and one lengthened; two lengthened and one shortened; etc.). The extending apertures may be blind holes, through holes, comprise a different durometer material, etc. Further, as shown in FIG. 15D and as above, the catheter body 150 defines a lumen 151 for passing a guide wire therethrough, draining liquid from an organ, or irrigating tissue in an organ and one or more apertures 153 for draining/irrigating, etc. Further, catheter 150 includes, but does not require, retention balloon 158 (in an uninflated state), and distal tip 154.

Figure 16C:
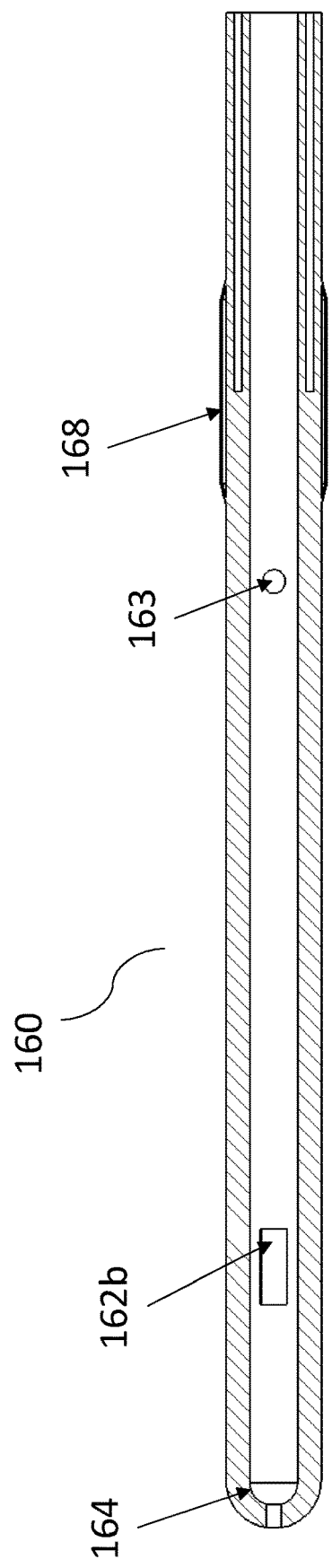
FIG. 16C shows a posterior cross section view, along section B-B, of the embodiment of FIG. 16A.
Figure 16D:
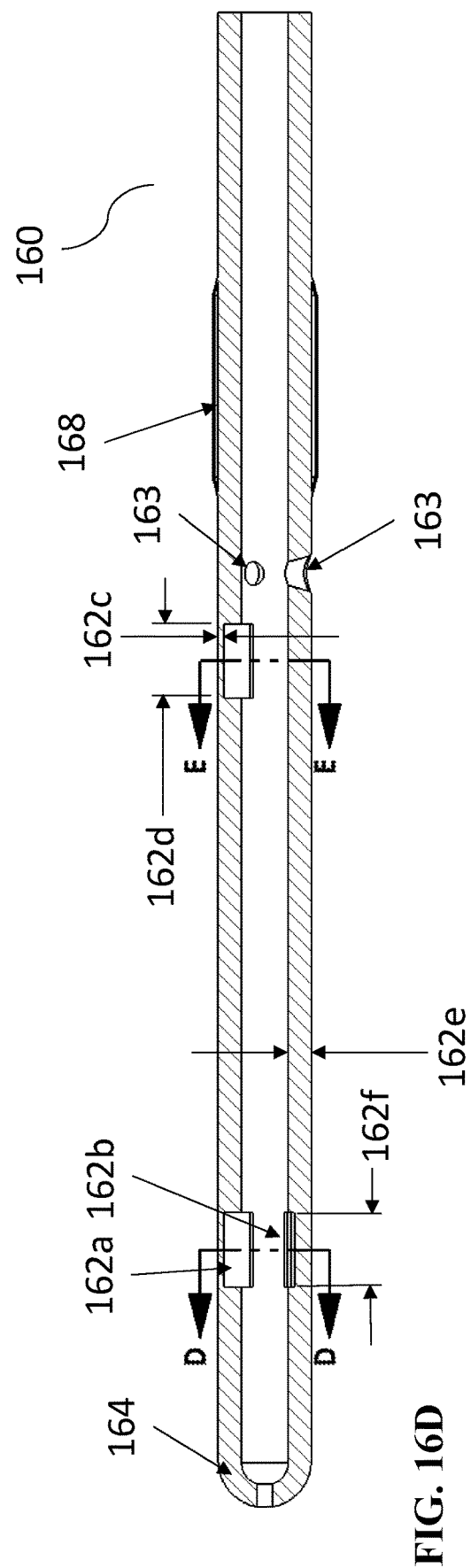
FIG. 16D shows a lateral cross-sectional view, along section C-C, of the embodiment of FIG. 16B.

In some embodiments, as shown in FIGS. 16A-16D, at least a portion of an inner wall along an inner diameter or lumen of elongate body 160 may be removed to provide one or more flexibility regions 162a, 162b. The flexibility region may be anteriorly positioned 162a or posteriorly positioned 162b or both, as shown in FIGS. 16B-16C. In this specific embodiment, there are two anterior flexibility regions and one posterior flexibility region, although one or more anterior flexibility regions and one or more posterior flexibility regions are contemplated herein. Further, as shown in FIG. 16B, which is a cross-sectional view of FIG. 16A along section AA, there may be two flexibility regions, spaced apart and distally positioned relative to one or more apertures 163. Further, as shown in FIG. 16A, since the flexibility regions 162a, 162b are interiorly disposed, they may not be visible from an external view of elongate body 160. As shown in FIG. 16D, in some embodiments, flexibility region 162b is transversely, but not longitudinally, offset from flexibility region 162a; in other embodiments, flexibility region 162b is transversely and longitudinally offset from flexibility region 162a. In still other embodiments, flexibility region 162b is longitudinally, but not transversely, offset from flexibility region 162a, resulting in more anterior flexibility regions. FIGS. 16E-16H show sectional views of FIG. 16D (along section D-D and E-E, respectively) to show how at least a portion of the sidewall 167 of the inner diameter of elongate body 160 is removed to create flexibility regions 162a, 162b. In some embodiments, the wall thickness 162c and length 162d of an anterior flexibility region 162a may be thinner than the wall thickness 162e and length 162f of a posterior flexibility region 162b to promote bending in an anterior direction. For example, as shown in FIG. 16G, wall thickness 165d is shown and the posterior wall cut depth 165b and the anterior wall cut depth 165c is shown. The anterior wall cut depth 165c may be about 5% to about 95%, about 20% to about 80%, or about 70% to about 80%. The posterior wall cut depth 165b may be about 5% to about 95%, about 5% to about 50%, or about 25% to about 35%. In other embodiments, an area or volume posteriorly and anteriorly of the flexibility regions is the same or an area or volume of the anterior flexibility region is larger than that of the posterior flexibility region to promote bending anteriorly. FIG. 16H shows the volumes of material that are removed from the anterior flexibility region 162 and posterior flexibility region 162b relative to tube 169. The percent volume of material removed 515 from the anterior flexibility region 162a is about 20% to about 30% and the percent volume of material removed 516 from the posterior flexibility region 162b is about 1% to about 10% or about 2% to about 5%, relative to the tube 169 encapsulating the regions.

Figures 16E, 16F:
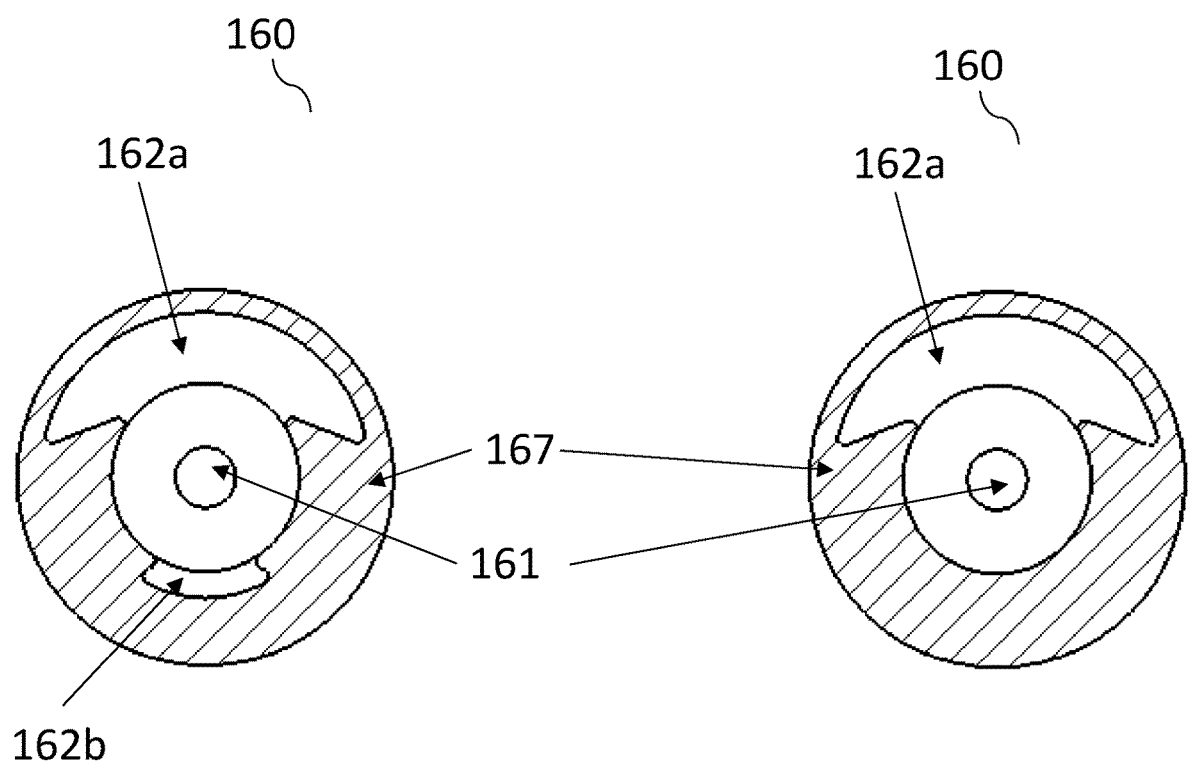
FIG. 16E shows a cross-sectional view, along section D-D, of the embodiment of FIG. 16D.
FIG. 16F shows a cross-sectional view, along section E-E, of the embodiment of FIG. 16D.
Figure 16G:
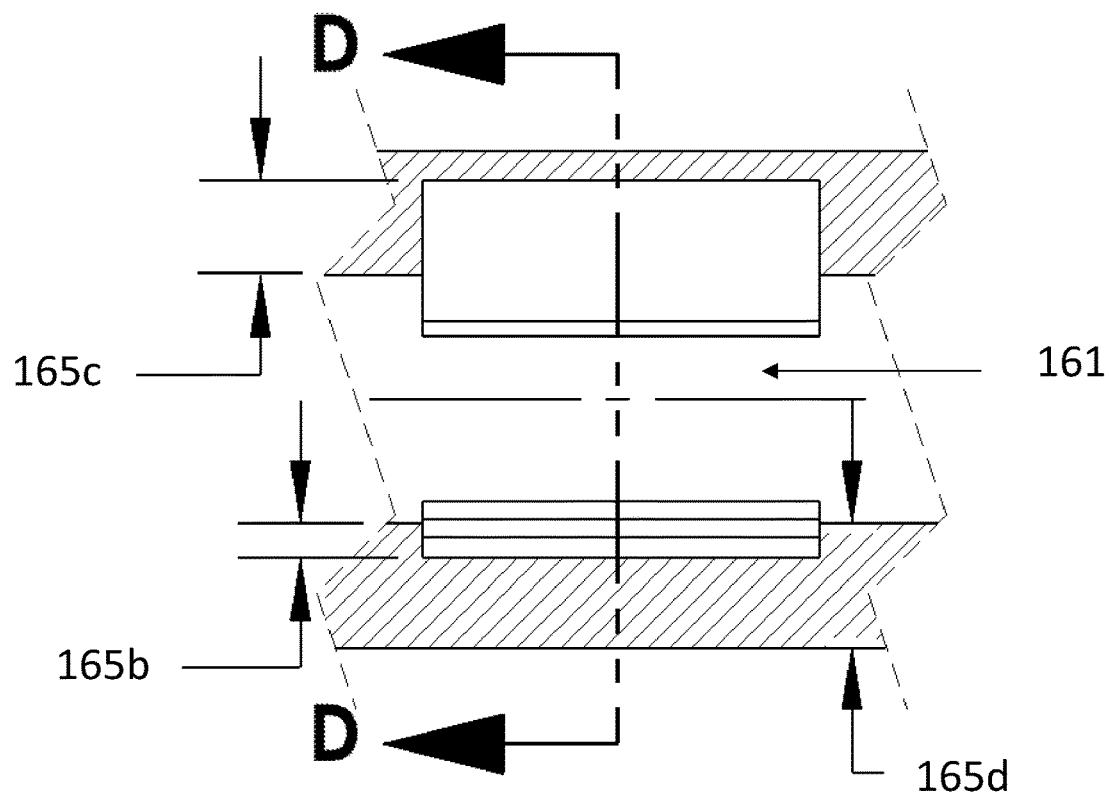
FIG. 16G shows a zoomed-in view of a portion of FIG. 16D.
Figure 16H:
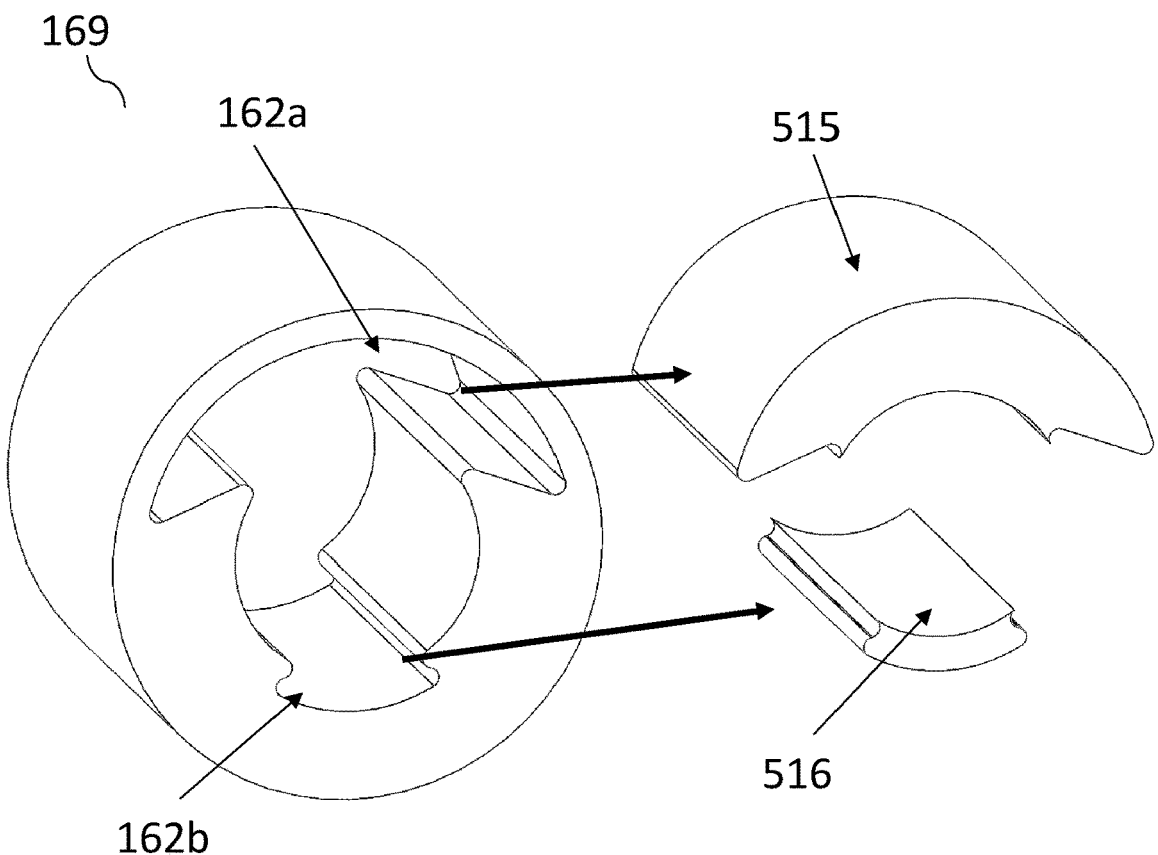
FIG. 16H shows a three-dimensional perspective view of the two flexibility regions removed from the tube to show a volume of each region.

Further, as shown in FIGS. 16E-16G and as above, the catheter body 160 defines a lumen 161 therethrough and one or more apertures 163 for draining/irrigating, etc. Further, catheter 160 includes, but does not require, retention balloon 168 (in an uninflated state), and distal tip 164.

Figure 17A:
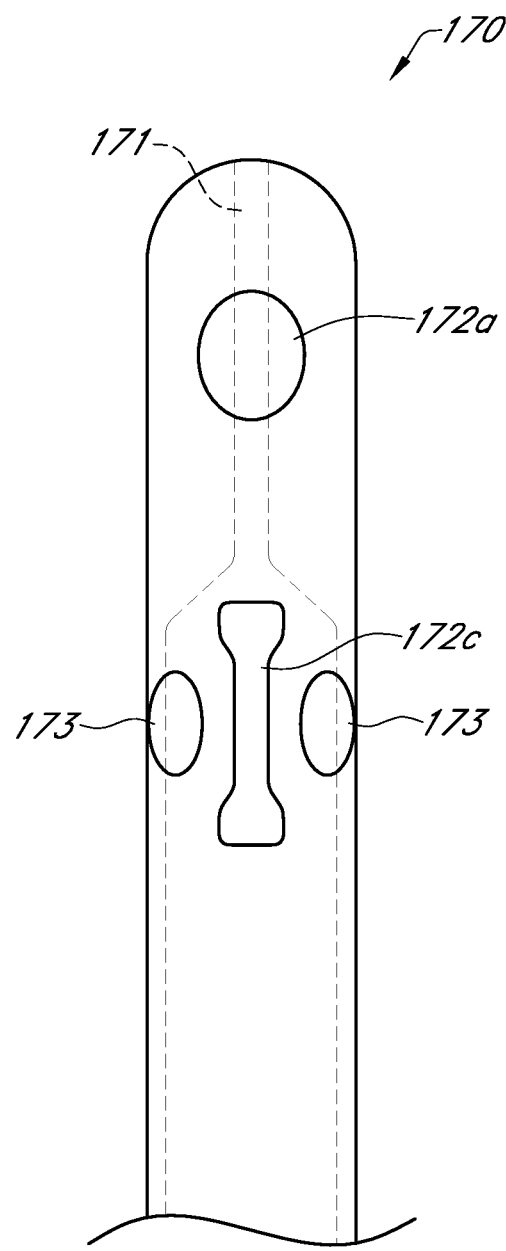
FIG. 17A shows an anterior view of another embodiment of a flexible catheter.
Figure 17B:
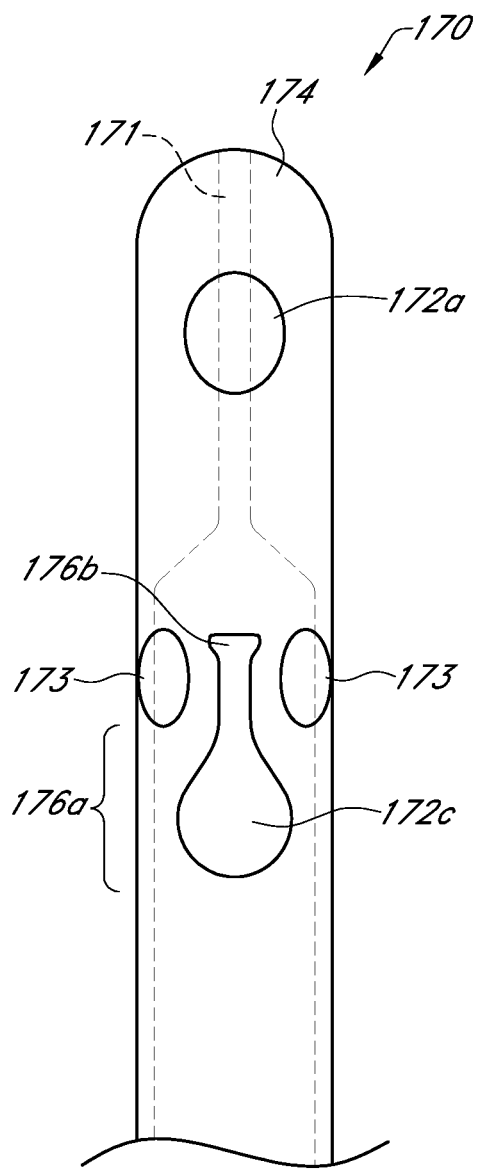
FIG. 17B shows an anterior view of another embodiment of a flexible catheter.
Figure 17C:
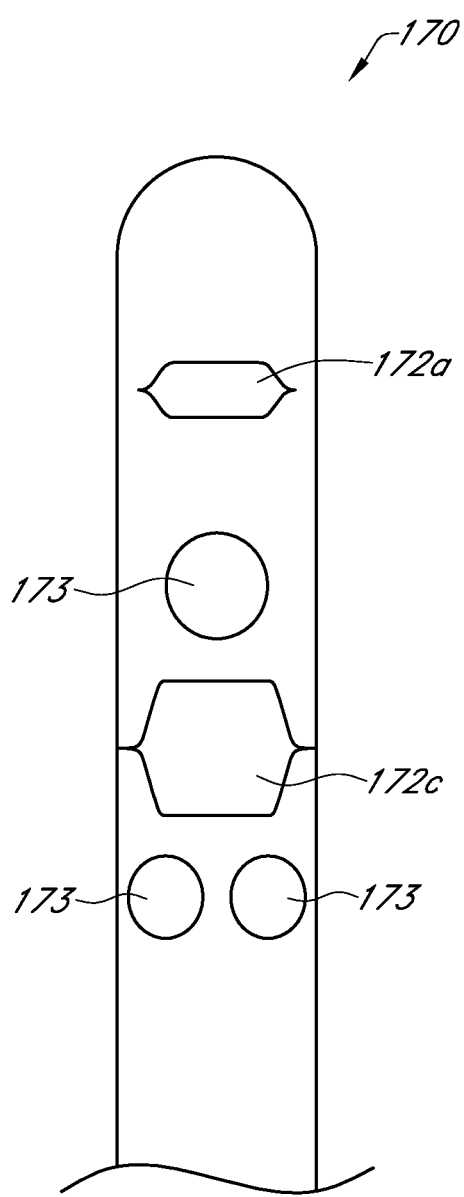
FIG. 17C shows an anterior view of another embodiment of a flexible catheter.

Turning now to FIGS. 17A-17C which show various aperture positions relative to one or more flexibility regions. For example, as shown in FIG. 17A, catheter 170 defines lumen 171 for passing a guide wire therethrough, draining liquid from an organ, or irrigating tissue in an organ and apertures 173 positioned transversely offset from flexibility region 172c but longitudinally aligned with flexibility region 172c, with respect to a longitudinal axis of catheter body 170. In such embodiments, the apertures 173 lateral to the flexibility region 172c may further enhance flexibility at this location on the catheter body 170. As shown in FIG. 17A, the catheter body 170 may further include a second flexibility region 172a located more distally on a distal end of the catheter, relative to flexibility region 172c.

Further, as shown in FIG. 17B, a bulbous end 176a of flexibility region 172c may be positioned more proximally than end 176b of flexibility region 172c, which is positioned between apertures 173 defined by catheter body 170. Such configuration of flexibility region 172c may cause or promote the distal tip 174 of catheter body 170 to bend anteriorly. As above, catheter 170 may further define a lumen 171 for passing a guide wire therethrough, draining liquid from an organ, or irrigating tissue in an organ and a second flexibility region 172a positioned more distally than flexibility region 172c.

Figure 18A:
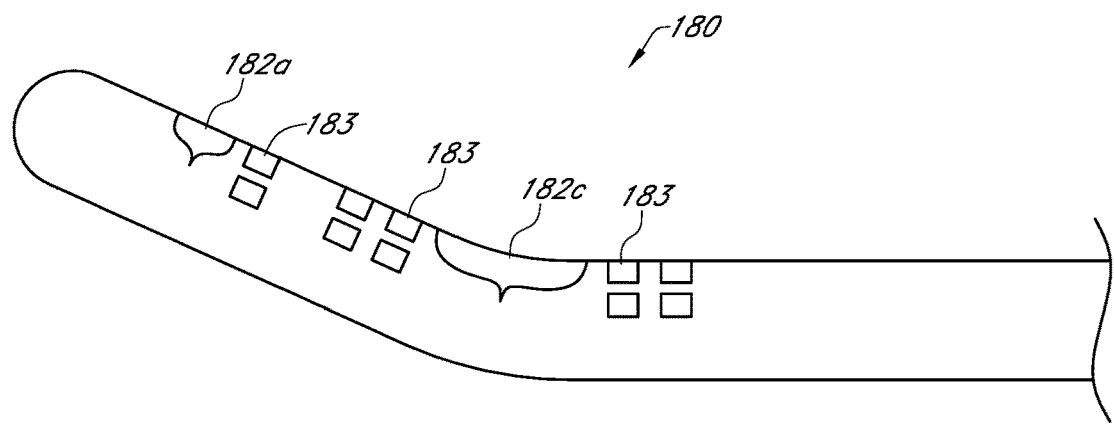
FIG. 18A shows a side view of another embodiment of a flexible catheter in a bent configuration.
Figure 18B:
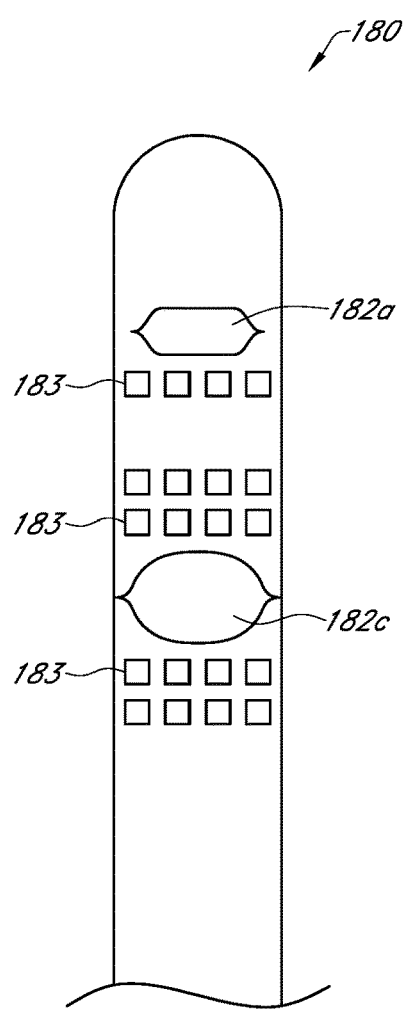
FIG. 18B shows an anterior view of the embodiment of FIG. 18A.

In still a further variation, as shown in FIG. 17C, catheter body 170 includes flexibility region 172c that is positioned between a plurality of apertures 173. For example, two apertures may be positioned more proximally than region 172c and one aperture may be positioned more distally than region 172c. In other embodiments, any number of apertures may be positioned more proximally and/or more distally that region 172c. Further, flexibility region 172c may have any shape, configuration, or otherwise that promotes bending. Elongate body 170 may further include a second flexibility region 172a positioned more distally than flexibility region 172c. As an alternative to the embodiment of FIG. 17C and as shown in FIGS. 18A-18B, apertures 183 may comprise a plurality of fenestrated eyelets or outlets defined by elongate body 180. As shown in FIGS. 18A-18B, apertures 183 are positioned between flexibility regions 182a and 182c and proximal to flexibility region 182c. Such apertures 183 may increase bendability in this region and/or simply function as irrigation, drainage, etc. apertures. Alternatively, apertures 183 may not be apertures at all but rather regions of differing durometer, material, flexibility, blind holes, etc.

Figure 19A:
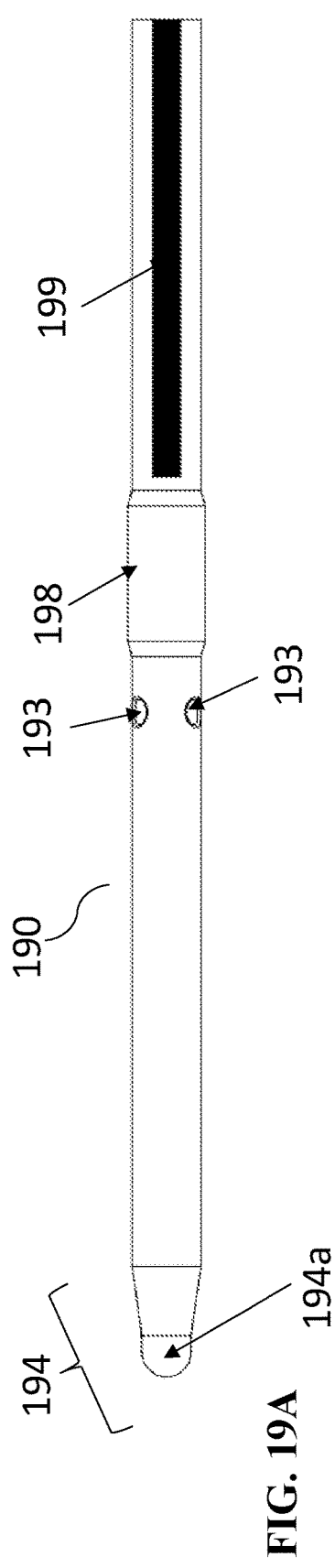
FIG. 19A shows an anterior view of another embodiment of a flexible catheter.
Figure 19B:
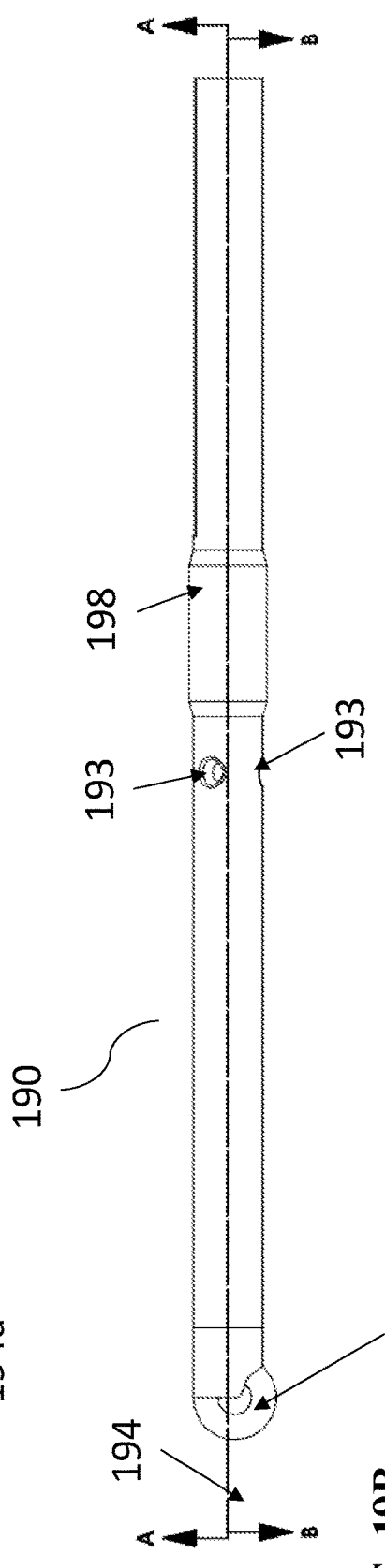
FIG. 19B shows a side view of the embodiment of FIG. 19A.
Figure 19C:
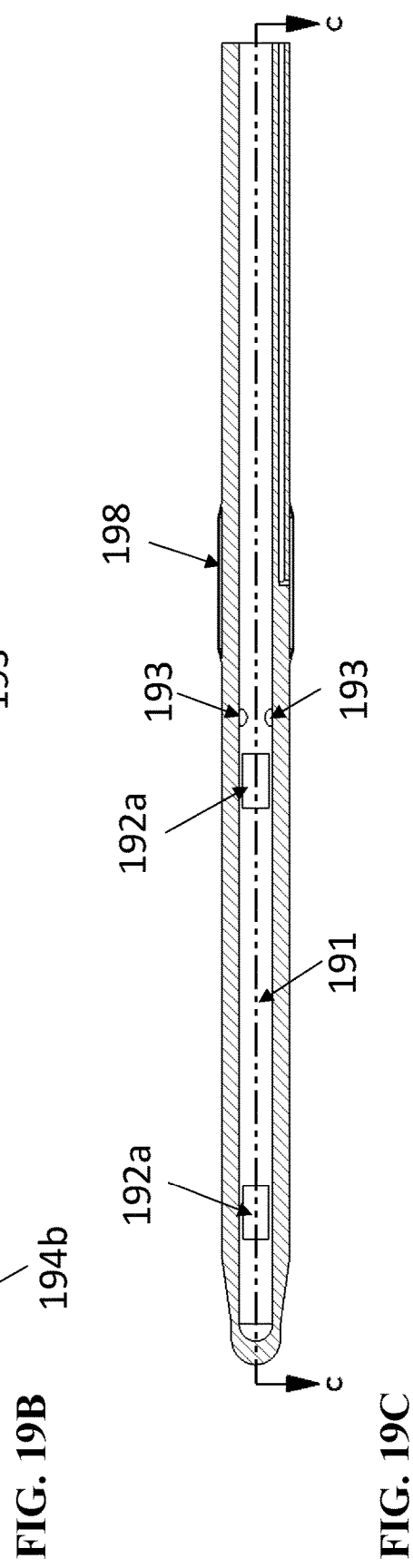
FIG. 19C shows an anterior section view, along section A-A, of the embodiment of FIG. 19B.

Turning now to FIGS. 19A-19G, which shows an embodiment similar to that of FIGS. 16A-16F, except that the elongate body 190 further includes a distal end portion 194 that comprises a narrowed end region 194a, when viewed from a side perspective, to maintain a substantially constant circumference between elongate body and bulge 194b at the distal end. The narrowed end region 194a has a diameter 194e that is less than a diameter 190d of the catheter body 190, such that a transverse circumference of the bulge 194b is substantially equal to a transverse circumference of the elongate body (e.g., at 190d). Such a relationship between the transverse circumference of the bulge and the transverse circumference of the elongate body may function to avoid stretching of the inner circumference of the vessel in which the catheter is inserted. The bulge 194b may be positioned or extend anteriorly or posteriorly to promote distal end deflection in a direction opposite of the bulge 194b. A bulge 194b may be defined as a distal end portion in which a longitudinal cross-sectional length 194c is less than a transverse cross-sectional length 194d. Further, as above in FIGS. 16A-16F and as shown in FIGS. 19A-19G, at least a portion of a sidewall along an inner diameter of elongate body 190 may be removed to provide one or more flexibility regions 192a, 192b. The flexibility region may be anteriorly positioned 192a or posteriorly positioned 192b or both, as shown in FIGS. 19C-19G. Further, as shown in FIG. 19C, which is a cross-sectional view of FIG. 19B along section A-A, there may be two flexibility regions, spaced apart and distally positioned relative to one or more apertures 193. Further, as shown in FIGS. 19A-19B, since the flexibility regions 192a, 192b are interiorly disposed, they may not be visible from an external view of elongate body 190. As shown in FIG. 19D, which is a cross-sectional view of FIG. 19B along section B-B, in some embodiments, flexibility region 192b is transversely, but not longitudinally, offset from flexibility region 192a; in other embodiments, flexibility region 192b is transversely and longitudinally offset from flexibility region 192a. In still other embodiments, flexibility region 192b is longitudinally, but not transversely, offset from flexibility region 192a, resulting in more anterior flexibility regions. FIGS. 19F-19G show cross-sectional views of FIG. 19E to show how at least a portion of the sidewall 197 (shown in FIG. 19E, which is a cross-section view of FIG. 19C along section C-C) of the inner diameter of elongate body 190 is removed to create flexibility regions 192a, 192b. Further, both views in FIGS. 19F-19G (FIG. 19F is a transverse view of FIG. 19E along section D-D and FIG. 19G is a transverse view of FIG. 19E along section E-E) show bulge 194b extending posteriorly, in this embodiment. In some embodiments, the wall thickness and length of the wall covering the interior cavity of an anterior flexibility region 192a may be greater than the wall thickness, area and length of the wall covering the interior cavity of a posterior flexibility region 192b to promote bending in an anterior direction. In other embodiments, the wall thickness, area and length posteriorly and anteriorly of the flexibility regions is the same, or the wall thickness, area and length of the posterior flexibility region is larger than that of the anterior flexibility region.

Further, as shown in FIG. 19A, a region proximal to balloon 198 may include an orientation marker 199, for example shown as a stripe. The marker may be positioned on an anterior side of the elongate body 190 so that a user can determine the orientation of the catheter, after insertion. As such, a user may then know in what direction distal deflection is occurring, because it is unidirectional in an anterior direction. Alternatively, a marker may be positioned on a posterior side of the elongate body 190 or otherwise, to communicate an orientation of the catheter during or after insertion.

Further, as shown in FIGS. 19A and 19F-19G and as above, the catheter body 190 defines a lumen 191 therethrough and one or more apertures 193 for guide wire passage/draining/irrigating, etc. Further, catheter 190 includes, but does not require, retention balloon 198 (in an uninflated state), and distal end region 194.

Figure 22D:
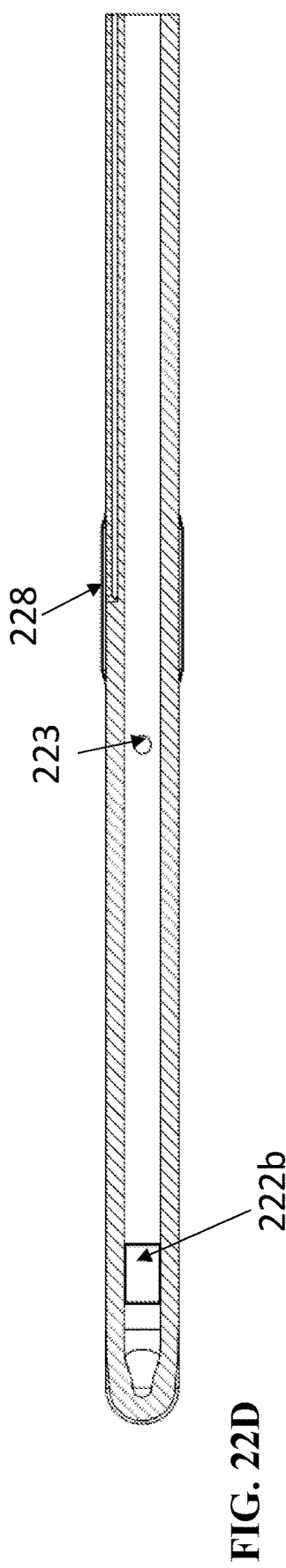
FIG. 22D shows a posterior cross-sectional view, along section B-B, of the embodiment of FIG. 22B.
Figure 22E:
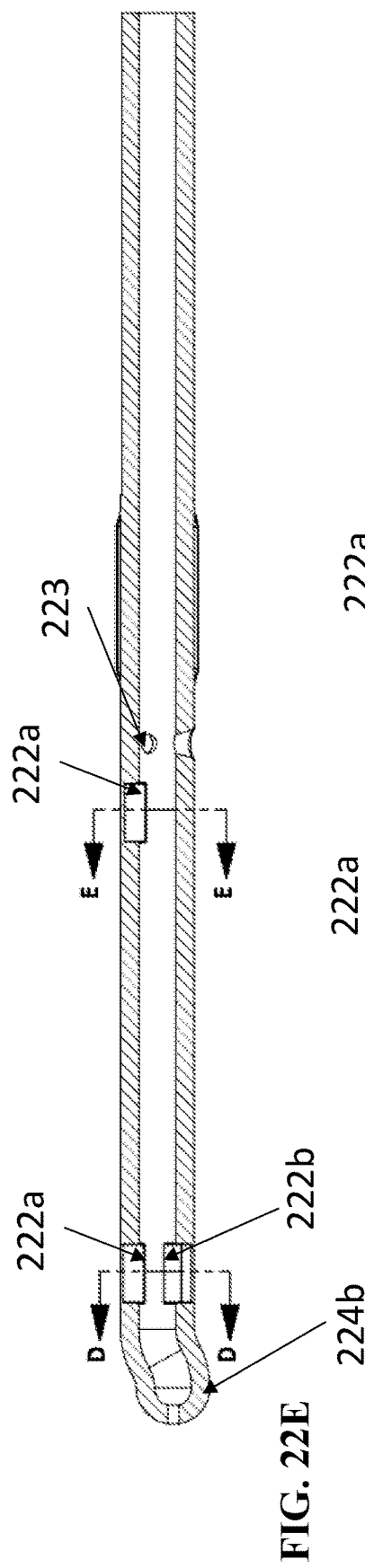
FIG. 22E shows a side sectional view, along section C-C of the embodiment of FIG. 22C.
Figure 22F:
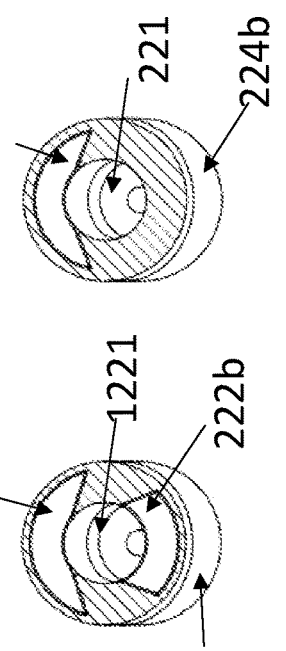
FIG. 22F shows a cross-sectional view, along section D-D, of the embodiment of FIG. 22E.
Figure 22G:
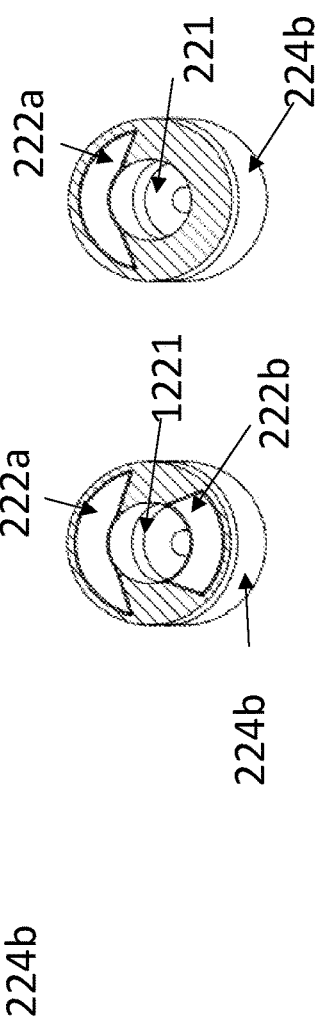
FIG. 22G shows a cross-sectional view, along section E-E, of the embodiment of FIG. 22E.

FIGS. 22A-22G show another embodiment of a flexible catheter that is similar to that of FIGS. 16A-16F, except this embodiment includes an asymmetric tip. As shown in FIGS. 22A-22C (FIG. 22C being a cross-sectional view of FIG. 22B along section A-A), elongate body 220 defining apertures 223 and lumen 221 and comprising (but not requiring) balloon 228 includes distal end region 224 and optionally marker 229, as described elsewhere herein. Distal end region is longitudinally offset 224b, as shown in FIGS. 22B and 22E. A circumference or diameter of distal end region is similar to that of the rest of the catheter body 220, but extends posteriorly (or alternatively anteriorly). For example, the longitudinal offset 224b may be about 0.5 mm to about 5 mm. The elongate body 220 further includes one or more anterior flexibility regions 222a and/or posterior flexibility regions 222b, as described elsewhere herein, at least with respect to FIGS. 16 and 19. A cross-sectional view is also shown in FIGS. 22F-22G, illustrating the flexibility regions 222a, 222b, longitudinally offset distal end 224b, and lumen 221.

Figure 23:
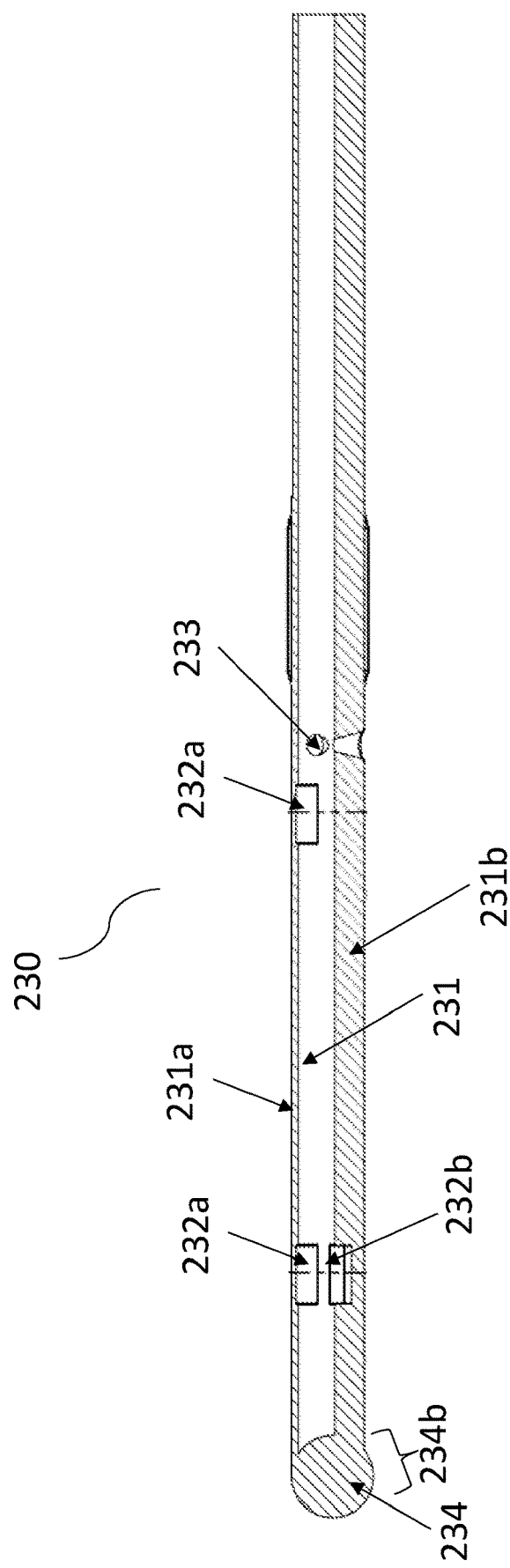
FIG. 23 shows a side-sectional view of another embodiment of a flexible catheter having an offset lumen.

Further, as shown in FIG. 23 but as also applied to any embodiment shown and/or described herein, elongate body 230 may define lumen 231 that is offset from a centerline axis of the elongate body 230. For example, an anterior inner wall 231a may be thinner than a posterior inner wall 231b or said another way, material may be added to a posterior inner wall of a lumen of elongate body 230 and/or material may be removed from an anterior inner wall of the lumen of the elongate body 230 (e.g., to maintain a desired French size of catheter). Such thinner inner wall 231a may promote unidirectional bending in an anterior direction. As one of skill in the art will appreciate, a posterior wall may also be thinner than an anterior wall to promote bending posteriorly. Further, as described above, catheter body 230 may include one or more flexibility regions, 232a, 232b and define one or more apertures 233. Elongate body 230, as shown in FIG. 23, includes distal tip 234 that includes a posterior bulge or bump 234b such that the diameter of the distal tip 234 is larger than a diameter of the elongate body 230.

FIGS. 20A-20B show another embodiment of a flexible catheter. As shown in FIG. 20B, which is a cross-section of FIG. 20A along section A-A, a plurality of flexibility regions 202a, 202b, 202c . . . 202n extends just distal of balloon 208 to near a distal end 204 of the elongate body 200. Each flexibility region 202 comprises an inner wall cutout or corrugation. Each cutout is defined by a cut depth 205 and a wavelength 203. For example, as shown in FIG. 20B, the plurality of flexibility regions 202 appear similar to a wave or in other words, appear as sinusoidal curves, although other types of cutouts (e.g., square, saw-tooth, etc.) are also envisioned. As a non-limiting example, the amplitude may be about 0.2 mm to about 0.6 mm, or about 0.4 mm; and the wavelength may be about 2 mm to about 4 mm, or about 3 mm. Optional balloon 208 is also shown and lumen 201 defined by elongate body 200 is also shown.

Figure 20G:
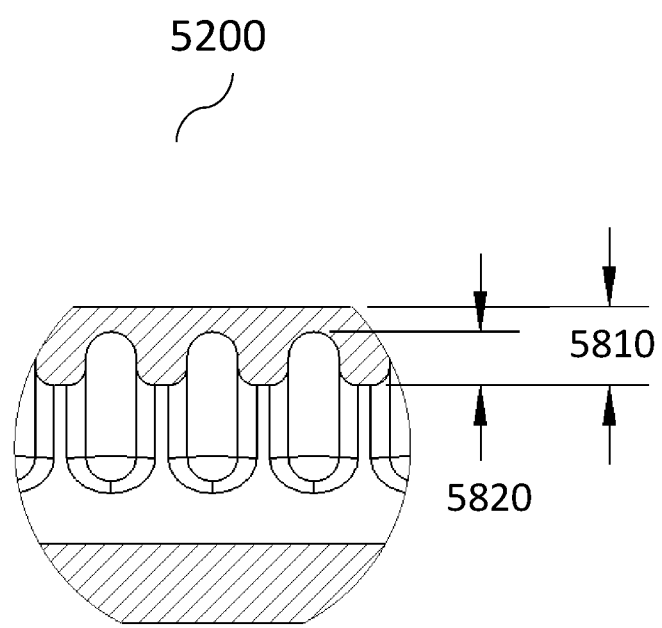
FIG. 20G shows a zoomed in view of a subset of the flexibility regions of FIG. 20C.

FIGS. 20C-20G show a similar embodiment to that of FIGS. 20A-20B, except that the elongate body 5200 defining a lumen 5201 and comprising a distal tip 5204 includes a plurality of flexibility regions, each flexibility region 5202a, 5202b, 5202c, . . . 5202n being elongated in shape along a circumferential surface of the lumen (i.e., material is removed from the lumen, the removal of which does not penetrate an exterior surface of the elongate body). FIG. 20C is a cross-sectional view. FIG. 20D shows a cross-sectional view along section B-B of FIG. 20C of flexibility region 5202a. A percent volume removed 5220 from tube 5210, as shown in FIGS. 20E-20F, for a flexibility region 5202a is about 10% to about 30% or about 15% to about 20%. FIG. 20G shows a cut depth of a flexibility region relative to a wall thickness. The wall thickness 5810 of the catheter 5200 is 100% and the cut depth percentage 5820 shown is about 50% to about 75% of the wall thickness into the wall.

FIGS. 21A-21B (FIG. 21B being a cross-sectional view of FIG. 21A along section B-B) show a similar embodiment as to that of FIGS. 20A-20B, except this embodiment includes a plurality of posterior flexibility regions 216a, 216b, 216c, . . . 216n in addition to a plurality of anterior flexibility regions 212a, 212b, 212c, . . . 212n, described above in connection with FIGS. 20A-20B. However, wavelength 217 is larger than wavelength 219 and posterior cut depth 215 is shallower than anterior cut depth 213. As a non-limiting example, amplitude 213 may be about 0.2 mm to about 0.6 mm or about 0.4 mm while amplitude 215 may be about 0.1 mm to about 0.5 mm or about 0.3 mm. Further, wavelength 219 may be about 2 mm to about 4 mm, or about 3 mm while wavelength 217 may be about 4 mm to about 8 mm or about 6 mm. Alternatively, wavelengths 219, 217 may be substantially similar and amplitudes 213, 215 may be substantially similar. Further alternatively, in some embodiments, wavelength 217 may be smaller than wavelength 219 and amplitude 215 may be larger than amplitude 213. Consistent with the relationship between amplitude and wavelength, in some embodiments, as shown in FIG. 21B, there may be fewer corrugations posteriorly than anteriorly, although variations having substantially the same number or fewer anteriorly than posteriorly are also envisioned. Optional balloon 218 is also shown and lumen 211 defined by elongate body 210 is also shown.

Figure 24E:
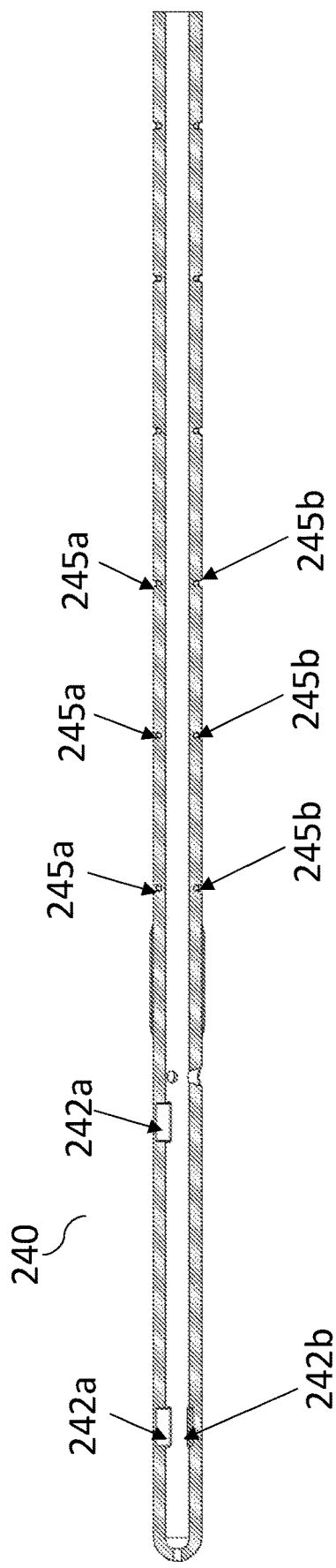
FIG. 24E shows a side sectional view of the embodiment of FIG. 24A.
Figure 24F:
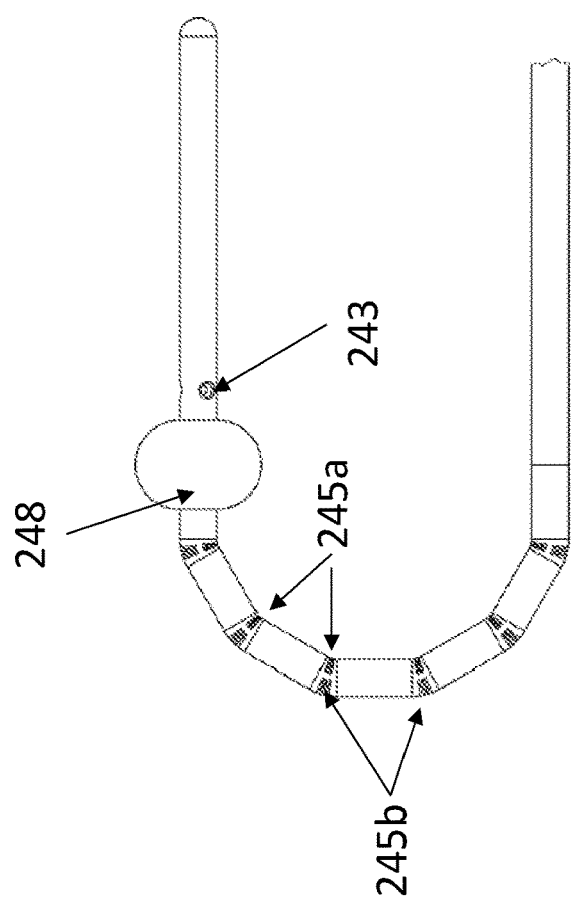
FIG. 24F shows a side view of the embodiment of FIG. 24A in a deflected state.

In any of the preceding embodiments described herein that include one or more flexibility regions in a distal segment of an elongate body, a proximal segment of the elongate body may include one or more proximal flexibility regions. For example, the various features of the elongate body 230 of FIG. 23 (flexibility regions disposed in inner wall of lumen defined by elongate body) may be combined with one or more proximal flexibility regions of elongate body 240, as shown in FIG. 24E, which includes one or more distal flexibility regions 242a, 242b in addition to one or more proximal flexibility regions 245a, 245b. Cross-sectional views of each of the flexibility regions are shown in FIGS. 24B-24D, FIG. 24B being a cross-sectional view along section A-A, FIG. 24C along section B-B, and FIG. 24D along section C-C. For example, each flexibility region 245a, 245b of elongate body 240 may include one or more grooves 247a, 247b of varying width interspersed by a meshed or web section 247c that prevents tissue from being pinched between grooves 247a and/or grooves 247b. In some embodiments, each anterior proximal flexibility region 245a is transversely aligned with each posterior flexibility region 245b. Such transverse alignment results in bendability of at least the more proximal region (or the distal region if applied to the distal region) in both anterior and posterior directions. FIGS. 24B-24D also show inflation lumen 242 defined by the elongate body 240 for inflating balloon 248, as shown in FIG. 24F. Flexibility regions 245a, 245b promote bending of the proximal segment, for example up to about 180 degrees, about 10 degrees to about 90 degrees; about 20 degrees to about 60 degrees; etc. As will be appreciated by one of skill in the art, although shown on a proximal segment of the elongate body, the flexibility regions shown in FIGS. 24A-24F may similarly be disposed on a distal segment.

Further, any of the preceding embodiments described herein may include a distal tip with tapered profile as seen from the side, similar to that shown in FIGS. 25A-25C. FIGS. 25A-25C (FIG. 25C being a cross-sectional view along section A-A of FIG. 25A) show an elongate body 250 comprising an anterior plurality of flexibility regions 252a, 252b, 252c, 252d and a posterior plurality of flexibility regions 252e, 252f, 252g and 252h. An outer diameter 256d of elongate body 250 may be greater than a projected thickness 256b of the distal tip 254 such that the outer diameter 256d of the elongate body 250 tapers in the distal segment to the outer projected thickness 256b of the distal tip 254. For example, a ratio of outer diameter 256d to outer projected thickness 256b may be about 1.0:0.8 to about 1.0:0.2. A range of the taper between outer diameter 256d and projected thickness 256b may be about 1.0:0.8 to about 1.0:0.2. The width of the tip at 256c is appropriately sized with the thickness 256b to maintain a constant transverse circumference of the tip that is equal or less than the circumference of the round main body (i.e., at 256d) to avoid stretching of the inner circumference of the anatomical lumen; the tip width 256c may also be equal to or less than the outer diameter 256d to further avoid stretching the anatomical lumen.

Figure 25D:
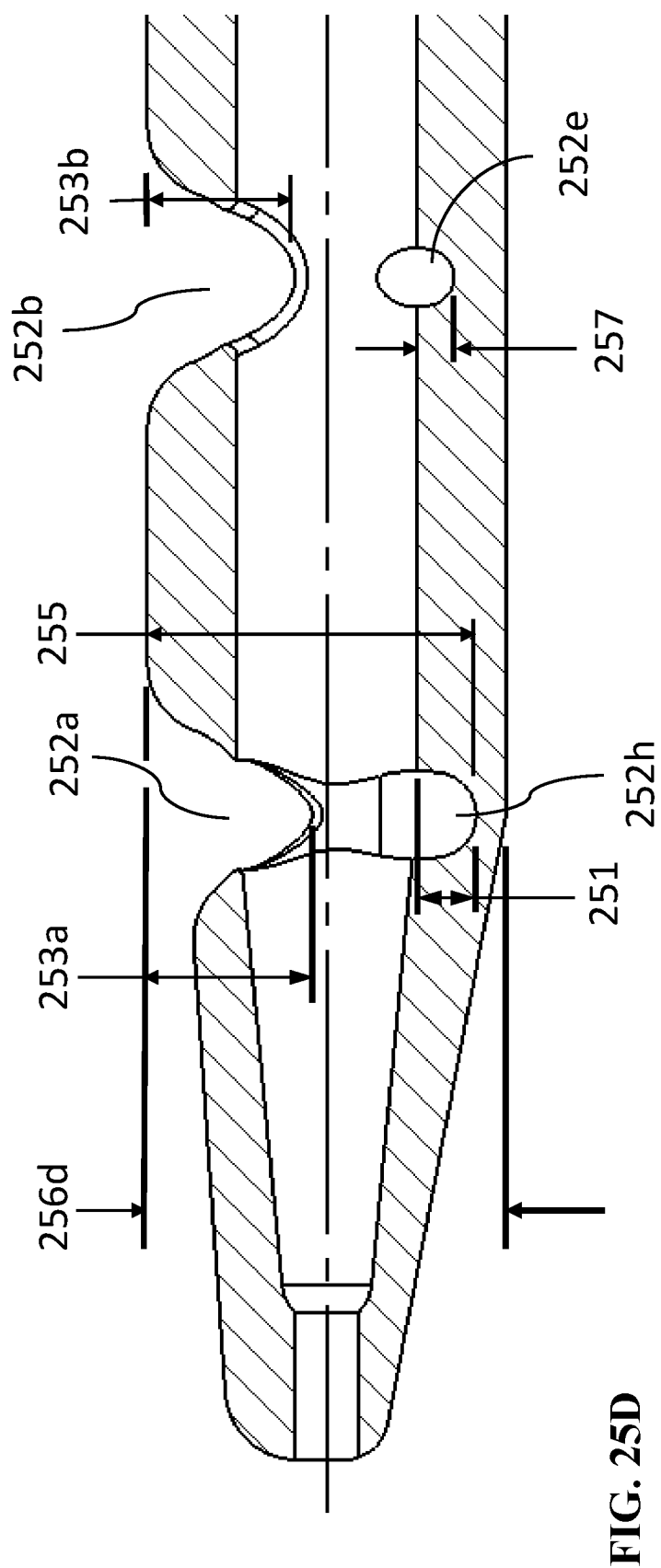
FIG. 25D shows a zoomed-in view of a portion of FIG. 25C.
Figures 25E, 25F:
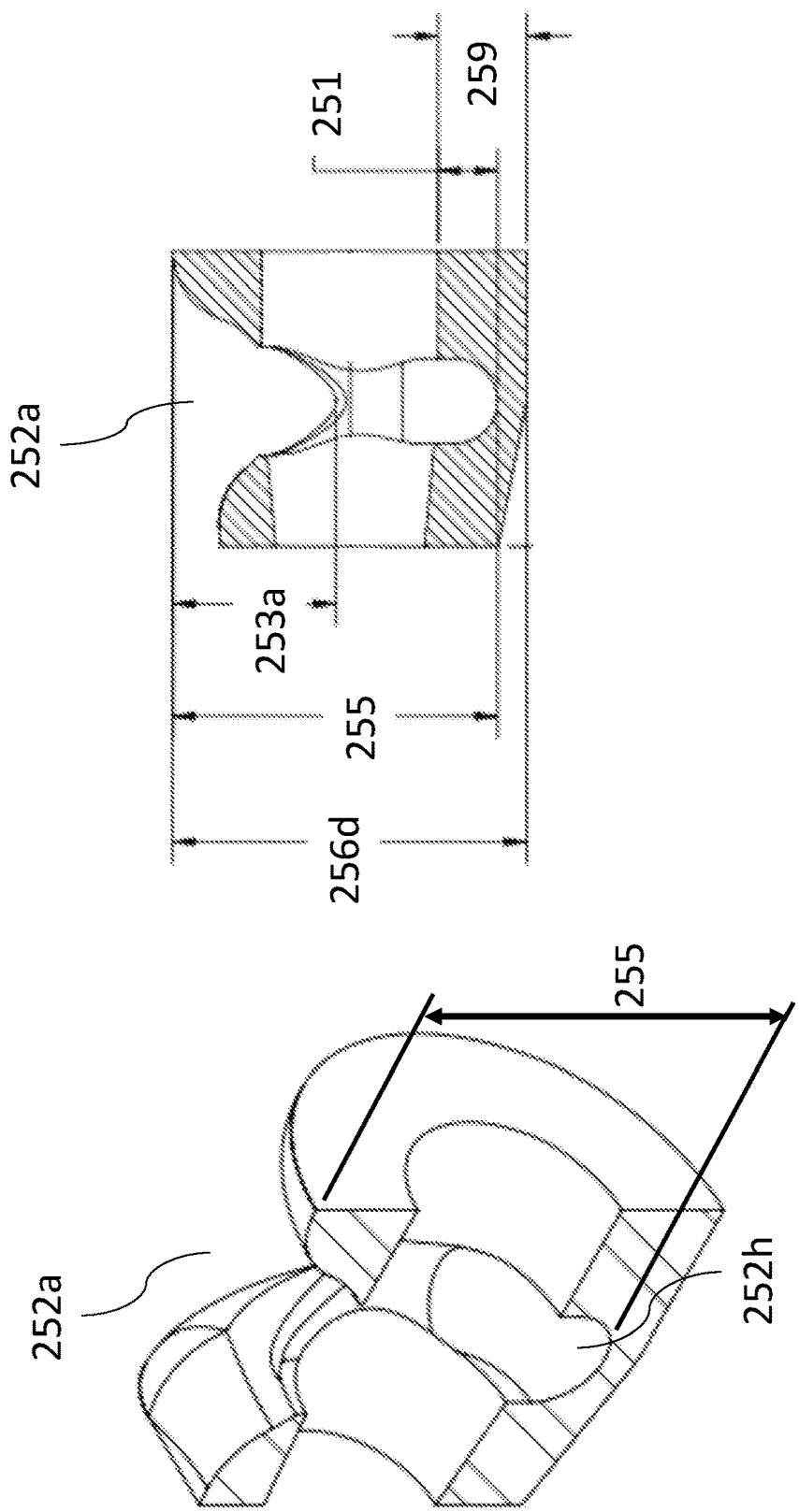
FIG. 25E shows a perspective three-dimensional view of a distal most flexibility region of the embodiment of FIG. 25B.
FIG. 25F shows a zoomed-in view of the distal most flexibility region of FIG. 25C.

FIGS. 25D-25F (FIG. 25F being a portion of section A-A of FIG. 25A) show various cut depth percentages of the flexibility regions of elongate body 250 in a cross-section zoomed-in view, in a cross-section three-dimensional view, and another cross-section zoomed-in view, respectively. A cut depth percentage at 253a and 253b, defined by the depth of the cut relative to the outer diameter 256d, of the anterior plurality of flexibility regions 252b, 252c, 252d is about 10% to about 70%. The most distal anterior flexibility region 252a may have a cut depth percentage that is greater than the cut depth percentage at 252b, 252c, 252d to facilitate the bending at the first region at 252a. For example, the cut depth percentage at 253a of the distal most anterior flexibility region may be about 25% to about 75%. An overall cut depth percentage 255 of the distal most flexibility region 252*a* is about 60% to about 95% or about 80% to about 95% or about 90% to about 95%. Further, as shown in FIGS. 25C and 25D, the optional posterior plurality of flexibility regions 252*e*, 252*f*, 252*g* and 252*h* each comprise grooves in an inner sidewall and posterior wall 281*b* of lumen 281*a* of elongate body 250. The posterior grooves 252*e*, 252*f*, 252*g* in inner sidewall 281*b* may have a cut depth percentage 257 of 5% to about 20% (relative to an outer diameter of the elongate body), with the cut depth percentage 251 (relative to an outer diameter of the elongate body) of 252*h* being equal to or greater than the cut depth percentage of 252*e*, 252*f* or 252*g*, within a range of about 5% to about 60%. The cut depth percentage 251 of flexibility region 252*h* relative to a thickness 259 of the posterior sidewall 281*b* is about 60% to about 70%.

Figure 25H:
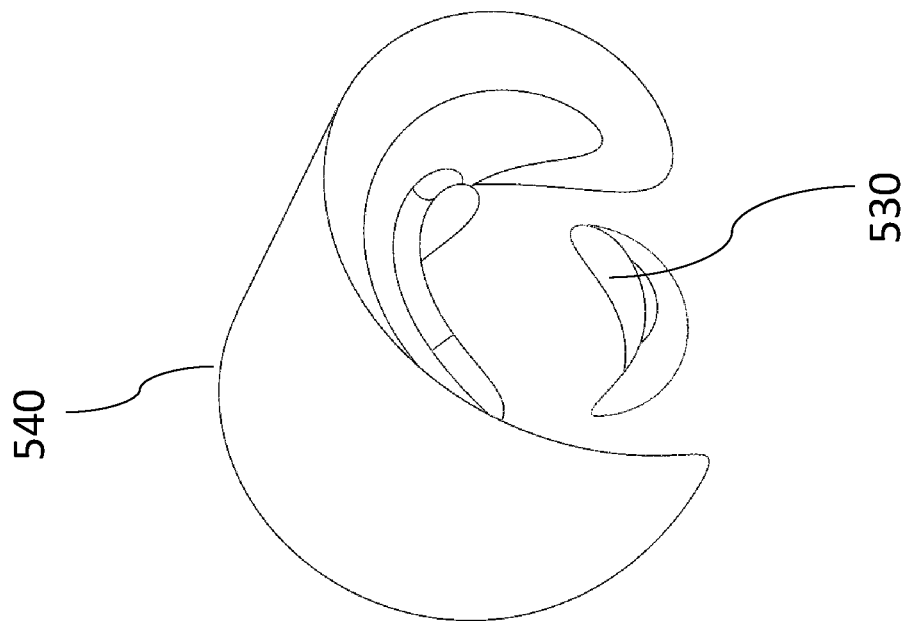
FIG. 25H shows the two flexibility regions removed from the tube of FIG. 25G to show a volume of each region.
Figure 25G:
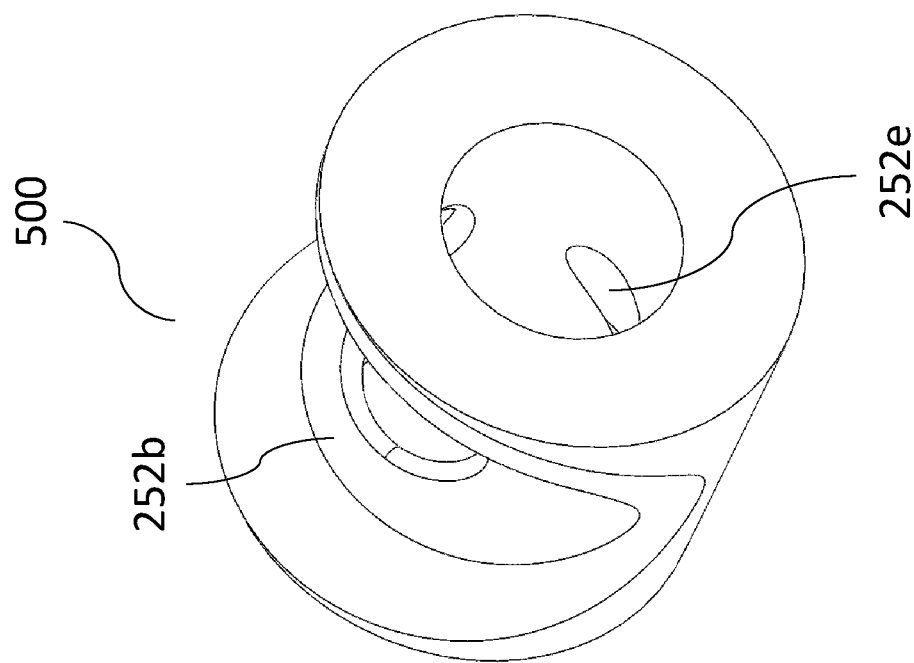
FIG. 25G shows a three-dimensional perspective view of a flexibility region of the embodiment of FIG. 25A.
Figure 25J:
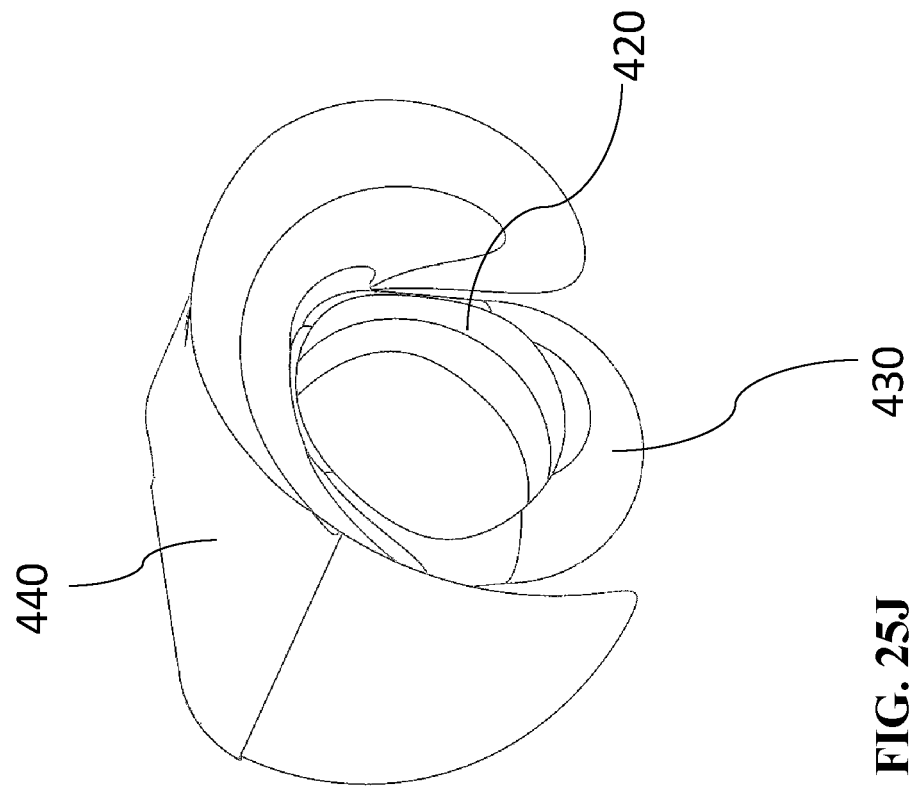
FIG. 25J shows the distal most flexibility region removed from the tube of FIG. 25I to show a volume of each region.
Figure 25I:
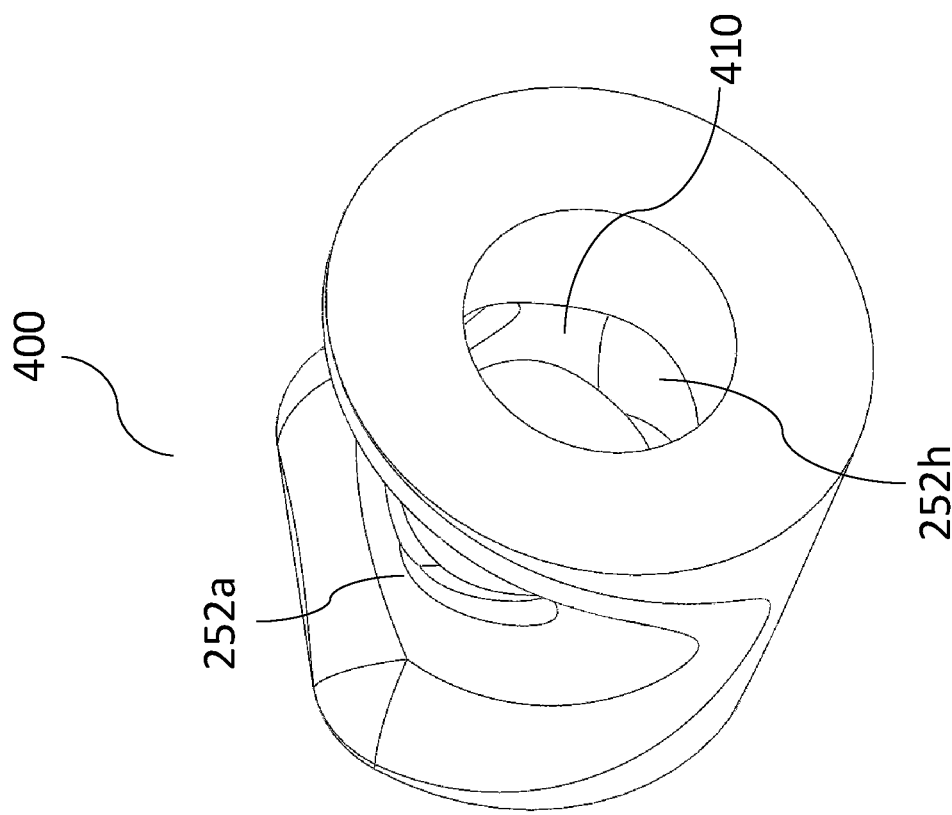
FIG. 25I shows a three-dimensional perspective view of a distal most flexibility region (an anterior flexibility region connected to a posterior flexibility region) of the embodiment of FIG. 25A.

In some embodiments, as shown in FIGS. 25I-25J, an anterior flexibility region 252*a* is continuous with a posterior flexibility region 252*h*, such that at least a portion of an inner sidewall 410 of the lumen is removed between the anterior flexibility region 252*a* and the posterior flexibility region 252*h*. In such embodiments, the volume percentage is a combined representation of the material removed from both regions (anterior material 440 that is removed from region 252*a*, posterior material 430 that is removed from region 252*h*) and the luminal wall material 420 that is removed from region 410 in between the anterior region 252*a* and the posterior region 252*h*, relative to tube 400, as shown in FIGS. 25I-25J.

A shown in FIG. 25J, a volume percent of the distal most flexibility region that includes anterior material removal 440 on an anterior side, posterior material removal 430 on an interior posterior side, and at least partially circumferentially 420 in the lumen between the anterior and posterior sides is about 20% to about 40%, preferably about 25% to about 35%.

In some embodiments, as shown in FIGS. 25G-25H, an anterior flexibility region 252*b* is separated from a posterior flexibility region 252*e*, but the regions collectively promote bending of the catheter in an anterior direction. In such embodiments, the volume percentage is a combined representation of the material removed from both regions (anterior material 540 that is removed from region 252*b* and posterior material 530 that is removed from region 252*e*), relative to tube 500, as shown in FIGS. 25G-25H. The combined volume percent is about 20% to about 40%, preferably about 25% to about 35%.

As shown in FIG. 25H, a volume percent of, for example, anterior flexibility region 252*b*, which includes anterior material removal 540 and some luminal circumferential material removal, is about 20% to about 40% or about 25% to about 30%. Further, a volume percent of, for example, posterior flexibility region 252*e*, which includes posterior material removal 530, is about 0.1% to about 2% or about 0.5% to about 10%.

Figure 26A:
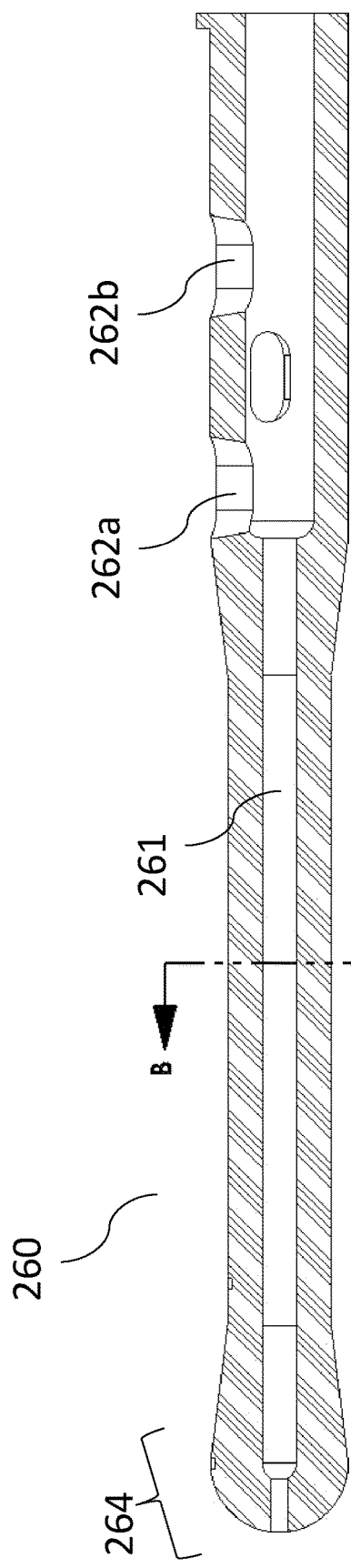
FIG. 26A shows a side-sectional view of another embodiment of a flexible catheter having one or more polygonal shaped apertures.
Figure 26B:
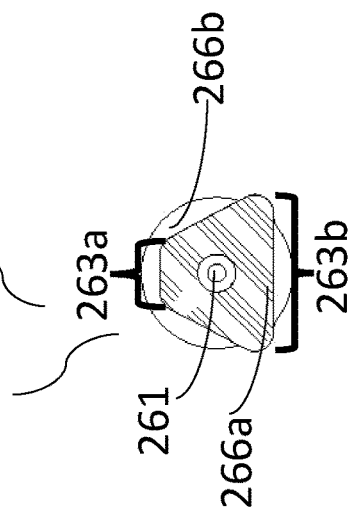
FIG. 26B shows cross-section B-B of FIG. 26A.

Still further, any of the preceding embodiments described herein may include an elongate body that is polygonal in cross-section, similar to that shown in FIGS. 26A-26B. FIGS. 26A-26B show an elongate body 260 defining a lumen 261 therethrough and comprising a distal tip 264. In this embodiment, as shown in FIG. 26B which is along section B-B of FIG. 26A, the polygonal shape of the body (with a narrow anterior width 263*a* and a wide posterior width 263*b*) is inclined to bend more readily anteriorly when experiencing an axial force. For example, the posterior side may have a width 263*b* of about 2 mm to about 5 mm while an anterior side may have a width 263*a* of 1 mm to about 3 mm. In one embodiment, material is added to a posterior side of the catheter, such that the posterior side or a posterior inner wall of a lumen of elongate body 260 such that the posterior side has a width that is greater than an anterior side. In another embodiment, material is added to a posterior side of an external surface of the elongate body 260 to create a polygonal shape that preferentially bends anteriorly. Further, although a trapezoidal polygon (i.e., a trapezoidal prism or three-dimensional trapezoid) is shown in FIGS. 26A-26B, one of skill in the art will appreciate that any polygonal shape is within the scope of this disclosure, including but not limited to: rectangles (i.e., rectangular prism, rectangular cuboid, rectangular parallelepiped), triangles (i.e., triangular prism, elongate rectangular prism), and any flat or straight surfaces may be replaced with curved surfaces, etc.

Figure 27A:
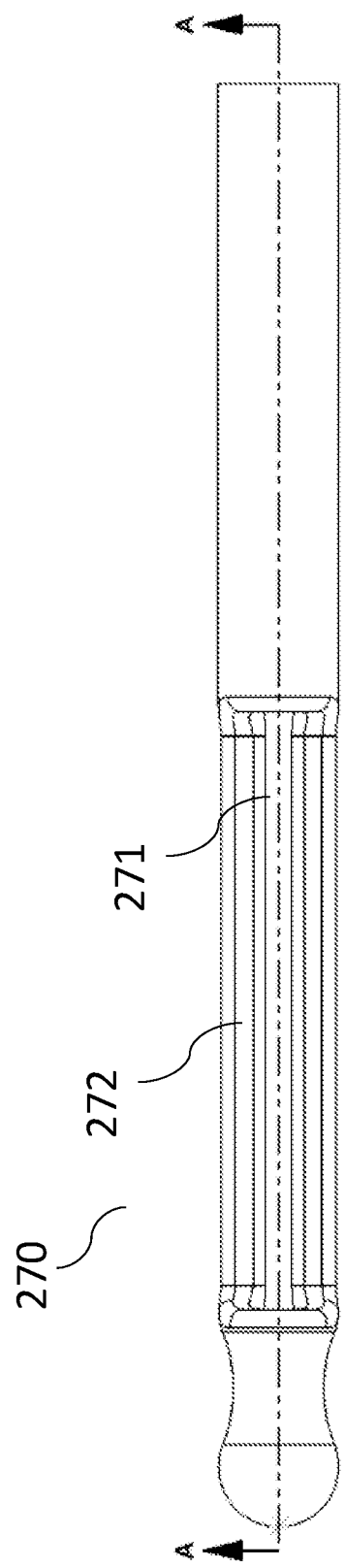
FIG. 27A shows a top view of another embodiment of a flexible catheter having an elongated flexible bending section.
Figure 27B:
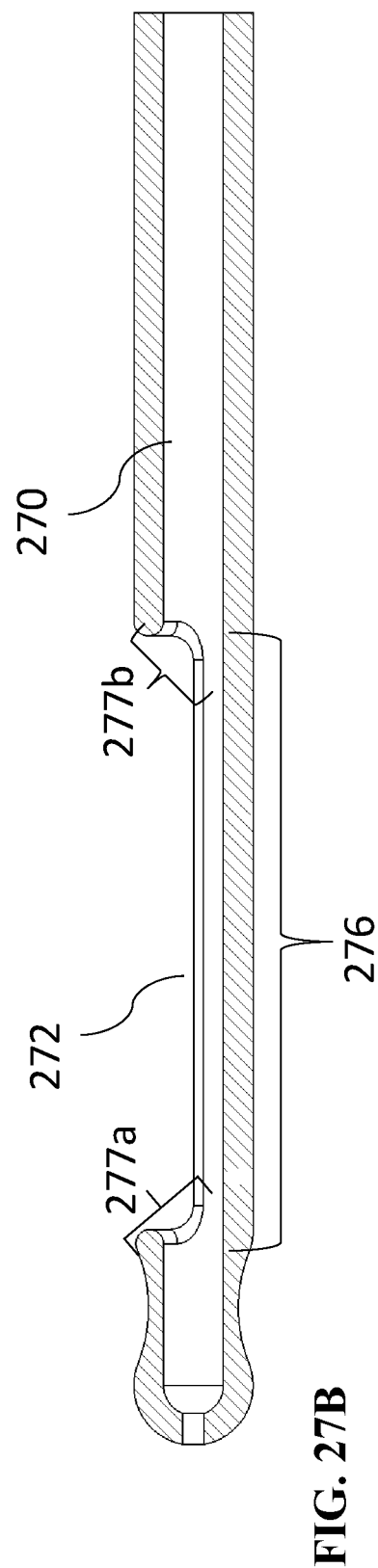
FIG. 27B shows a cross-sectional view of the embodiment of FIG. 27A.

In some embodiments, a flexibility region may comprise an elongate aperture, for example as shown in FIGS. 27A-27B. FIGS. 27A-27B show an elongate body 270 defining a lumen 271 therethrough and comprising an elongate flexibility region 272. A cut length percentage 276 of flexibility region 272 may be about 5% to about 90% of the length of the elongate body 270 or about 15% to about 30% of the length of the elongate body 270. The flexibility region 272 may be such that it extends into the lumen 271 so that the lumen 271 has an elongate trough opening that is the flexibility region 272. As shown in FIG. 27B, which is a cross-section of FIG. 27A along section A-A, the flexibility region 276 may be a substantially "U" shaped, for example, such that an interior angle 277*a*, 277*b* of end of the flexibility region is curved. Although a "U" shaped curve is shown, one of skill in the art will appreciate that sharp corners or slanted corners, etc. are also contemplated herein. The features of flexibility region 272 may be applied to any of the flexibility regions described elsewhere herein.

In another embodiment, as shown in FIGS. 28A-28C (FIG. 28C being along section A-A of FIG. 28A), an elongate body 280 may comprise a plurality of flexibility regions 282 (e.g., 282*a*, 282*b*, 282*c*, 282*d*, 282*e*). One or more of the flexibility regions may comprise an aperture such that the flexibility region extends through an anterior sidewall 288*a* through a lumen 281 and through a luminal surface 287 of a posterior sidewall 288*b* (without breaking an exterior surface of the posterior sidewall), such that one or more of the flexibility regions 282 comprise a cut depth percentage (that does not include the depth cut in the posterior wall) of about 30% to about 70%. The cut depth percentage 285*a* of one or more of the flexibility regions is about 50% to about 95%. For example, a 6 mm outer diameter catheter may have a cut depth of about 2.5 mm to about 3.5 mm. Further, each of the flexibility regions 282 comprise a cut depth percentage 285*a* of about 5% to about 55%. A volume percentage of one or more of the flexibility regions is about 10% to about 40% or about 25% to about 35% (representation of material removed 530, 540 from a tube 500 is shown in FIGS. 25G-25H). The flexibility regions 282, as shown in FIG. 28C, extend from an anterior side and penetrate the lumen such that material is removed circumferentially about the lumen and include some material removal on a luminal posterior side.

In the embodiment shown in FIGS. 28A-28C, the plurality of flexibility regions 282 also comprises drainage or flushing apertures since the plurality of flexibility regions extends into the lumen 281. Elongate body 280 may further comprise a retention balloon (not shown), one or more proximal indicators (not shown), one or more additional apertures for draining/flushing (shown in 282*a-d*, 282*e*), etc. Additionally, or alternatively, elongate body 280 may comprise any of the distal tip 284 configurations described elsewhere herein, for example with reference to FIG. 19A-19C, 22A-22C, 23, 25A-25C.

In some embodiments of FIGS. 28A-28C, the distal most flexibility region may have a greater cut depth percentage than the other flexibility regions that reside more proximally, for example similar to that described in connection with FIG. 25C. Additionally, or alternatively, embodiments of FIGS. 28A-28C may also include posterior flexibility regions comprising grooves in an inner sidewall of the lumen of the elongate body, as described in connect with FIG. 25C. Additionally, or alternatively, embodiments of FIGS. 28A-28C may also include a tapered distal tip, as described in connection with FIG. 25B.

As shown in FIG. 28C, distal tip 284 may define aperture 283 for passing a guidewire or other instrument therethrough and/or for drainage/flushing. In other embodiments of FIGS. 28A-28C, distal tip 284 does not define an aperture. Further, although the flexibility regions in FIGS. 28A-28C are shown on an anterior side of the elongate body, one of skill in the art will appreciate that the flexibility regions may also reside on a posterior side of the elongate body. Further, elongate body 280 may comprise any of the internal flexibility regions and/or posterior flexibility regions described elsewhere herein, for example, the internal regions or posterior flexibility regions of FIGS. 8B, 9B, 16E-16F, 19F-19G, 20B, 21B, 25C. Further, elongate body 280 may comprise one or more proximal flexibility regions described elsewhere herein, for example, those of FIGS. 24A-24D.

For all the above embodiments in FIGS. 6A-28C, there is a balance between maintaining column strength along the length of the catheter (for controlled and predictable pushability) while also limiting the amount of pressure that the catheter exerts on the anatomy (described herein as wall pressure) when it is being advanced or retracted. Said another way, wall pressure is the local maximum pressure exerted on the wall by the catheter. Local high pressure will cause deformations in the catheter lumen which can cause the catheter to get stuck. The catheter lumen can have complex stiffness behavior, so one way of reducing significant deformation is to minimize the wall pressure.

Various parameters were investigated via mechanical test fixtures and computer simulations for their impact on column strength and wall pressure and for their impact on insertion force or pressure required to deflect a distal segment of the catheter. For example, as shown in FIG. 29A, the cut length, cut depth, cut location, and the number of segments were varied to determine the impact on column strength, wall pressure, and insertion force.

Figure 30A:
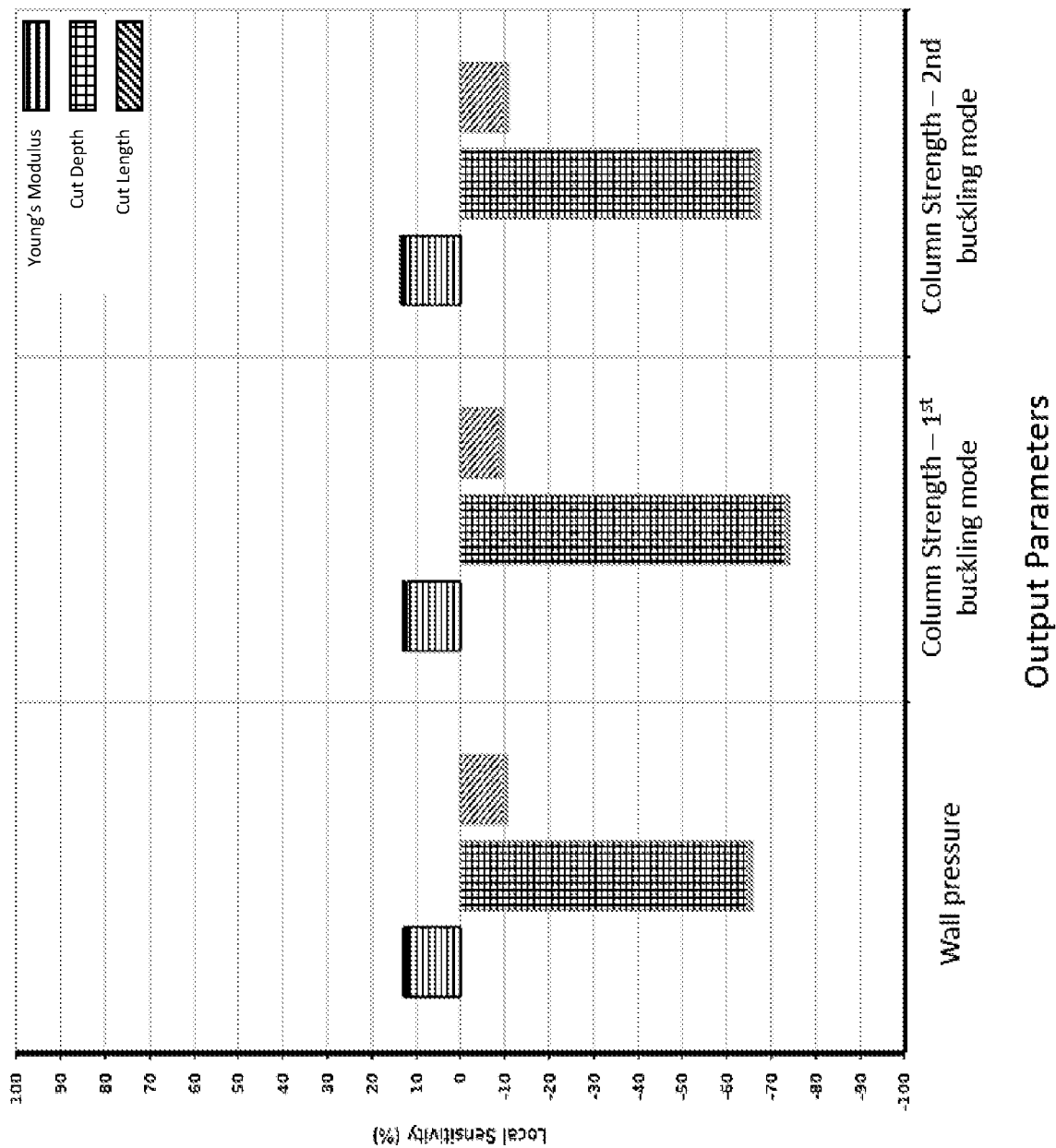
FIG. 30A shows a graph comprising data from ANSYS® computation analysis in which various catheter features were analyzed for their impact on wall pressure and column strength.
Figure 30B:
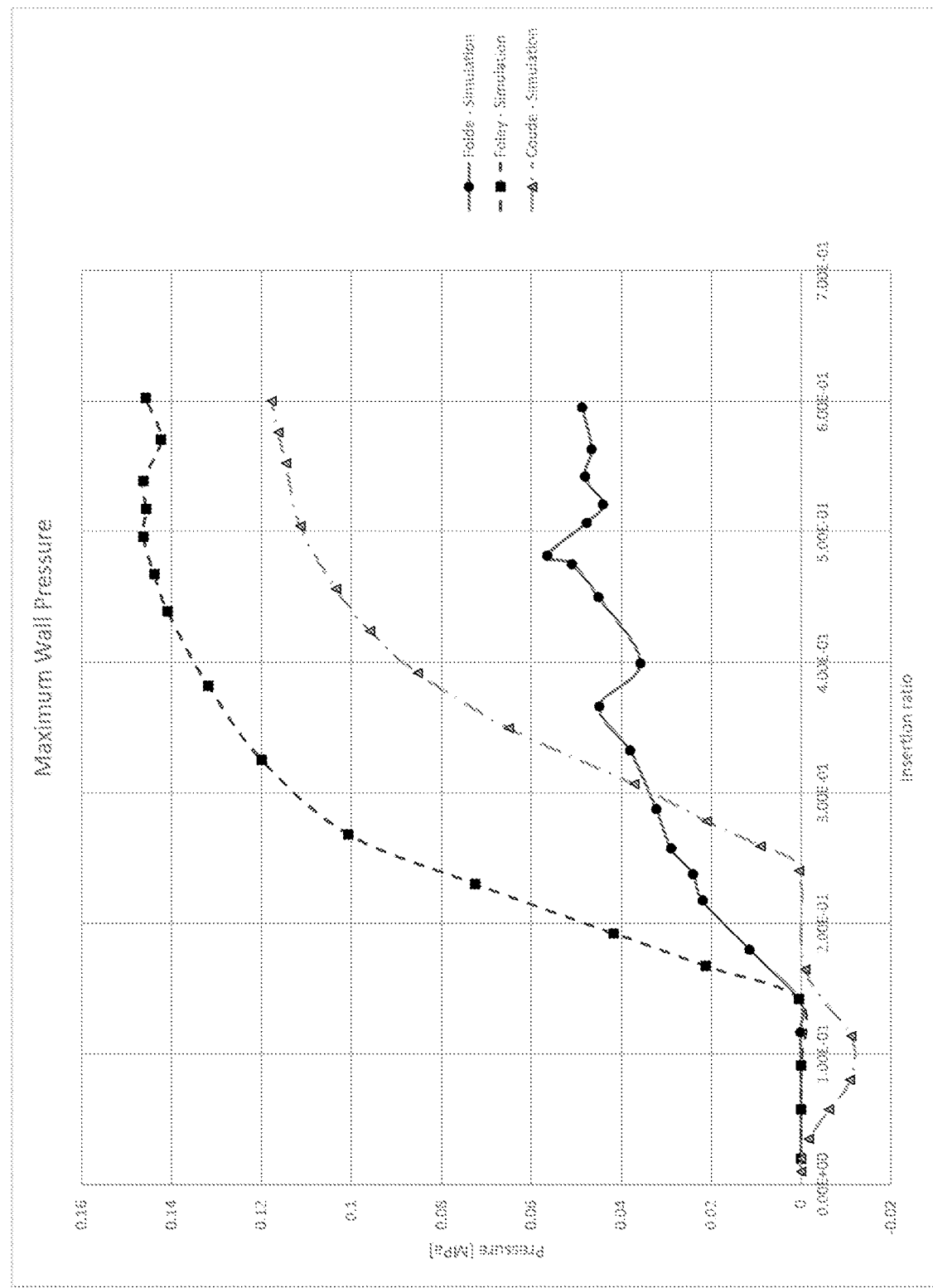
FIG. 30B shows a graph comprising data from ANSYS® computational analysis in which various standard of care catheters were compared to a catheter embodiment described herein.

For example, various catheter designs were analyzed using computer software-based simulation (Ansys® Mechanical software package). Exemplary data from these analyses are shown in FIGS. 30A-30B. The computer simulation analysis measures the internal forces (force per distance inserted) of the catheter around the flexibility regions and interaction between the catheter and the anatomical path (wall pressure, as described elsewhere herein).

To accurately analyze the wall pressure, a simplified 3D CAD model of each catheter was created along with the tube representing the anatomical path that the catheter must negotiate. Nonlinear contact model with friction was used to model the interaction between the catheter and the tube. Linear or hyper elastic material was used depending on the material of the catheter and the accuracy of simulation needed. The tube was modeled as a rigid material in order to evaluate the flexibility and column strength of the catheter.

To evaluate the column strength, an eigenvalue buckling analysis was performed with a unit compressive load applied to the catheter in a linear analysis.

The simplified 3D CAD model of the catheter was created to be fully parametric. As shown in FIG. 30A, the key input parameters investigated were material properties of the catheter, cut length percentage of the flexibility region, and cut depth percentage of the flexibility region. Insertion pressure, as shown in FIG. 30B, was analyzed and determined.

FIG. 30A shows normalized values (shown as percent local sensitivity on the y-axis) for catheter material properties (Young's Modulus), cut depth percentage, and cut length percentage as measured in a sensitivity study. A sensitivity study calculates the slope of the output variables to the input variables. Local sensitivity means the slope is calculated at a point in a multi-dimensional surface. FIG. 30A shows the slope of wall pressure and column strength versus Young's modulus, Cut Depth, and Cut Percentage. The outputs of the analysis, shown on the x-axis, were wall pressure, column strength (first buckling mode), and column strength (second buckling mode). Two buckling modes were assessed since a column typically buckles in two directions normal to the axis of the column. For example. if the axis of the column is Z then buckling may occur in the X axis or Y axis. As shown in FIG. 30A, the cut depth percentage had the largest impact on wall pressure and column strength. Cut length percentage also had an impact, but less so than cut depth percentage. The material properties, although still important to overall design, impacted the output parameters less than the cut depth or cut length.

FIG. 30B shows data from a computer simulation in which a Foley catheter, a Coudé® catheter, and a test catheter (e.g., FIGS. 28A-28C) were analyzed. The test catheter comprises a plurality of flexibility regions, each having a cut length percentage of about 70% to about 80% and a cut depth percentage of about 50% to about 70%. The data in FIG. 30B represent the pressure (MPa) a patient would experience when the catheter is inserted, advanced, or otherwise pushed into a lumen of a patient (represented as insertion ratio; ratio of catheter inserted into the bend region versus the total catheter length).

As shown in FIG. 30B, the Foldé® catheter imparted significantly less pressure to the surrounding tissue during insertion as compared to the standard of care Foley or the Coudé® catheter analogs. The Foldé® catheter's maximum imparted pressure during insertion was about 39% of the Foley catheter's maximum and 43% of the Coudé® catheter's maximum.

Figure 31A:
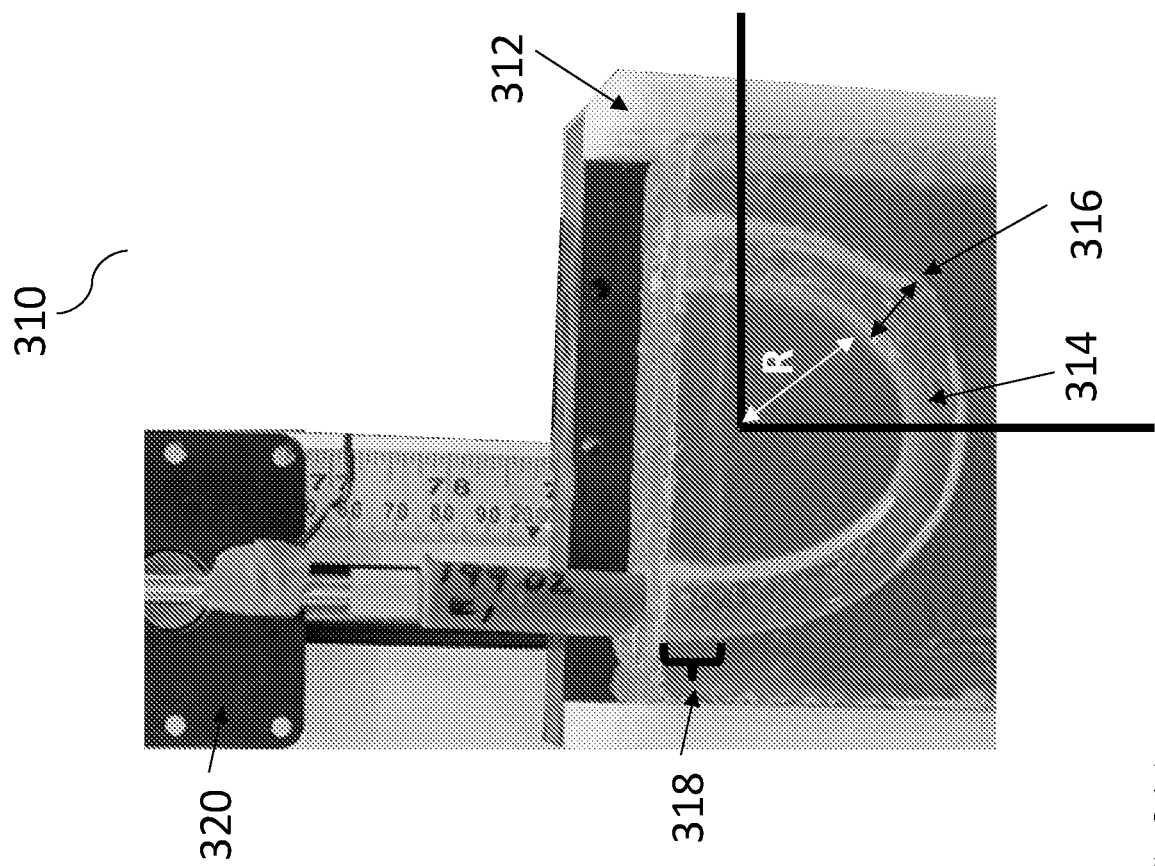
FIG. 31A shows an image of a test fixture for testing insertion force relative to insertion depth into a test lumen.
Figure 31B:
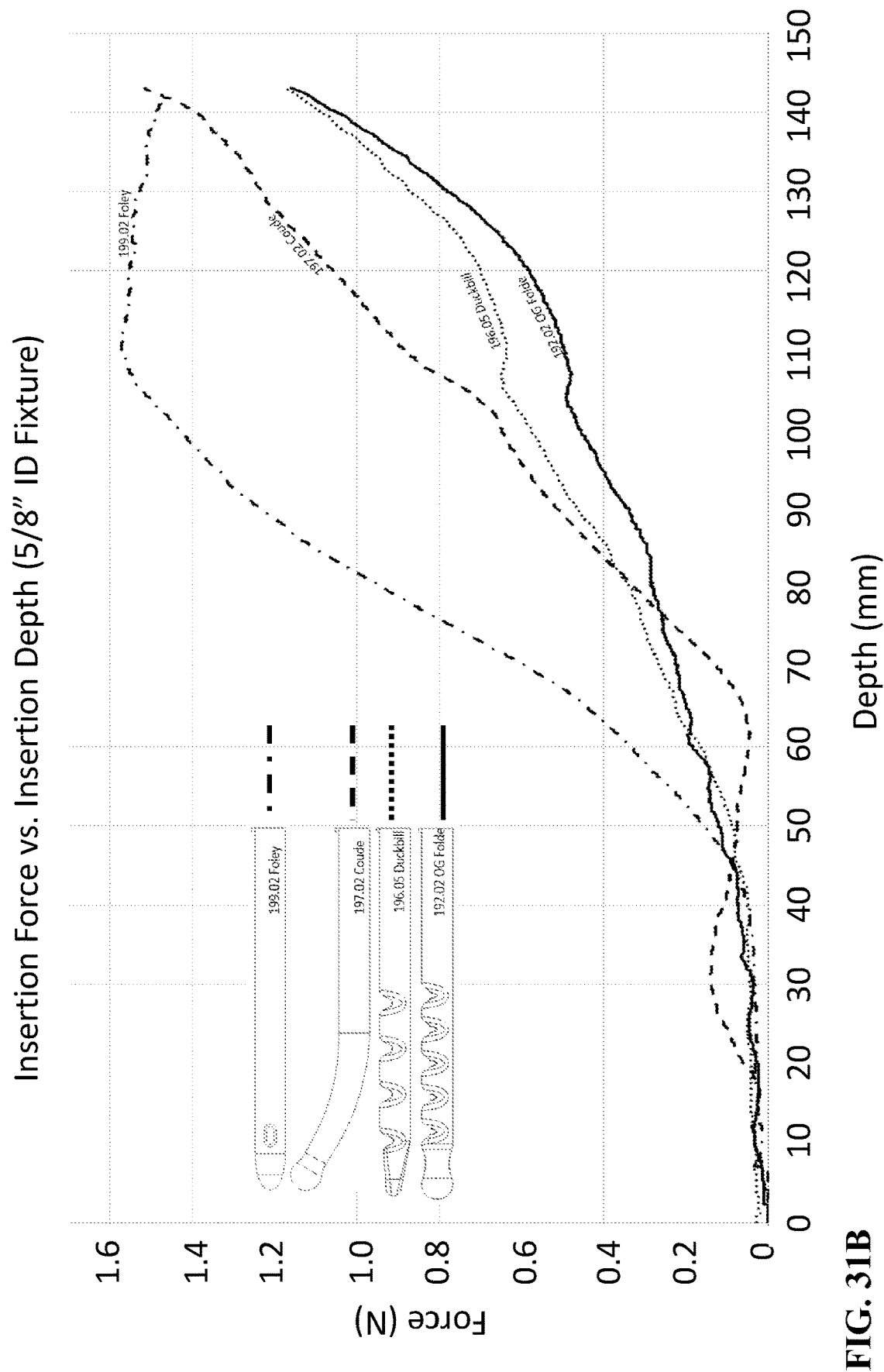
FIG. 31B shows a graph comprising data from physical testing of various standard of care catheter analogs compared to various catheter embodiments described herein.

In addition to computer simulation testing, a mechanical test fixture, as shown in FIG. 31A, was developed that would mimic the human patient anatomical path in size, feel, and tortuosity. The mechanical test fixture comprises a digital force gauge and a cast gel block 312 with a curved cylindrical lumen 314 to mimic a urethral bend. To form the test fixture's curved urethral lumen, casting gel is poured into a mold and left to harden. The durometer of the casting gel was approximately 10 Shore 00. Catheter insertion pathways were cast with inner diameters 316 of 0.25 inch (0.635 cm), 0.375 inch (0.9525 cm), 0.5 inch (1.27 cm), 0.5625 inch (1.42875 cm), and 0.625 inch (1.5875 cm). The bend radius R was about 32 mm. The catheter entered the gel along a straight path 318 for about 1 inch, transitioned to a 180 degree bend, and exited straight up and out of the gel for about 1 inch. Each catheter was attached to a motorized test stand 320 (MARK-10®, model ESM 301) that fed each catheter straight down into the casting gel block's artificial urethra at 330 mm/min while insertion force was recorded. Each catheter and pathway was generously lubricated with KY jelly to minimize the frictional forces. The force differences due to mechanical bending and negotiation of the tortuous path for each test catheter were measured and compared. All samples were run through the test setup at least three times; the run values were averaged to compare each design. Test results of insertion force versus insertion depth for each design were compared as shown in FIG. 31B. The testing was performed with 2× scale devices (both test and controls) that were 3D printed using rubber analog material of similar durometer and flexibility.

The data in FIG. 31B represent the force (compression) a user (e.g., physician, nurse, practitioner, etc.) experiences when inserting, advancing, or otherwise pushing a proximal end of the catheter into a lumen of a patient. In other words, the force measurement is on the proximal end of the catheter that is being pushed. As shown in FIG. 31B, the standard of care catheters, Foley and Coudé® had the highest insertion forces as compared to test 1 and 2 catheters. Test 1 catheter is the catheter shown in FIGS. 25A-25B (labeled "Duckbill" in FIG. 31B) and Test 2 catheter is described in conjunction with FIGS. 28A-28C (labeled "OG Foldé" in FIG. 31B).

As shown in FIG. 31B, test catheters 1 and 2 required significantly less insertion force to negotiate the simulated tortuous urethral tract when compared to the standard of care Foley and Coudé® catheters. The insertion force required for the tested embodiments to negotiate the curve in the model (entering the curve at about 50 mm of insertion and exiting the curve at about 110 mm of insertion) was significantly improved when compared to the standard of care embodiments. Test catheter 1 peaked at about 0.65 N, test catheter 2 peaked at about 0.50 N, the Foley catheter peaked at about 1.57 N, and the Coudé® catheter peaked at about 0.88N. Given these data and in general, any of the embodiments described herein comprising one or more flexibility regions (e.g., those shown in FIGS. 6A-27B) may be configured such that a maximum insertion force of less than about 0.75 N is required to insert the catheter into a bodily lumen. In some embodiments, the maximum insertion force may be less than about 0.70 N, less than about 0.60 N, less than about 0.55N, or between about 0.40 N and about 0.80 N, between about 0.45 N and about 0.75 N, between about 0.5 N and about 0.80 N, etc.

Figure 32:
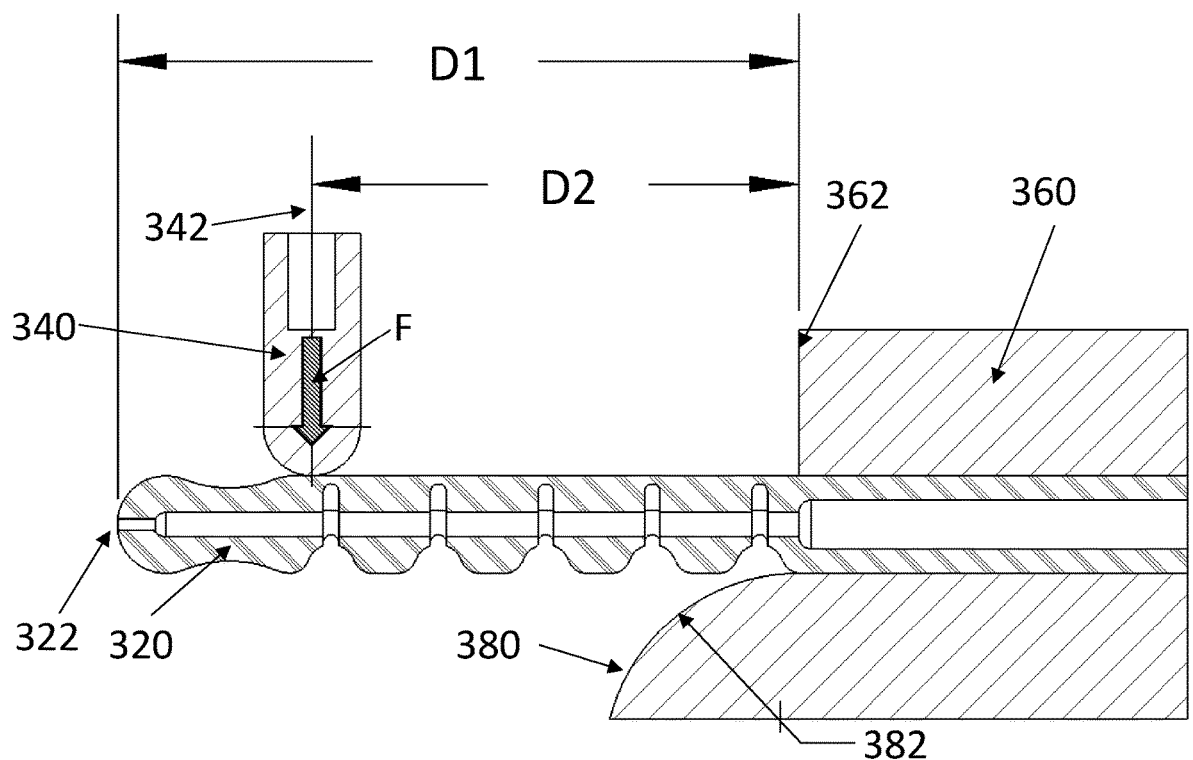
FIG. 32 shows a schematic of a test fixture for testing force needed to deflect a distal end portion of exemplary flexible catheters.
Figure 33:
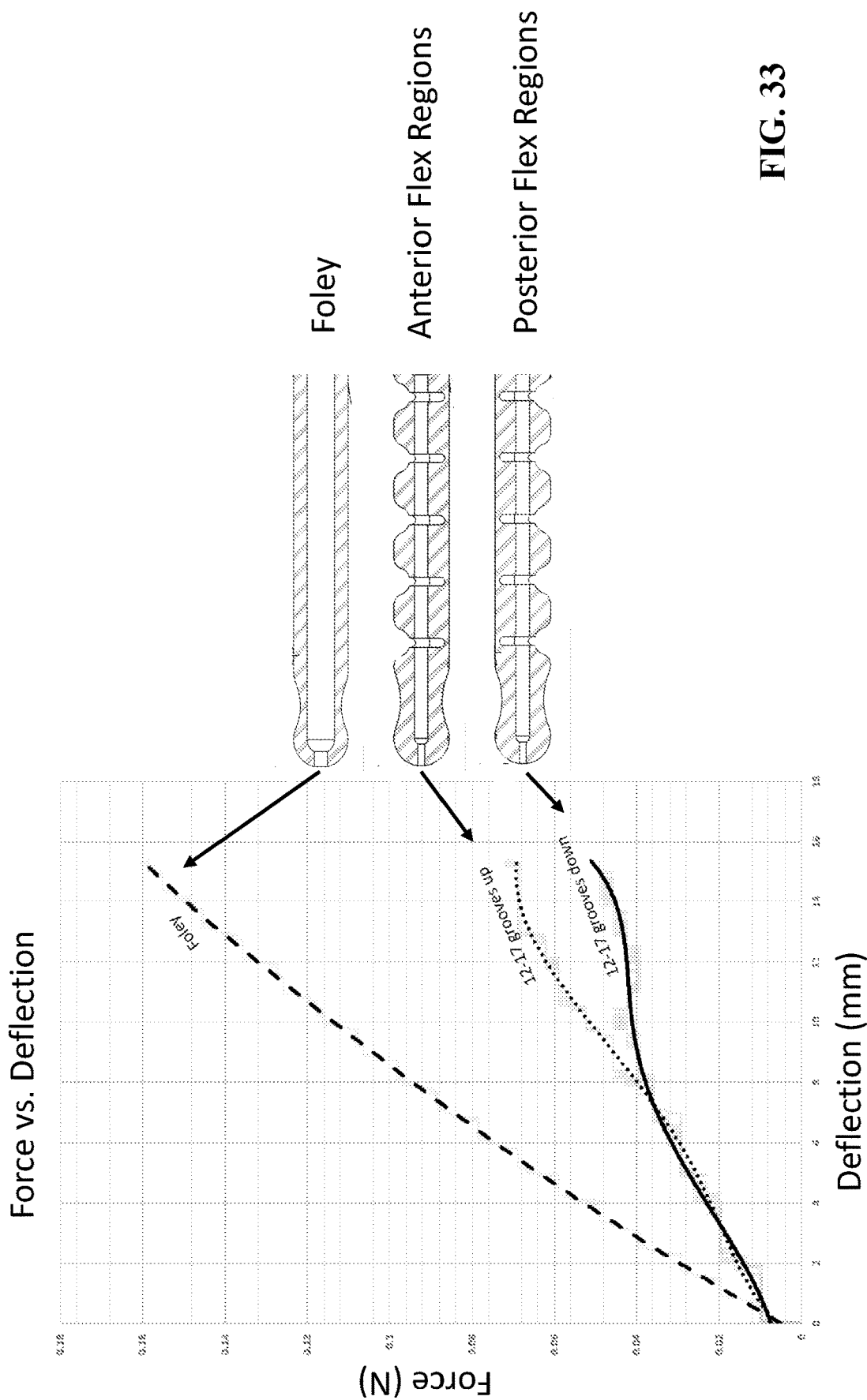
FIG. 33 shows a graph comprising deflection force vs. amount of deflection over a fixed curved surface for catheters comprising flexibility regions that extend from an external surface to an internal region, using the test fixture of FIG. 32.
Figure 34:
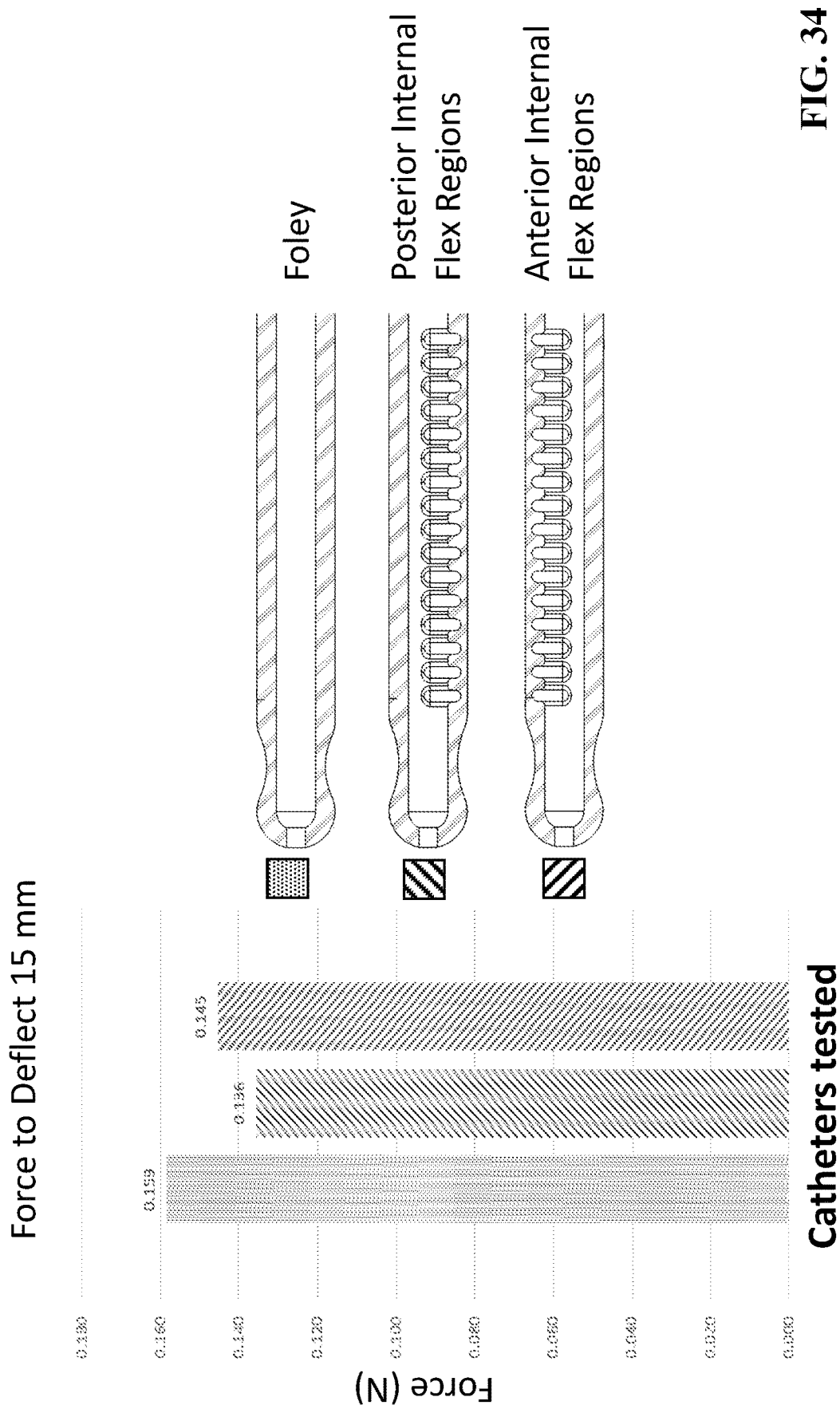
FIG. 34 shows a graph comprising force to deflect data for catheter comprising flexibility regions that are internal (do not break an external surface), using the test fixture of FIG. 32.

FIGS. 32-34 show another exemplary test fixture and resulting data to determine deflection force needed for various flexible catheters, described elsewhere herein. Said another way, the test fixture shown in FIG. 32 is configured to measure bending force over a radius. Although a few exemplary embodiments were tested, one of skill in the art will appreciate that other catheters described herein and comprising similar flexibility regions may also behave similarly as shown. As shown in FIG. 32, each catheter 320 is proximally restrained by a block 360 while a vertical load (indenter) 340 is pressed against (applies force F) the catheter 320. The distal end 362 of block 360 was positioned at a first distance D1 of about 3.5 inches (88.9 mm) from a distal tip 322 of the catheter 320 and the vertical load 340 was positioned at a second distance D2 of about 2.5 inches (63.5 mm), measured from the central axis 342 of the vertical load 340, from the distal end 362 of the block 360. The catheter 320 was bent along curved surface 380 having a radius 382 of about 1 inch (25.4 mm). The speed of the vertical load 340 was 100 mm per minute and was applied by a motorized test stand (MARK-10®, model ESM 301). The force F was measured by a MARK-10® Force Gauge, model M3-2.

FIG. 33 shows a graphical representation of the force (in N) vs. deflection (in mm) to deflect from 0 to 15 mm for various catheters, where a higher number indicates more resistance to bending. For a standard of care Foley catheter, the deflection force substantially increased linearly over time, requiring a maximum force of about 0.16 N to deflect 15 mm. In contrast, catheters having posterior or anterior flexibility regions (shown here as five regions, also described in connection with FIGS. 28A-28C or shown as regions 152a of FIGS. 15A-15D) required a maximum force of about 0.069 N ("cut" grooves up) and 0.052 N ("cut" grooves down) to deflect 15 mm.

FIG. 34 shows a graphical representation of the force (in N) required to deflect (in mm) the catheters shown 15 mm. As shown in FIG. 34, a standard of care Foley catheter was tested and compared to two test catheters, one having a plurality of internal posterior flexibility regions and the other having a plurality of internal anterior flexibility regions. Exemplary embodiments of catheters having internal flexibility regions are shown in FIGS. 20A-20G and FIGS. 21A-21B. For a standard of care Foley catheter, the deflection force required to deflect the catheter 15 mm was 0.159 N. In contrast, catheters having posterior or anterior internal flexibility regions required a maximum force of 0.145 N for anteriorly positioned internal flexibility regions and 0.136 N for posteriorly positioned internal flexibility regions.

Figure 35:
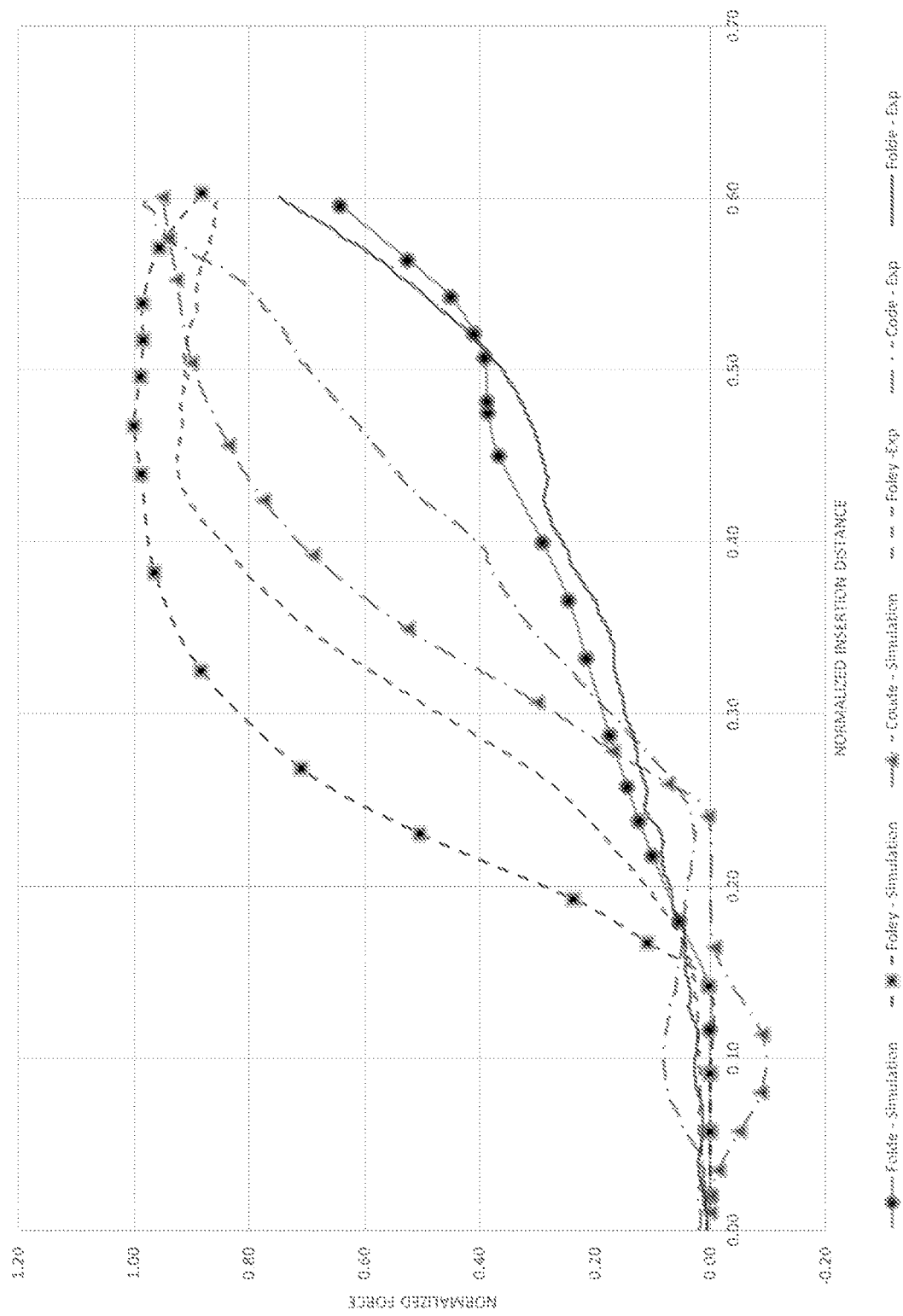
FIG. 35 shows the simulation data of FIG. 30B normalized with the test fixture data of FIG. 33.

To illustrate the rigor of the simulation and test fixture data and to compare the data from the simulation and test fixture, as shown in FIG. 35, the data were normalized for the insertion force (y-axis) and the insertion distance (x-axis). The y-axis was normalized with the maximum insertion force from the test fixture data and the simulation data. The x-axis was normalized by the length of the catheter. The maximum of 0.6 means 60% of the catheter was inserted. As shown in FIG. 35, the standard of care Foley and Coudé® catheters required high amount of force to insert into the fixture (both actual and modelled), whether tested in a simulated or physical test fixture. In contrast, the test catheter (labeled as Folde, shown and described in FIGS. 28A-28C) required significantly less force to insert. On average, the test catheter required about 58% less force to insert than either the Foley or the Coudé catheter.

As used in the description and claims, the singular form "a", "an" and "the" include both singular and plural references unless the context clearly dictates otherwise. For example, the term "flexibility region" may include, and is contemplated to include, a plurality of flexibility regions. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A catheter comprising:
   an elongate body having a proximal segment and a distal segment;
   a first lumen defined by the elongate body; and
   at least one anterior flexibility region on or in the distal segment of the elongate body, wherein the at least one anterior flexibility region:
      extends from an anterior external surface of the elongate body into the first lumen,
      extends from the anterior external surface at least partially circumferentially along an exterior sidewall of the elongate body without penetrating the first lumen along the exterior sidewall,
      has a cut depth percentage of about 40% to about 50% of an outer diameter of the elongate body, and
      has a percent volume of material removed of about 20% to about 40%.

2. The catheter of claim 1, wherein a force to bend the at least one anterior flexibility region is less than the force to bend a portion of the elongate body that does not include the at least one anterior flexibility region.

3. The catheter of claim 1, wherein a force to bend the distal segment anteriorly is less than the force to bend the distal segment posteriorly.

4. The catheter of claim 1, wherein the at least one anterior flexibility region has a cut length percentage of about 10% to about 90%.

5. The catheter of claim 1, wherein the catheter is a urinary catheter comprising:
   a retention balloon disposed about at least a portion of the distal segment of the elongate body, and
   a second lumen defined by the elongate body and configured to inflate the retention balloon.

6. The catheter of claim 1, wherein a distal tip of the distal segment is tapered such that a ratio of the outer diameter of the elongate body to an outer projected thickness of the distal tip of the distal segment is about 1.0:0.8 to about 1.0:0.2.

7. The catheter of claim 1, wherein the at least one anterior flexibility region comprises a plurality of anterior flexibility regions on or in the distal segment, such that a distal most anterior flexibility region of the plurality of anterior flexibility regions has a second cut depth percentage that is greater than the cut depth percentage of the at least one anterior flexibility region.

8. The catheter of claim 1, further comprising at least one posterior flexibility region on or in the distal segment.

9. The catheter of claim 7, wherein the distal most anterior flexibility region extends from a second region of the anterior external surface of the elongate body, circumferentially about an inner sidewall of the first lumen, and into a luminal surface of a posterior sidewall of the elongate body.

10. The catheter of claim 7, wherein the second cut depth percentage of the distal most anterior flexibility region is about 60% to about 95% of the outer diameter of the elongate body.

11. The catheter of claim 8, wherein the at least one posterior flexibility region comprises a groove in a posterior portion of an inner sidewall of the first lumen of the elongate body.

12. The catheter of claim 11, wherein the groove in the posterior portion of the inner sidewall of the first lumen has a posterior cut depth percentage of about 5% to about 20% of a wall thickness of the elongate body.

13. A catheter comprising:
   an elongate body having a proximal segment and a distal segment;
   a lumen defined by the elongate body; and
   at least one anterior flexibility region on or in the distal segment of the elongate body, wherein the at least one anterior flexibility region:
      extends through an anterior external sidewall of the elongate body, circumferentially about an inner sidewall of the lumen, and into a luminal surface of a posterior sidewall of the elongate body,
      has a cut depth percentage of about 80% to about 95% of an outer diameter of the elongate body, and
      has a percent volume of material removed of about 20% to about 40%, wherein the material removed is from the anterior external sidewall, the inner sidewall of the lumen, and the luminal surface of the posterior sidewall.

14. The catheter of claim 13, wherein a distal tip of the distal segment is tapered such that a ratio of the outer diameter of the elongate body to an outer projected thickness of the distal tip of the distal segment is about 1.0:0.8 to about 1.0:0.2.

15. The catheter of claim 13, wherein the at least one anterior flexibility region has a cut length percentage of about 10% to about 90%.

16. A catheter comprising:
   an elongate body having a proximal segment and a distal segment, wherein a distal tip of the distal segment is tapered such that a ratio of an outer diameter of the elongate body to an outer projected thickness of the distal tip of the distal segment is about 1.0:0.8 to about 1.0:0.2;
   a lumen defined by the elongate body; and
   a plurality of anterior flexibility regions on or in the distal segment of the elongate body,
   wherein at least one anterior flexibility region of the plurality of anterior flexibility regions:
      extends from a first region of an anterior external surface of the elongate body into the lumen, extends from the first region of the anterior external surface at least partially circumferentially along a first exterior sidewall of the elongate body, and has a percent volume of material removed of about 20% to about 40%.

17. The catheter of claim 16, wherein a second anterior flexibility region of the plurality of anterior flexibility regions:

extends through a second region of the anterior external surface of the elongate body, circumferentially about an inner sidewall of the lumen, and into a luminal surface of a posterior sidewall of the elongate body, has a cut depth percentage of about 80% to about 95% of the outer diameter of the elongate body, and has a second percent volume of material removed of about 20% to about 40%.

18. The catheter of claim 16, further comprising a plurality of posterior flexibility regions on or in the distal segment, wherein each of the plurality of posterior flexibility regions are transversely aligned with a respective anterior flexibility region of the plurality of anterior flexibility regions.

19. The catheter of claim 18, wherein each of the plurality of posterior flexibility regions comprise a posterior groove in an inner sidewall of the lumen and have a cut depth percentage of about 5% to about 20% relative to the outer diameter of the elongate body.

* * * * *